(12) United States Patent
Thomas et al.

(10) Patent No.: US 6,294,532 B1
(45) Date of Patent: Sep. 25, 2001

(54) OXINDOLYLQUINAZOLINE DERIVATIVES AS ANGIOGENESIS INHIBITORS

(75) Inventors: Andrew Peter Thomas, Macclesfield (GB); Jean-Jacques Marcel Lohmann, Reims Cedex (FR); Laurent Francois Andre Hennequin, Reims Cedex (FR); Patrick Ple, Reims Cedex (FR)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/486,051

(22) PCT Filed: Aug. 19, 1998

(86) PCT No.: PCT/GB98/02493

§ 371 Date: May 3, 2000

§ 102(e) Date: May 3, 2000

(87) PCT Pub. No.: WO99/10349

PCT Pub. Date: Mar. 4, 1999

(30) Foreign Application Priority Data

Aug. 22, 1997 (EP) ................................................. 97401972
Aug. 22, 1997 (EP) ................................................. 97401973
Aug. 22, 1997 (EP) ................................................. 97401974

(51) Int. Cl.[7] ..................... C07D 279/12; C07D 413/00; C07D 487/00; C07D 413/04; C07D 487/12

(52) U.S. Cl. ..................................... 514/228.2; 514/228.5; 514/233.8; 514/234.2; 514/234.5; 514/258; 514/259; 544/58.2; 544/116; 544/117; 544/280; 544/284

(58) Field of Search ..................................... 544/116, 117, 544/284, 280, 58.2; 514/233.8, 234.2, 234.5, 259, 258, 228.2, 228.5

(56) References Cited

U.S. PATENT DOCUMENTS

| | | | |
|---|---|---|---|
| Re. 36,265 | 7/1999 | Spada et al. | 514/249 |
| 5,409,930 | 4/1995 | Spada et al. | 514/248 |
| 5,411,963 | 5/1995 | Dreikorn et al. | 514/259 |
| 5,457,105 | 10/1995 | Barker | 514/234.5 |
| 5,475,001 | 12/1995 | Barker | 514/258 |
| 5,480,883 | 1/1996 | Spada et al. | 514/249 |
| 5,569,658 | 10/1996 | Barker | 514/250 |
| 5,580,870 | 12/1996 | Barker et al. | 514/234.5 |
| 5,616,582 | 4/1997 | Barker | 514/234.5 |
| 5,646,153 | 7/1997 | Spada et al. | 514/259 |
| 5,650,415 | 7/1997 | Tang et al. | 514/312 |
| 5,710,158 | 1/1998 | Myers et al. | 514/259 |
| 5,712,395 | 1/1998 | App et al. | 514/344 |
| 5,714,493 | 2/1998 | Myers et al. | 514/259 |
| 5,721,237 | 2/1998 | Myers et al. | 514/259 |
| 5,736,534 | 4/1998 | Arnold | 514/63 |
| 5,770,599 | 6/1998 | Gibson | 514/228.2 |
| 5,770,603 | 6/1998 | Gibson | 514/259 |
| 5,792,771 | 8/1998 | App et al. | 514/259 |
| 5,814,630 | 9/1998 | Barker et al. | 514/234.5 |
| 5,821,246 | 10/1998 | Brown et al. | 514/253 |
| 5,866,572 | 2/1999 | Barker et al. | 514/234.5 |
| 5,932,574 | 8/1999 | Barker | 514/234.5 |
| 5,942,514 | 8/1999 | Barker | 514/259 |
| 5,952,333 | 9/1999 | Barker | 514/259 |
| 5,955,464 | 9/1999 | Barker | 514/259 |
| 5,962,458 | 10/1999 | Lohmann et al. | 514/259 |
| 6,002,008 | 12/1999 | Wissner et al. | 546/160 |
| 6,015,814 | 1/2000 | Barker | 514/259 |
| 6,057,320 | 5/2000 | Spada et al. | 514/259 |
| 6,071,921 | 6/2000 | Lohmann et al. | 514/259 |
| 6,184,225 | 2/2001 | Thomas et al. | 514/259 |

FOREIGN PATENT DOCUMENTS

| | | |
|---|---|---|
| 19614718 | 10/1997 | (DE) . |
| 0 326 330 A2 | 8/1989 | (EP) . |
| 0 602 851 A1 | 6/1994 | (EP) . |
| 0 743 308 | 11/1996 | (EP) . |
| 0 787 722 A1 | 8/1997 | (EP) . |
| 0 837 063 A1 | 4/1998 | (EP) . |
| WO 87/04321 | 7/1987 | (WO) . |
| WO 92/16527 | 10/1992 | (WO) . |
| WO 92/20642 | 11/1992 | (WO) . |
| 95/15758 A | 6/1995 | (WO) . |
| WO 95/19169 | 7/1995 | (WO) . |
| 95/23141 A | 8/1995 | (WO) . |
| WO 95/21613 | 8/1995 | (WO) . |
| WO 96/29331 | 9/1996 | (WO) . |
| WO 96/30370 | 10/1996 | (WO) . |
| WO 96/39145 | 12/1996 | (WO) . |

(List continued on next page.)

OTHER PUBLICATIONS

Gazit et al., Tyrophostins IV–Highly Potent Inhibitors . . . Relationship Study of 4–Anilidoquinazolines, Bioorganic & Medicinal Chemistry, vol. 4. No. 8, 1996, pp. 1203–1207.

Sinyak, et al., Synthesis and Biological Properties of Derivatives of 4–Heterylmercaptoquinazoline, Zaporozh'e Medical Institute pp. 103–106, translated from Khimiko–farmatsevticheskii Zhurnal, vol. 20, No. 2, Feb. 1986, 168–171, original article submitted Dec. 29, 1984.

*Primary Examiner*—Bruck Kifle
(74) *Attorney, Agent, or Firm*—Pillsbury Winthrop LLP

(57) ABSTRACT

The invention relates to compounds of formula (I)

and salts thereof as further defined herein, wherein ring Z is a 6-membered heterocyclic ring containing 1 to 3 nitrogen atoms, and the use of such compounds and salts to inhibit the effects of VEGF and FGF, and in the treatment of a number of disease states including cancer and rheumatoid arthritis.

23 Claims, No Drawings

FOREIGN PATENT DOCUMENTS

| | | |
|---|---|---|
| WO 96/40116 | 12/1996 | (WO). |
| WO 96/40648 | 12/1996 | (WO). |
| WO 96/40673 | 12/1996 | (WO). |
| WO 97/02266 | 1/1997 | (WO). |
| WO 97/03069 | 1/1997 | (WO). |
| WO 97/17329 | 5/1997 | (WO). |
| WO 97/22596 | 6/1997 | (WO). |
| WO 97/28161 | 8/1997 | (WO). |
| WO 97/30034 | 8/1997 | (WO). |
| WO 97/30035 | 8/1997 | (WO). |
| WO 97/32856 | 9/1997 | (WO). |
| WO 97/34876 | 9/1997 | (WO). |
| 97/42187 A | 11/1997 | (WO). |
| WO 97/42187 | 11/1997 | (WO). |
| WO 98/02434 | 1/1998 | (WO). |
| WO 98/13350 | 4/1998 | (WO). |
| WO 98/13354 | 4/1998 | (WO). |
| WO 98/23613 | 6/1998 | (WO). |
| WO 98/35958 | 8/1998 | (WO). |
| WO 98/43960 | 10/1998 | (WO). |
| WO 99/06396 | 2/1999 | (WO). |
| WO 99/09016 | 2/1999 | (WO). |
| WO 99/21859 | 5/1999 | (WO). |
| WO 99/24440 | 5/1999 | (WO). |
| WO 99/35132 | 7/1999 | (WO). |
| WO 99/35146 | 7/1999 | (WO). |
| WO 99/55335 | 11/1999 | (WO). |
| WO 99/62890 | 12/1999 | (WO). |
| WO 00/06554 | 2/2000 | (WO). |
| WO 00/09098 | 2/2000 | (WO). |
| WO 00/09495 | 2/2000 | (WO). |

OXINDOLYLQUINAZOLINE DERIVATIVES AS ANGIOGENESIS INHIBITORS

This application is the national phase of international application PCT/GB98/02493 filed Aug. 19, 1998 which designated the U.S.

The present invention relates to heteroaromatic oxindole derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844). Basic FGF (bFGF) is a potent stimulator of angiogenesis (e.g. Hayek et al, 1987, Biochem. Biophys. Res. Commun. 147: 876–880) and raised levels of FGFs have been found in the serum (Fujimoto et al, 1991, Biochem. Biophys. Res. Commun. 180: 386–392) and urine (Nguyen et al, 1993, J. Natl. Cancer. Inst. 85: 241–242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF and FGF, properties of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess higher potency against VEGF receptor tyrosine kinase and against FGF R1 receptor tyrosine kinase than against epidermal growth factor (EGF) receptor tyrosine kinase. Furthermore, compounds of the present invention, possess substantially higher potency against VEGF receptor tyrosine kinase and against FGF R1 receptor tyrosine kinase than against EGF receptor tyrosine kinase. Compounds of the invention which have been tested possess activity against VEGF receptor tyrosine kinase and against FGF R1 receptor tyrosine kinase such that they may be used in an amount sufficient to inhibit VEGF receptor tyrosine kinase and FGF R1 receptor tyrosine kinase whilst demonstrating no significant activity against EGF receptor tyrosine kinase. Thus compounds of the present invention possess good VEGF receptor tyrosine kinase activity and good FGF R1 receptor tyrosine kinase activity. Compounds with both VEGF receptor tyrosine kinase activity and FGF R1 receptor tyrosine kinase activity are believed to be of particular value in the treatment of disease states associated with angiogenesis and/or increased vascular permeability.

According to one aspect of the present invention there are provided compounds of the formula I:

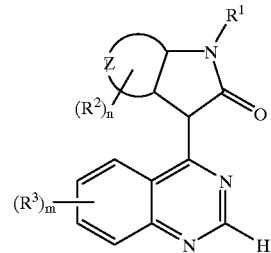

(I)

[wherein:
ring Z is a 5 or 6-membered heterocyclic ring containing 1 to 3 heteroatoms selected independently from O, N and S with the proviso that the group at the 4-position of the quinazoline ring is not a substituted or unsubstituted group selected from 4,5,7-triazaoxindol-3-yl and 4,6,7-triazaoxindol-3-yl;
$R^1$ represents hydrogen, $C_{1-4}$alkyl, $C_{1-4}$alkoxymethyl, di($C_{1-4}$alkoxy)methyl or $C_{1-4}$alkanoyl;
$R^2$ represents hydroxy, halogeno, $C_{1-3}$alkyl, $C_{1-3}$alkoxy, $C_{1-3}$alkanoyloxy, trifluoromethyl, 2,2,2-trifluoroethyl, cyano, amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, N-$C_{1-4}$ alkylcarbarnoyl, N,N-di($C_{1-4}$alkyl)carbamoyl, aminosulphonyl, N-$C_{1-4}$alkylaminosulphonyl, N,N-di($C_{1-4}$alkyl)aminosulphonyl or $C_{1-4}$alkylsulphonylamino or $R^2$ is selected from one of the following four groups:

1) $R^4X^1$ wherein $X^1$ represents a direct bond, —O—, —$NR^5$—, $C_{1-3}$alkyl, $C_{2-4}$alkanoyl, —$CONR^6R^7$—, —$SO_2NR^8R^9$— or —$SO_2R^{10}$— (wherein $R^5$, $R^6$ and $R^8$, each independently represents hydrogen or $C_{1-2}$alkyl and $R^7$, $R^9$ and $R^{10}$ each independently represents $C_{1-4}$alkyl and wherein $R^4$ is linked to $R^7$, $R^9$ or $R^{10}$) and $R^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;

2) $X^2C_{2-4}$alkyl$X^3C_{1-3}$alkyl (wherein $X^2$ is —O— or —$NR^{11}$— (wherein $R^{11}$ is hydrogen, $C_{1-3}$alkyl or $C_{1-3}$alkoxy$C_{2-3}$alkyl) and $X^3$ is —O—, —$NR^{12}$—, —S—, —SO— or —$SO_2$— (wherein $R^{12}$ is hydrogen, $C_{1-3}$alkyl or $C_{1-3}$alkoxy$C_{2-3}$alkyl);

3) $C_{1-2}$alkyl$X^4C_{2-3}$alkyl$X^5C_{1-3}$alkyl (wherein $X^4$ and $X^5$ which may be the same or different are each —O—, —S—, —SO—, —$SO_2$— or —$NR^{13}$— (wherein $R^{13}$ is hydrogen, $C_{1-3}$alkyl or $C_{1-3}$alkoxy$C_{2-3}$alkyl); and 4) $C_{1-3}$alkyl$X^6C_{1-3}$alkyl (wherein $X^6$ is —O—, —S—, —SO—, —$SO_2$— or —$NR^{14}$— (wherein $R^{14}$ is hydrogen, $C_{1-3}$alkyl or $C_{1-3}$alkoxy$C_{2-3}$alkyl);

n is an integer from 0 to 3 when Z is a 6-membered heterocyclic ring and n is an integer from 0 to 2 when Z is a 5-membered heterocyclic ring;

m is an integer from 0 to 4; and $R^3$ represents hydroxy, halogeno, nitro, trifluoromethyl, $C_{1-3}$alkyl, cyano, amino or $R^{15}X^7$ (wherein $X^7$ represents a direct bond, —O—, —$CH_2$—, —S—, —SO—, —$SO_2$—, —$NR^{16}CO$—, —$CONR^{17}$—, —$SO_2NR^{18}$—, —$NR^{19}SO_2$— or —$NR^{20}$— (wherein $R^{16}$, $R^{17}$, $R^{18}$, $R^{19}$ and $R^{20}$ each independently represents hydrogen, $C_{1-3}$alkyl or $C_{1-3}$alkoxy$C_{2-3}$alkyl), and $R^{15}$ is selected from one of the following seventeen groups:

1) hydrogen or $C_{1-5}$alkyl which may be unsubstituted or which may be substituted with one or more groups selected from hydroxy, fluoro and amino;

2) $C_{1-5}$alkyl$X^8COR^{21}$ (wherein $X^8$ represents —O— or —$NR^{22}$— (in which $R^{22}$ represents hydrogen, $C_{1-3}$alkyl or $C_{1-3}$alkoxy$C_{2-3}$alkyl) and $R^{21}$ represents $C_{1-3}$alkyl, —$NR^{23}R^{24}$— or —$OR^{25}$— (wherein $R^{23}$, $R^{24}$ and $R^{25}$ which may be the same or different each represents hydrogen, $C_{1-3}$alkyl or $C_{1-3}$alkoxy$C_{2-3}$alkyl));

3) $C_{1-5}$alkyl$X^9R^{26}$ (wherein $X^9$ represents —O—, —S—, —SO—, —$SO_2$—, —OCO—, —$NR^{27}CO$—, —$CONR^{28}$—, —$SO_2NR^{29}$—, —$NR^{30}SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen, $C_{1-3}$alkyl, cyclopentyl, cyclohexyl or a 5 or 6-membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^{10}C_{1-5}$alkyl$X^{11}R^{32}$ (wherein $X^{10}$ and $X^{11}$ which may be the same or different are each —O—, —S—, —SO—, —$SO_2$—, —$NR^{33}CO$—, —$CONR^{34}$—, —$SO_2NR^{35}$—, —$NR^{36}SO_2$— or —$NR^{37}$— (wherein $R^{33}$, $R^{34}$, $R^{35}$, $R^{36}$ and $R^{37}$ each independently represents hydrogen, $C_{1-3}$alkyl or $C_{1-3}$alkoxy$C_{2-3}$alkyl) and $R^{32}$ represents hydrogen or $C_{1-3}$alkyl);

5) $R^{38}$ (wherein $R^{38}$ is a 5 or 6-membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $C_{1-5}$alkyl$R^{38}$ (wherein $R^{38}$ is as defined hereinbefore);

7) $C_{2-5}$alkenyl$R^{38}$ (wherein $R^{38}$ is as defined hereinbefore);

8) $C_{2-5}$alkynyl$R^{38}$ (wherein $R^{38}$ is as defined hereinbefore);

9) $R^{39}$ (wherein $R^{39}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from hydroxy halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{40}R^{41}$ and —$NR^{42}COR^{43}$— (wherein $R^{40}$, $R^{41}$, $R^{42}$ and $R^{43}$, which may be the same or different, each represents hydrogen, $C_{1-4}$alkyl or $C_{1-3}$alkoxy$C_{2-3}$alkyl));

10) $C_{1-5}$alkyl$R^{39}$ (wherein $R^{39}$ is as defined hereinbefore);

11) $C_{2-5}$alkenyl$R^{39}$ (wherein $R^{39}$ is as defined hereinbefore);

12) $C_{2-5}$alkynyl$R^{39}$ (wherein $R^{39}$ is as defined hereinbefore);

13) $C_{1-5}$alkyl$X^{12}R^{39}$ (wherein $X^{12}$ represents —O—, —S—, —SO—, —$SO_2$—, —$NR^{44}CO$—, —$CONR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{39}$ is as defined hereinbefore);

14) $C_{2-5}$alkenyl$X^{13}R^{39}$ (wherein $X^{13}$ represents —O—, —S—, —SO—, —$SO_2$—, —$NR^{49}CO$—, —$CONR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{39}$ is as defined hereinbefore);

15) $C_{2-5}$alkynyl$X^{14}R^{39}$ (wherein $X^{14}$ represents —O—, —S—, —SO—, —$SO_2$—, —$NR_4CO$—, —$CONR^{55}$—, —$SO_2NR^{56}$—, —$NR^{57}SO_2$— or —$NR^{58}$— (wherein $R^{54}$, $R^{55}$, $R^{56}$, $R^{57}$ and $R^{58}$ each independently represents hydrogen, $C_{1-3}$alkyl or $C_{1-3}$alkoxy$C_{2-3}$alkyl) and $R^{39}$ is as defined hereinbefore);

16) $C_{1-3}$alkyl$X^{15}C_{1-3}$alkyl$R^{39}$ (wherein $X^{15}$ represents —O—, —S—, —SO—, —$SO_2$—, —$NR^{59}CO$—, —$CONR^{60}$—, —$SO_2NR^{61}$—, —NR $SO_2$— or —$NR^{63}$— (wherein $R^{59}$, $R^{60}$, $R^{61}$, $R^{62}$ and $R^{63}$ each independently represents hydrogen, $C_{1-3}$alkyl or $C_{1-3}$alkoxy$C_{2-3}$alkyl) and $R^{39}$ is as defined hereinbefore; and 17) $C_{1-3}$alkyl$X^{15}C_{1-3}$alkyl$R^{38}$ (wherein $X^{15}$ and $R^{38}$ are as defined hereinbefore))];

and salts thereof.

According to another aspect of the present invention there are provided compounds of the formula I wherein:

$R^1$, $R^2$, $R^3$, in and n are as defined hereinbefore; and ring Z is a 6-membered heterocyclic ring containing 1 to 3 nitrogen atoms with the proviso that the group at the 4-position of the quinazoline ring is not a substituted or unsubstituted group selected from 4,5,7-triazaoxindol-3-yl and 4,6,7-triazaoxindol-3-yl;

and salts thereof.

According to another aspect of the present invention there are provided compounds of the formula I wherein:

$R^1$, $R^2$, $R^3$, in and n are as defined hereinbefore; and ring Z is a 6-membered heterocyclic ring containing 1 or 2 nitrogen atoms; with the proviso that where $R^2$ is a group $R^4X^1$, $X^1$ is not $C_{2-4}$alkanoyl or —$SO_2R^{10}$— and $R^4$ is not optionally substituted phenyl or an optionally substituted 5or 6-membered unsaturated heterocyclic ring;
and salts thereof.

Advantageously ring Z is a 6-membered aromatic heterocyclic ring containing 1 to 3 nitrogen atoms with the proviso that the group at the 4-position of the quinazoline ring is not a substituted or unsubstituted group selected from 4,5,7-triazaoxindol-3-yl and 4,6,7-triazaoxindol-3-yl, or Z is a 5-membered aromatic heterocyclic ring containing 1 to 3 heteroatoms selected independently from O, N and S.

Preferably Z is a 6-membered aromatic heterocyclic ring containing 1 to 3 nitrogen atoms with the proviso that the group at the 4-position of the quinazoline ring is not a substituted or unsubstituted group selected from 4,5,7-triazaoxindol-3-yl and 4,6,7-triazaoxindol-3-yl. More preferably Z is a 6-membered aromatic heterocyclic ring containing 1 or 2 nitrogen atoms.

In a particular aspect of the present invention Z is a 6-membered aromatic heterocyclic ring containing 1 or 2 nitrogen atoms such that the substituent at the 4-position of the quinazoline ring is selected from the groups 7-azaoxindol-3-yl and 5,7-diazaoxindol-3-yl, which group bears $(R^2)_n$ as defined hereinbefore.

Conveniently $R^2$ represents hydroxy, halogeno, $C_{1-3}$alkyl, $C_{1-2}$alkoxy, trifluoromethyl, 2,2,2-trifluoroethyl, cyano, nitro, $C_{2-3}$alkanoyl, $C_{1-3}$alkanoylamino, $C_{1-3}$alkoxycarbonyl, $C_{1-3}$alkylthio, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or $R^2$ is selected from one of the following four groups:

1) $R^4X^1$ wherein $X^1$ represents —O—, —$NR^5$—, $C_{1-3}$alkyl, —$CONR^6R^7$— or —$SO_2NR^8R^9$— (wherein $R^5$, $R^6$ and $R^8$, each independently represents hydrogen or $C_{1-2}$alkyl and $R^7$ and $R^9$ each independently represents $C_{1-3}$alkyl and wherein $R^4$ is linked to $R^7$ or $R^9$) and $R^4$ represents a 5 or 6-membered heterocyclic group with one or two heteroatoms, selected independently from O, S, and N, which heterocyclic group may be saturated or unsaturated and which heterocyclic group may bear one or two substituents selected from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl and which heterocyclic group may bear one or two oxo substituents on a ring nitrogen or ring sulphur heteroatom;

2) $X^2C_{2-4}$alkyl$X^3C_{1-3}$alkyl (wherein $X^2$ is —O— or —$NR^{11}$— (wherein $R^{11}$ is hydrogen, $C_{1-2}$alkyl or $C_{1-2}$alkoxyethyl) and $X^3$ is —O—, —$NR^{12}$— or —$SO_2$— (wherein $R^{12}$ is hydrogen, $C_{1-2}$alkyl or $C_{1-2}$alkoxyethyl);

3) $C_{1-2}$alkyl$X^4C_{2-3}$alkyl$X^5C_{1-3}$alkyl (wherein $X^4$ and $X^5$ which may be the same or different are each —O—, —$NR^{13}$— or —$SO_2$— (wherein $R^{13}$ is hydrogen, $C_{1-2}$alkyl or $C_{1-2}$alkoxyethyl); and 4) $C_{1-3}$alkyl$X^6C_{1-3}$alkyl (wherein $X^6$ is —O—, —$NR^{14}$— or —$SO_2$— (wherein $R^{14}$ is hydrogen, $C_{1-2}$alkyl or $C_{1-2}$alkoxyethyl).

Advantageously $R^2$ represents hydroxy, halogeno, $C_{1-3}$alkyl, $C_{1-2}$alkoxy, trifluoromethyl, 2,2,2-trifluoroethyl, cyano, nitro, $C_{2-3}$alkanoyl, $C_{1-3}$alkanoylamino, $C_{1-3}$alkoxycarbonyl, $C_{1-3}$alkylthio, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or $R^2$ is selected from one of the following four groups:

1) $R^4X^1$ wherein $X^1$ represents —O—, —$NR^5$—, $C_{1-3}$alkyl, —$CONR^6R^7$— or —$SO_2NR^8R^9$— (wherein $R^5$, $R^6$ and $R^8$, each independently represents hydrogen or $C_{1-2}$alkyl and $R^7$ and $R^9$ each independently represents $C_{1-3}$alkyl and wherein $R^4$ is linked to $R^7$ or $R^9$) and $R^4$ represents a 5 or 6-membered heterocyclic group with one or two heteroatoms, selected independently from O, S and N, which heterocyclic group may be saturated or unsaturated and which heterocyclic group may bear two oxo substituents on a ring sulphur heteroatom;

2) $X^2C_{2-4}$alkyl$X^3C_{1-3}$alkyl (wherein $X^2$ is —O— or —$NR^{11}$— (wherein $R^{11}$ is hydrogen or $C_{1-2}$alkyl) and $X^3$ is —O—, —$NR^{12}$— or —$SO^2$— (wherein $R^{12}$ is hydrogen or $C_{1-2}$alkyl);

3) $C^{1-2}$alkyl$X^4C_{2-3}$alkyl$X^5C_{1-3}$alkyl (wherein $X^4$ and $X^5$ which may be the same or different are each —$NR^{13}$— or —$SO_2$— (wherein $R^{13}$ is hydrogen or $C_{1-2}$alkyl); and 4) $C_{1-3}$alkyl$X^6C_{1-3}$alkyl (wherein $X^6$ is —O—, —$NR^{14}$— or —$SO_2$— (wherein $R^{14}$ is hydrogen or $C_{1-2}$alkyl).

Preferably $R^2$ represents halogeno, $C_{1-3}$alkyl, $C_{1-2}$alkoxy, trifluoromethyl, 2,2,2-trifluoroethyl, cyano, nitro, $C_{1-3}$alkanoyamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or $R^2$ is selected from one of the following four groups:

1) $R^4X^1$ wherein $X^1$ represents —O—, —$NR^5$—, $C_{1-3}$alkyl, —$CONR^6R^7$— or —$SO_2NR^8R^9$— (wherein $R^5$, $R^6$ and $R^8$, each independently represents hydrogen or $C_{1-2}$alkyl and $R^7$ and $R^9$ each independently represents $C_{1-3}$alkyl and wherein $R^4$ is linked to $R^7$ or $R^9$) and $R^4$ represents a 5 or 6-membered saturated heterocyclic group with one or two heteroatoms, selected independently from O, S and N, which heterocyclic group may bear two oxo substituents on a ring sulphur heteroatom;

2) $X^2C_{2-4}$alkyl$X^3C_{1-3}$alkyl (wherein $X^2$ is —O— or —$NR^{11}$— (wherein $R^{11}$ is hydrogen or $C_{1-2}$alkyl) and $X^3$ is —O—, —$NR^{12}$— or —$SO_2$— (wherein $R^{12}$ is hydrogen or $C_{1-2}$alkyl);

3) $C_{1-2}$alkyl$X^4C_{2-3}$alkyl$X^5C_{1-3}$alkyl (wherein $X^4$ and Xs which may be the same or different are each —$NR^{13}$— or —$SO_2$— (wherein $R^{13}$ is hydrogen or $C_{1-2}$alkyl); and 4) $C_{1-3}$alkyl$X^6C_{1-3}$alkyl (wherein $X^6$ is —O—, —$NR^{14}$— or —$SO_2$— (wherein $R^{14}$ is hydrogen or $C_{1-2}$alkyl).

More preferably $R^2$ represents halogeno, $C_{1-2}$alkyl, $C_{1-2}$alkoxy, trifluoromethyl, 2,2,2-trifluoroethyl, cyano, nitro, $C_{1-3}$alkanoylamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or $R^2$ is selected from one of the following four groups:

1) $R^4X^1$ wherein $X^1$ represents —O—, —$NR^5$—, $C_{1-3}$alkyl, —$CONR^6R^7$— or —$SO_2NR^8R^9$— (wherein $R^5$, $R^6$, and $R^8$, each independently represents hydrogen or $C_{1-2}$alkyl and $R^7$ and $R^9$ each independently represents $C_{1-3}$alkyl and wherein R is linked to $R^7$ or $R^9$) and $R^4$ represents a 5 or 6-membered saturated heterocyclic group with one or two heteroatoms, selected independently from O, S and N, which heterocyclic group may bear two oxo substituents on a ring sulphur heteroatom;

2) $X^2C_{2-3}$alkyl$X^3$methyl (wherein $X^2$ is —O— or —$NR^{11}$— (wherein $R^{11}$ is hydrogen or $C_{1-2}$alkyl) and $X^3$ is —O—, —$NR^{12}$— or —$SO_2$— (wherein $R^{12}$ is hydrogen or $C_{12}$alkyl);

3) $C_{1-2}$alkyl$X^4C^{2-3}$alkyl$X^5$methyl (wherein $X^4$ and X5 which may be the same or different are each —$NR^{13}$— or —$SO_2$— (wherein $R^{12}$ is hydrogen or $C_{1-2}$alkyl); and 4) $C_{1-2}$alkyl$X^6C_{1-2}$alkyl (wherein $X^6$ is —O—, —NR$^{14}$— or —SO$_2$— (wherein R$^{14}$ is hydrogen or $C_{1-2}$alkyl).

Especially R$^2$ represents halogeno, $C_{1-2}$alkyl, $C_{1-2}$alkoxy, trifluoromethyl, 2,2,2-trifluoroethyl, cyano, nitro, $C_{1-3}$alkanoylamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino.

More especially R$^2$ represents halogeno, trifluoromethyl, 2,2,2-trifluoroethyl, cyano, nitro, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl or N,N-di($C_{1-3}$alkyl)aminosulphonyl.

In a particular aspect of the present invention when Z is a 6-membered aromatic heterocyclic ring containing 1 to 3 nitrogen atoms, with the proviso that the group at the 4-position of the quinazoline ring is not a substituted or unsubstituted group selected from 4,5,7-triazaoxindol-3-yl and 4,6,7-triazaoxindol-3-yl, R$^2$ is not attached at the 4-position of the heteroaromatic oxindole ring unless R$^2$ is fluoro.

In a further particular aspect of the present invention when Z is a 6-membered aromatic heterocyclic ring containing 1 to 3 nitrogen atoms, with the proviso that the group at the 4-position of the quinazoline ring is not a substituted or unsubstituted group selected from 4,5,7-triazaoxindol-3-yl and 4,6,7-triazaoxindol-3-yl, R$^2$ is attached at the 5- and/or 6-positions of the heteroaromatic oxindole ring, but if R$^2$ is fluoro it can be attached at the 4-, 5-, 6- or 7-position(s) of the heteroaromatic oxindole ring.

In another particular aspect of the present invention when Z is a 6-membered aromatic heterocyclic ring containing 1 or 2 nitrogen atoms R is attached at the 5- and/or 6-positions of the heteroaromatic oxindole ring, but if R$^2$ is fluoro it can be attached at the 4-, 5-, 6- or 7-position(s) of the heteroaromatic oxindole ring.

Preferably n is an integer from 0 to 2.

Preferably R$^1$ represents hydrogen, $C_{1-4}$alkoxymethyl, di($C_{1-4}$alkoxy)methyl or $C_{1-4}$alkanoyl, especially hydrogen.

Preferably m is an integer from 0 to 2, most preferably 1 to 2.

Advantageously X$^7$ represents —O—, —S—, —NR$^{16}$CO—, —NR$^{19}$SO$_2$— or —NR$^{20}$— (wherein R$^{16}$, R$^{19}$ and R$^{20}$ each independently represents hydrogen, $C_{1-2}$alkyl or $C_{1-2}$alkoxyethyl).

Preferably X7 represents —O—, —S—, —NR$_6$CO—, —NR$^{19}$SO$_2$— (wherein R$^{16}$ and R$^{19}$ each independently represents hydrogen or $C_{1-2}$alkyl) or NH.

More preferably X$^7$ represents —O—, —S—, —NR$^{16}$CO— (wherein R$^{16}$ represents hydrogen or $C_{1-2}$alkyl) or NH.

Particularly X$^7$ represents —O— or —NR$^{16}$CO— (wherein R$^{16}$ represents hydrogen or $C_{1-2}$alkyl), more particularly —O— or —NHCO—, especially —O—.

Advantageously X$^8$ represents —O— or —NR$^{22}$— (wherein R$^{22}$ represents hydrogen, $C_{1-3}$alkyl or $C_{1-2}$alkoxyethyl).

Advantageously X$^9$ represents —O—, —S—, —SO—, —SO$_2$—, —NR$^{27}$CO—, —NR$^{30}$SO$_2$— or —NR$^{31}$— (wherein R$^{27}$, R$^{30}$ and R$^{31}$ each independently represents hydrogen, $C_{1-2}$alkyl or $C_{1-2}$alkoxyethyl).

Preferably X$^9$ represents —O—, —S—, —SO—, —SO$_2$— or —NR$^{31}$— (wherein R$^{31}$ represents hydrogen, $C_{1-2}$alkyl or $C_{1-2}$alkoxyethyl).

More preferably X$^9$ represents —O—, —SO$_2$— or —NR$^{31}$— (wherein R$^{31}$ represents hydrogen or $C_{1-2}$alkyl).

Advantageously X$^{10}$ and X$^{11}$ which may be the same or different each represents —O—, —S—, —SO—, —SO$_2$— or —NR$^{37}$— (wherein R$^{37}$ represents hydrogen, $C_{1-3}$alkyl or $C_{1-2}$alkoxyethyl).

Preferably X$^{10}$ and X$^{11}$ which may be the same or different each represents —O—, —S—, —SO$_2$— or —NR$^{37}$— (wherein R$^{37}$ represents hydrogen, $C_{1-2}$alkyl or $C_{1-2}$alkoxyethyl).

More preferably X$^{10}$ and X$^{11}$ which may be the same or different each represents —O—, —SO$_2$— or —NH—.

Advantageously X$^{12}$ represents —O—, —S—, —SO$_2$— or —NR$^{48}$— (wherein R$^{48}$ represents hydrogen, $C_{1-2}$alkyl or $C_{1-2}$alkoxyethyl).

Preferably X$^{12}$ represents —O—, —SO$_2$— or —NR$^{48}$— (wherein R$^{48}$ represents hydrogen or $C_{1-2}$alkyl).

Advantageously X$^{13}$ represents —O—, —S—, —SO$_2$— or —NR$^{53}$— (wherein R$^{53}$ represents hydrogen, $C_{1-2}$alkyl or $C_{1-2}$alkoxyethyl).

Preferably X$^{13}$ represents —O—, —SO$_2$— or —NR$^{53}$— (wherein R$^{53}$ represents hydrogen or $C_{1-2}$alkyl).

Advantageously X$^{14}$ represents —O—, —S—, —SO$_2$— or —NR$^{58}$— (wherein R$^{58}$ represents hydrogen, $C_{1-2}$alkyl or $C_{1-2}$alkoxyethyl).

Preferably X$^{14}$ represents —O—, —SO$_2$— or —NR$_{58}$— (wherein R$^{58}$ represents hydrogen or $C_{1-2}$alkyl).

Advantageously X$^{15}$ represents —O—, —S—, —SO$_2$— or —NR$^{63}$— (wherein R$^{63}$ represents hydrogen, $C_{1-2}$alkyl or $C_{1-2}$alkoxyethyl).

Preferably X$^{15}$ represents —O—, —SO$_2$— or —NR$^{63}$— (wherein R$^{63}$ represents hydrogen or $C_{1-2}$alkyl).

R$^{38}$ is preferably pyrrolidinyl, piperazinyl, piperidinyl, morpholino or thiomorpholino which group may carry one or two substituents selected from oxo, hydroxy, halogeno, $C_{1-2}$alkyl, $C_{1-2}$hydroxyalkyl and $C_{1-2}$alkoxy.

More preferably R$^{38}$ is pyrrolidinyl, piperazinyl, piperidinyl, morpholino, thiomorpholino, 1-methylpiperazinyl or 1-ethylpiperazinyl which group may carry one or two oxo substituents.

R$^{39}$ preferably represents a pyridone group or a 5 or 6-membered aromatic heterocyclic group with 1 to 3 heteroatoms selected from O, N and S, which pyridone group or heterocyclic group may be substituted as hereinbefore defined.

Where R$^{39}$ is a 5 or 6-membered aromatic heterocyclic group, it preferably has 1 or 2 heteroatoms, selected from O, N and S, of which more preferably one is N, and may be substituted as hereinbefore defined.

R$^{39}$ is particularly a pyridone, pyridyl, imidazolyl, thiazolyl, thienyl, triazolyl, pyridazinyl, pyrazinyl or pyrimidinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined. In one embodiment of the invention R$^{39}$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of R$^{39}$, conveniently substituents are selected from halogeno, $C_{1-4}$alkyl, $C_{1-4}$alkoxy, trifluoromethyl and cyano, more conveniently substituents are selected from chloro, fluoro, methyl, ethyl and trifluoromethyl.

Conveniently R$^3$ represents hydroxy, halogeno, nitro, trifluoromethyl, $C_{1-3}$alkyl, cyano, amino or R$^{15}$X$^7$ [wherein X$^7$ is as hereinbefore defined and R$^{15}$ is selected from one of the following seventeen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkyl$X^8COR^{21}$ (wherein $X^8$ is as hereinbefore defined and $R^{21}$ represents $C_{1-3}$alkyl, —$NR^{23}R^{24}$— or —$OR^{25}$— (wherein $R^{23}$, $R^{24}$ and $R^{25}$ which may be the same or different are each $C_{1-2}$alkyl or $C_{1-2}$alkoxyethyl));
3) $C_{2-4}$alkyl$X^9R^{26}$ (wherein $X^9$ is as hereinbefore defined and $R^{26}$ represents hydrogen, $C_{1-3}$alkyl, cyclopentyl, cyclohexyl or a 5 or 6-membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{2-3}$akyl$X^{10}C_{2-3}$alkyl$X^{11}R^{32}$ (wherein $X^{10}$ and $X^{11}$ are as hereinbefore defined and $R^{32}$ represents hydrogen or $C_{1-3}$alkyl);
5) $R^{38}$ (wherein $R^{38}$ is as defined hereinbefore);
6) $C_{1-4}$alkyl$R^{64}$ (wherein $R^{64}$ is a 5 or 6-membered saturated heterocyclic group with one or two heteroatoms, selected independently from O, S and N, which heterocyclic group is linked to $C_{1-4}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{2-5}$alkyl$R^{65}$ (wherein $R^{65}$ is a 5 or 6-membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);
7) $C_{3-4}$alkenyl$R^{66}$ (wherein $R^{66}$ represents $R^{64}$ or $R^{65}$ as defined hereinbefore);
8) $C_{3-4}$alkynyl$R^{66}$ (wherein $R^{66}$ represents $R^{64}$ or $R^{65}$ as defined hereinbefore);
9) $R^{39}$ (wherein $R^{39}$ is as defined hereinbefore);
10) $C_{1-4}$alkyl$R^{39}$ (wherein $R^{39}$ is as defined hereinbefore);
11) $C_{3-4}$alkenyl$R^{39}$ (wherein $R^{39}$ is as defined hereinbefore);
12) $C_{3-4}$alkynyl$R^{39}$ (wherein $R^{39}$ is as defined hereinbefore);
13) $C_{2-4}$alkyl$X^{12}R^{39}$ (wherein $X^{12}$ and $R^{39}$ are as defined hereinbefore);
14) $C_{4-5}$alkenyl$X^{13}R^{39}$ (wherein $X^{13}$ and $R^{39}$ are as defined hereinbefore);
15) $C_{4-5}$alkynyl$X^{14}R^{39}$ (wherein $X^{14}$ and $R^{39}$ are as defined hereinbefore); and
16) $C_{2-3}$alkyl$X^{15}C_{1-2}$alkyl$R^{39}$ (wherein $X^{15}$ and $R^{39}$ are as defined hereinbefore); and
17) $C_{2-3}$alkyl$X^{15}C_{1-2}$alkyl$R^{38}$ (wherein $X^{15}$ and $R^{38}$ are as defined hereinbefore)].

Advantageously $R^3$ represents hydroxy, halogeno, nitro, trifluoromethyl, $C_{1-3}$alkyl, cyano, amino or $R^{15}X^7$ [wherein $X^7$ is as hereinbefore defined and $R^{15}$ is selected from one of the following seventeen groups:
1) $C_{1-4}$alkyl which may be unsubstituted or substituted with one or more fluorine atoms, or $C_{2-4}$alkyl which may be unsubstituted or substituted with one or two groups selected from hydroxy and amino;
2) $C_{2-3}$alkyl$X^8COR^{21}$ (wherein $X^8$ is as hereinbefore defined and $R^{21}$ represents —$NR^{23}R^{24}$— or —$OR_5$— (wherein $R_2$, $R^{24}$ and $R_{25}$ which may be the same or different are each $C_{1-2}$alkyl or $C_{1-2}$alkoxyethyl));
3) $C_{2-4}$alkyl$X^9R^{26}$ (wherein $X^9$ is as hereinbefore defined and $R^{26}$ is a group selected from $C_{1-3}$alkyl, cyclopentyl, cyclohexyl, pyrrolidinyl and piperidinyl which group is linked to $X^9$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^{10}C_{2-3}$alkyl$X^{11}R^{32}$ (wherein $X^{10}$ and $X^{11}$ are as hereinbefore defined and $R^{32}$ represents hydrogen or $C_{1-3}$alkyl);
5) $R^{38}$ (wherein $R^{38}$ is as defined hereinbefore);
6) $C_{1-4}$alkyl$R^{67}$ (wherein $R^{67}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{68}$ (wherein $R^{68}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);
7) $C_{3-4}$alkenyl$R^{69}$ (wherein $R^{69}$ represents $R^{67}$ or $R^{68}$ as defined hereinbefore);
8) $C_{3-4}$alkynyl$R^{69}$ (wherein $R^{69}$ represents $R^{67}$ or $R^{68}$ as defined hereinbefore);
9) $R^{39}$ (wherein $R^{39}$ is as defined hereinbefore);
10) $C_{14}$alkyl$R^{39}$ (wherein $R^{39}$ is as defined hereinbefore);
11) 1-$R^{39}$prop-1-en-3-yl or 1-$R^{39}$but-2-en-4-yl (wherein $R^{39}$ is as defined hereinbefore with the proviso that when $R^{15}$ is 1-$R^{39}$prop-1-en-3-yl, $R^{39}$ is linked to the alkenyl group via a carbon atom);
12) 1-$R^{39}$prop-1-en-3-yl or 1-$R^{39}$but-2-en-4-yl (wherein $R^{39}$ is as defined hereinbefore with the proviso that when $R^{15}$ is 1-$R^{39}$prop-1-en-3-yl, $R^{39}$ is linked to the alkynyl group via a carbon atom);
13) $C_{2-4}$alkyl$X^{12}R^{39}$ (wherein $X^{12}$ and $R^{39}$ are as defined hereinbefore);
14) 1-($R^{39}X^{13}$)but-2-en-4-yl (wherein $X^{13}$ and $R^{39}$ are as defined hereinbefore);
15) 1-($R^{39}X^{14}$)but-2-yn-4-yl (wherein $X^{14}$ and $R^{39}$ are as defined hereinbefore);
16) $C_{2-3}$alkyl$X^{15}C_{1-2}$alkyl$R^{39}$ (wherein $X^{15}$ and $R^{39}$ are as defined hereinbefore); and
17) $C_{2-3}$alkyl$X^{15}C_{1-2}$alkyl$^{38}$ (wherein $X^{15}$ and $R^{38}$ are as defined hereinbefore)].

Preferably $R^3$ represents hydroxy, halogeno, nitro, trifluoromethyl, $C_{1-3}$alkyl, cyano, amino or $R^{15}X^7$ [wherein $X^7$ is as hereinbefore defined and $R^{15}$ is selected from one of the following fifteen groups:
1) $C_{1-3}$alkyl which may be unsubstituted or substituted with one or more fluorine atoms, or $C_{2-3}$alkyl which may be unsubstituted or substituted with one or two groups selected from hydroxy and amino;
2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(-methylcarbamoyloxy)ethyl, 3-(N-methylcarbamoyloxy)propyl, 2-(carbamoyloxy)ethyl, 3-(carbamoyloxy)propyl;
3) $C_{2-3}$alkyl$X^9R^{26}$ (wherein $X^9$ is as defined hereinbefore and $R^{26}$ is a group selected from $C_{1-2}$alkyl, cyclopentyl, cyclohexyl, pyrrolidinyl and piperidinyl which group is linked to $X^9$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^{10}C_{2-3}$alkyl$X^{11}R^{32}$ (wherein $X^{10}$ and $X^{11}$ are as hereinbefore defined and $R^{32}$ represents hydrogen or $C_{1-2}$alkyl);
5) $R^{38}$ (wherein $R^{38}$ is as defined hereinbefore);
6) $C_{1-2}$alkyl$R^{67}$ (wherein $R^{67}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{68}$ (wherein $R^{68}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);
7) $R^{39}$ (wherein $R^{39}$ is as defined hereinbefore);
8) $C_{1-4}$alkyl$R^{39}$ (wherein $R^{39}$ is as defined hereinbefore);
9) 1-$R^{39}$but-2-en4-yl (wherein $R^{39}$ is as defined hereinbefore);
10) 1-$R^{39}$but-2-en-4-yl (wherein $R^{39}$ is as defined hereinbefore);
11) $C_{2-4}$alkyl$X^{12}R^{39}$ (wherein $X^{12}$ and $R^{39}$ are as defined hereinbefore);
12) 1-($R^{39}X^{13}$)but-2-en4-yl (wherein $X^{13}$ and $R^{39}$ are as defined hereinbefore);
13) 1-($R^{39}X^4$)but-2-en-4-yl (wherein $X^{14}$ and $R^{39}$ are as defined hereinbefore);
14) ethyl$X^{15}$methyl$R^{39}$ (wherein $X^{15}$ and $R^{39}$ are as defined hereinbefore); and
15) ethyl$X^{15}$methyl$R^{38}$ (wherein $X^{15}$ and $R^{38}$ are as defined hereinbefore)].

More preferably $R^3$ represents hydroxy, $C_{1-3}$alkyl, amino or $R^{15}X^7$ [wherein $X^7$ is as hereinbefore defined and $R^{15}$ represents 2-methylthiazol-4-ylmethyl, 2-acetamidothiazol-4-ylmethyl, 1-methylimidazol-2-ylmethyl, 4-pyridylmethyl, 2-(4-pyridyl)ethyl, 3-(4-pyridyl)propyl, 2-((N-(1-methylimidazol-4-ylsulphonyl)-N-methyl)amino)ethyl, 2-((N-(3-morpholinopropylsulphonyl)-N-methyl)amino) ethyl, 2-((N-methyl-N-4-pyridyl)amino)ethyl, 2-(4-oxidomorpholino)ethyl, 3-(4-oxidomorpholino)propyl, 2-(4-oxo-1,4-dihydro-1-pyridyl)ethyl, 3-(4-oxo-1,4-dihydro-1-pyridyl)propyl, methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(²-methoxyethylamino)propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl) ethyl, 3-(5-methyl-1,2,4-triazol-1-yl)propyl, morpholino, N-methylpiperazinyl, piperazinyl, 2-(N,N-dimethylamino) ethyl, 3-(N,N-dimethylamnino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy) ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl].

Especially $R^3$ represents hydroxy, $C_{1-3}$alkyl, amino or $R^{15}X^7$ [wherein $X^7$ is as hereinbefore defined and $R^{15}$ represents methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-(1,2,4-triazol-1-yl)ethyl, 2-(1,2,4-triazol-4-yl) ethyl, 3-(1,2,4-triazol-1-yl)propyl, 3-(1,2,4-triazol-4-yl) propyl, 2-(4-pyridyloxy)ethyl, 3-(4-pyridyloxy)propyl, 2-(4-pyridylamino)ethyl, 3-(4-pyridylamino)propyl, 2-(2-methylirnidazol-1-yl)ethyl, 3-(2-methylimidazol-1-yl) propyl, 2-(5-methyl-1,2,4-triazol-1-yl)ethyl, 3-(5-methyl-1, 2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(irnidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1, 2,3-triazol-2-yl)propyl, 2-thiomorpholinoethyl, 3-thiomorpholinopropyl, 2-(1,1-dioxothiomorpholino)ethyl, 3-(l, 1-dioxothiomorpholino)propyl, 2-(2-methoxyethoxy) ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl. More especially $R^3$ represents hydroxy, $C_{1-3}$alkyl, amino or $R^{15}X^7$ [wherein $X^7$ is as hereinbefore defined and $R^{15}$ represents 2-N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl) propyl, 2-methoxyethyl, 3-methoxypropyl, 2-(imidazol-1-yl)ethyl, 2-(1,2,3 -triazol-1-yl)ethyl, 2-(1,2,3-triazol-2-yl) ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy) ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl.

Where one of the $R^3$ substituents is $R^{15}X^7$ the substituent $R^{15}X^7$ is preferably at the 6 or 7-position of the quinazoline ring, more preferably at the 7-position of the quinazoline ring. In a particular aspect of the current invention there are provided compounds of the formula Ia:

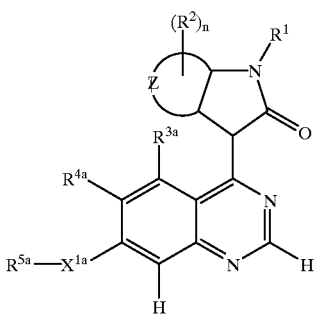

(Ia)

[wherein:
$R^1$, $R^2$, ring Z and n are as defined hereinbefore;
$R^{3a}$ represents hydrogen, hydroxy, methoxy, amino, nitro or halogeno;
$R^{4a}$ represents hydrogen, hydroxy, halogeno, cyano, nitro, trifluoromethyl, $C_{1-3}$alkyl, $C_{1-3}$alkoxy, $C_{1-3}$alkylthio, —$NR^{6a}R^{7a}$ (wherein $R^{6a}$ and $R^{7a}$, which may be the same or different, each represents hydrogen or $C_{1-3}$alkyl), or a group $R^{8a}(CH_2)_{ta}X^{2a}$, (wherein $R^{8a}$ is a 5 or 6-membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, ta is an integer from 0 to 4 and $X^{2a}$ represents a direct bond, —O—, —$CH_2$—, —S—, —SO—, —$SO_2$—, —$NR^{9a}CO$—, —$CONR^{10a}$—, —$SO_2NR^{11a}$—, $NR^{12a}SO_2$— or $NR^{13a}$— (wherein $R^{9a}$, $R^{10a}$, $R^{11a}$, $R^{12a}$ and $R^{13a}$ each independently represents hydrogen, $C_{1-3}$alkyl or $C_{1-3}$alkoxyC$_{2-3}$alkyl));
$X^{1a}$ represents a direct bond, —O—, —$CH_2$—, —S—, —SO—, —$SO_2$—, —$NR^{14a}CO$—, —$CONR^{15a}$—, —$SO_2NR^{16a}$, $NR^{17a}SO_2$— or —$NR^{18a}$— (wherein $R^{14a}$, $R^{15a}$, $R^{16a}$, $R^{17a}$ and $R^{18a}$ each independently represents hydrogen, $C_{1-3}$alkyl or $C_{1-3}$alkoxyC$_{2-3}$alkyl);
$R^{5a}$ is selected from one of the following seventeen groups:
1) hydrogen or $C_{1-5}$alkyl which may be unsubstituted or which may be substituted with one or more groups selected from hydroxy, fluoro and amino;
2) $C_{1-5}$alkylX$^{3a}$COR$^{19a}$ (wherein $X^{3a}$ represents —O— or —$NR^{20a}$— (in which $R^{20a}$ represents hydrogen, $C_{1-3}$ alkyl or $C_{1-3}$ alkoxyC$_{2-3}$alkyl) and $R^{19a}$ represents $C_{1-3}$alkyl, —$NR^{21a}R^{22a}$— or —$OR^{23a}$— (wherein $R^{21a}$, $R^{22a}$ and $R^{23a}$ which may be the same or different each represents hydrogen, $C_{1-3}$alkyl or $C_{1-3}$alkoxyC$_{2-3}$alkyl));
3) $C_{1-5}$alkylX$^{4a}$R$^{24a}$ (wherein $X^{4a}$ represents —O—, —S—, —SO—, —$SO_2$—, —OCO—, —$NR^{25a}CO$—, —$CONR^{26a}$—, —$SO_2NR^{27a}$—, —$NR^{28a}SO_2$— or —$NR^{29a}$— (wherein $R^{25a}$, $R^{26a}$, $R^{27a}$, $R^{28a}$ and $R^{29a}$ each independently represents hydrogen, $C_{1-3}$alkyl or $C_{1-3}$alkoxyC$_{2-3}$alkyl) and $R^{24a}$ represents hydrogen, $C_{1-3}$alkyl, cyclopentyl, cyclohexyl or a 5 or 6-membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkylX$^{5a}$C$_{1-5}$alkylX$^{6a}$R$^{30a}$ (wherein $X^{5a}$ and $X^{6a}$ which may be the same or different are each —O—, —S—, —SO—, —$SO_2$—, —$NR^{31a}CO$—, —$CONR^{32a}$—, —$SO_2NR^{33a}$—, —$NR^{34a}SO_2$— or —$NR^{35a}$— (wherein $R^{31a}$, $R^{32a}$, $R^{33a}$, $R^{34a}$ and $R^{35a}$ each independently represents hydrogen, $C_{1-3}$alkyl or $C_{1-3}$alkoxyC$_{2-3}$alkyl) and $R^{30a}$ represents hydrogen or $C_{1-3}$alkyl);
5) $R^{36a}$ (wherein $R^{36a}$ is a 5 or 6-membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $C_{1-5}$alkylR$^{36a}$ (wherein $R^{36a}$ is as defined hereinbefore);
7) $C_{2-5}$alkenylR$^{36a}$ (wherein $R^{36a}$ is as defined hereinbefore);
8) $C_{2-5}$alkynylR$^{36a}$ (wherein $R^{36a}$ is as defined hereinbefore);
9) $R^{37a}$ (wherein $R^{37a}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, Ci4alkylamino, $C_{1-4}$hydroxyalkoxy, carboxy, trifluoromethyl, cyano, —$CONR^{38a}R^{39a}$ and —$NR^{40a}COR^{41a}$— (wherein $R^{38a}$, $R^{39a}$, $R^{40a}$ and $R^{41a}$, which may be the same or different, each represents hydrogen, $C_{1-4}$alkyl or $C_{1-3}$alkoxyC$_{2-3}$alkyl));
10) $C_{1-5}$alkylR$^{37a}$ (wherein $R^{37a}$ is as defined hereinbefore);
11) $C_{2-5}$alkenylR$^{37a}$ (wherein $R^{37a}$ is as defined hereinbefore);
12) $C_{2-5}$alkynylR$^{37a}$ (wherein $R^{37a}$ is as defined hereinbefore);
13) $C_{1-5}$alkylX$^{7a}$R$^{37a}$ (wherein $X^{7a}$ represents —O—, —S—, —SO—, —$SO_2$—, —$NR^{42a}CO$—, —$CONR^{43a}$—, —$SO_2NR^{44a}$—, —$NR^{45a}SO_2$— or —$NR^{46a}$— (wherein $R^{42a}$, $R^{43a}$, $R^{44a}$, $R^{45a}$ and $R^{46a}$ each independently represents hydrogen, $C_{1-3}$alkyl or $C_{1-3}$alkoxyC$_{2-3}$alkyl) and $R^{37a}$ is as defined hereinbefore);
14) $C_{2-5}$alkenylX$^{8a}$R$^{37a}$ (wherein $X^{8a}$ represents —O—, —S—, —SO—, —$SO^2$—, —$NR^{47a}CO$—, —$CONR^{48a}$—, —$SO_2NR^{49a}$—, —$NR^{50a}SO_2$— or —$NR^{51a}$— (wherein $R^{47a}$, $R^{48a}$, $R^{49a}$, $R^{50a}$ and $R^{51a}$ each independently represents hydrogen, $C_{1-3}$alkyl or $C_{1-3}$alkoxyC$_{2-3}$alkyl) and $R^{37a}$ is as defined hereinbefore);
15) $C_{2-5}$alkynylX$^{9a}$R$^{37a}$ (wherein $X^{9a}$ represents —O—, —S—, —SO—, —$SO_2$—, —$NR^{52a}CO$—, —$CONR^{53a}$—, —$SO_2NR^{54a}$—, —$NR^{55a}SO_2$— or —$NR^{56a}$— (wherein $R^{52a}$, $R^{53a}$, $R^{54a}$, $R^{55a}$ and $R^{56a}$ each independently represents hydrogen, $C_{1-3}$alkyl or $C_{1-3}$alkoxyC$_{2-3}$alkyl) and $R^{37a}$ is as defined hereinbefore);
16) $C_{1-3}$alkylX$^{10a}$C$_{1-3}$alkylR$^{37a}$ (wherein $X^{10a}$ represents —O—, —S—, —SO—, —$SO_2$—, —$NR^{57a}CO$—, —$CONR^{58a}$—, —$SO_2NR^{59a}$—, —$NR^{60a}SO_2$— or —$NR^{60a}$— (wherein $R^{57a}$, $R^{58a}$, $R^{59a}$, $R^{60a}$ and $R^{61a}$ each independently represents hydrogen, $C_{1-3}$alkyl or $C_{1-3}$alkoxyC$_{2-3}$alkyl) and $R^{37a}$ is as defined hereinbefore); and
17) $C_{1-3}$alkylX$^{10a}$C$_{1-3}$alkylR$^{36a}$ (wherein $X^{10a}$ and $R^{36a}$ are as defined hereinbefore)];
and salts thereof.

Preferably $R^{3a}$ represents hydrogen, amino, nitro or halogeno, but especially hydrogen. Advantageously $X^{2a}$ represents —O—, —S—, —$NR^{9a}CO$—, —$NR^{12a}SO_2$— or —$NR^{13a}$— (wherein $R^{9a}$, $R^{12a}$ and $R^{13a}$ each independently represents hydrogen, $C_{1-2}$alkyl or $C_{1-2}$alkoxyethyl).

Preferably $X^{2a}$ represents —O—, —S—, —NR$^{9a}$CO—, —NR$^{12a}$SO$_2$— (wherein R$^{9a}$ and R$^{12a}$ each independently represents hydrogen or $C_{1-2}$alkyl) or NH.
More preferably X2a represents —O—, —S—, —NR$^{9a}$CO— (wherein R$^{9a}$ represents hydrogen or $C_{1-2}$alkyl) or NH.
Particularly $X^{2a}$ represents —O— or —NR$^{9a}$CO— (wherein R$^{9a}$ represents hydrogen or $C_{1-2}$alkyl), more particularly —O— or —NHCO—, especially —O—.
Preferably ta is an integer from 1 to 3.
Preferably R$^{8a}$ is a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy.
Advantageously R$^{4a}$ represents hydrogen, hydroxy, cyano, nitro, trifluoromethyl, $C_{1-3}$alkyl, $C_{1-3}$alkoxy, amino or a group R$^{8a}$(CH$_2$)$_{ta}$X$^{2a}$ (wherein R$^{8a}$, X$^{2a}$ and ta are as defined hereinbefore). Preferably R$^{4a}$ is hydrogen, hydroxy, cyano, nitro, trifluoromethyl, methyl, ethyl, methoxy, ethoxy or a group R$^{8a}$(CH$_2$)$_{ta}$X$^{2a}$ (wherein R$^{8a}$, X$^{2a}$ and ta are as defined hereinbefore).
More preferably R$^{4a}$ is hydrogen, hydroxy, cyano, nitro, trifluoromethyl, methyl, ethyl, methoxy, ethoxy or R$^{8a}$(CH$_2$)$_{ta}$X$^{2a}$ (wherein R$^{8a}$ is a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, $X_{2a}$ is —O—, —S—, —NR$^{9a}$CO—, —NR$^{12a}$SO$_2$— (wherein R$^{9a}$ and R$^{12a}$ each independently represents hydrogen or $C_{1-2}$alkyl) or NH and ta is an integer from 1 to 3).
Particularly R$^{4a}$ represents hydrogen, hydroxy, cyano, nitro, trifluoromethyl, methyl, methoxy or R$^{8a}$(CH$_2$)$_{ta}$X$^{2a}$ (wherein R$^{8a}$, X$^{2a}$ and ta are as defined hereinbefore).
More particularly R$^{4a}$ represents hydrogen or methoxy.
R$^{4a}$ especially represents methoxy.
Advantageously $X^{1a}$ represents —O—, —S—, —NR$^{14a}$CO—, —NR$^{17a}$SO$_2$— or —NR$^{18a}$— (wherein R$^{14a}$, R$^{17a}$ and R$^{18a}$ each independently represents hydrogen, $C_{1-2}$alkyl or $C_{1-2}$alkoxyethyl).
Preferably $X^{1a}$ represents —O—, —S—, —NR$^{14a}$CO—, —NR$^{17a}$SO$_2$— (wherein R$^{14a}$ and R$^{17a}$ each independently represents hydrogen or $C_{1-2}$alkyl) or NH.
More preferably $X^{1a}$ represents —O—, —S—, —NR$^{14a}$CO— (wherein R$^{14a}$ represents hydrogen or $C_{1-2}$alkyl) or NH.
Particularly $X^{1a}$ represents —O— or —NR$^{14a}$CO— (wherein R$^{14a}$ represents hydrogen or $C_{1-2}$alkyl), more particularly —O— or —NHCO—, especially —O—.
Advantageously $X^{3a}$ represents —O— or NR$^{20a}$ (wherein R$^{20a}$ represents hydrogen, $C_{1-3}$alkyl or $C_{1-2}$alkoxyethyl).
Advantageously $X^{4a}$ represents —O—, —S—, —SO—, —SO$_2$—, —NR$^{25a}$CO—, —NR$^{28a}$SO$_2$— or —NR$^{29a}$— (wherein R$^{25a}$, R$^{28a}$ and R$^{29a}$ each independently represents hydrogen, $C_{1-2}$alkyl or $C_{1-2}$alkoxyethyl).
Preferably $X^{4a}$ represents —O—, —S—, —SO—, —SO$_2$— or —NR$^{29a}$— (wherein R$^{29a}$ represents hydrogen, $C_{12}$alkyl or $C_{12}$alkoxyethyl).
More preferably $X^{4a}$ represents —O—, —SO$_2$— or —NR$^{29a}$— (wherein R$^{29a}$ represents hydrogen or $C_{1-2}$alkyl).
Advantageously $X^{5a}$ and $X^{6a}$ which may be the same or different each represents —O—, —S—, —SO—, —SO$_2$— or —NR$^{35a}$— (wherein R$^{35a}$ represents hydrogen, $C_{1-3}$alkyl or $C_{1-2}$alkoxyethyl).
Preferably $X^{5a}$ and $X^{6a}$ which may be the same or different each represents —O—, —S—, —SO$_2$— or —NR$^{35a}$— (wherein R$^{35a}$ represents hydrogen, $C_{1-2}$alkyl or $C_{1-2}$alkoxyethyl).
More preferably $X^{5a}$ and $X^{6a}$ which may be the same or different each represents —O—, —SO$_2$— or —NH—.
Advantageously $X^{7a}$ represents —O—, —S—, —SO$_2$— or —NR$^{46a}$— (wherein R$^{46a}$ represents hydrogen, $C_{1-2}$alkyl or $C_{1-2}$alkoxyethyl).
Preferably $X^{7a}$ represents —O—, —SO$_2$— or —NR$^{46a}$— (wherein R$^{46a}$ represents hydrogen or $C_{1-2}$alkyl).
Advantageously $X^{8a}$ represents —O—, —S—, —SO$_2$— or —NR$^{51a}$— (wherein R$^{51s}$ represents hydrogen, $C_{1-2}$alkyl or $C_{1-2}$alkoxyethyl).
Preferably $X^{8a}$ represents —O—, —SO$_2$— or —NR$^{51a}$— (wherein R$^{51a}$ represents hydrogen or $C_{1-2}$alkyl).
Advantageously $X^{9a}$ represents —O—, —S—, —SO$_2$— or —NR$^{56a}$— (wherein R$^{56a}$ represents hydrogen, $C_{1-2}$alkyl or $C_{1-2}$alkoxyethyl).
Preferably $X^{9a}$ represents —O—, —SO$_2$— or —NR$^{56a}$— (wherein R$^{56a}$ represents hydrogen or $C_{1-2}$alkyl).
Advantageously $X^{10a}$ represents —O—, —S—, —SO$_2$— or —NR$^{61a}$— (wherein R$^{61a}$ represents hydrogen, $C_{1-2}$alkyl or $C_{1-2}$alkoxyethyl).
Preferably $X^{10a}$ represents —O—, —SO$_2$— or —NR$^{61a}$— (wherein R$^{61a}$ represents hydrogen or $C_{1-2}$alkyl).
R$^{36a}$ is preferably pyrrolidinyl, piperazinyl, piperidinyl, morpholino or thiomorpholino which group may carry one or two substituents selected from oxo, hydroxy, halogeno, $C_{1-2}$alkyl, $C_{1-2}$hydroxyalkyl and $C_{1-2}$alkoxy.
More preferably R$^{36a}$ is pyrrolidinyl, piperazinyl, piperidinyl, morpholino, thiomorpholino, 1-methylpiperazinyl or 1-ethylpiperazinyl which group may carry one or two oxo substituents. R$^{37a}$ preferably represents a pyridone group or a 5 or 6-membered aromatic heterocyclic group with 1 to 3 heteroatoms selected from O, N and S, which pyridone group or heterocyclic group may be substituted as hereinbefore defined.
Where R$^{37a}$ is a 5 or 6-membered aromatic heterocyclic group, it preferably has 1 or 2 heteroatoms, selected from O, N and S, of which more preferably one is N, and may be substituted as hereinbefore defined.
R$^{37a}$ is particularly a pyridone, pyridyl, imidazolyl, thiazolyl, thienyl, triazolyl, pyridazinyl or pyrazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined. In one embodiment of the invention R$^{37a}$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.
In the definition of R$^{37a}$, conveniently substituents are selected from halogeno, $C_{1-4}$alkyl, $C_{1-4}$alkoxy, trifluoromethyl and cyano, more conveniently substituents are selected from chloro, fluoro, methyl, ethyl and trifluoromethyl.
Conveniently R$^{5a}$ is selected from one of the following seventeen groups:
1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkylX$^{3a}$COR$^{19a}$ (wherein X$^{3a}$ is as hereinbefore defined and R$^{19a}$ represents $C_{1-3}$alkyl, —NR$^{21a}$R$^{22a}$— or —OR$^{23a}$— (wherein R$^{21a}$, R$^{22a}$ and R$^{23a}$ which may be the same or different are each $C_{1-2}$alkyl or $C_{1-2}$alkoxyethyl));

3) $C_{2-4}$alkyl$X^{4a}R^{24a}$ (wherein $X^{4a}$ is as hereinbefore defined and $R^{24a}$ represents hydrogen, $C_{1-3}$alkyl, cyclopentyl, cyclohexyl or a 5 or 6-membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{2-3}$alkyl$X^{5a}C_{2-3}$alkyl$X^{6a}R^{30a}$ (wherein $X^{5a}$ and $X^{6a}$ are as hereinbefore defined and $R^{30a}$ represents hydrogen or $C_{1-3}$alkyl);

5) $R^{36a}$ (wherein $R^{36a}$ is as defined hereinbefore);

6) $C_{1-4}$alkyl$R^{36a}$ (wherein $R^{62a}$ is a 5 or 6-membered saturated heterocyclic group with one or two heteroatoms, selected independently from O, S and N, which heterocyclic group is linked to $C_{1-4}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{2-5}$alkyl$R^{63a}$ (wherein $R^{63a}$ is a 5 or 6-membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);

7) $C_{3-4}$alkenyl$R^{64a}$ (wherein $R^{64a}$ represents $R^{62a}$ or $R^{63a}$ as defined hereinbefore);

8) $C_{3-4}$alkynyl$R^{64a}$ (wherein $R^{64a}$ represents $R^{62a}$ or $R^{63a}$ as defined hereinbefore);

9) $R^{37a}$ (wherein $R^{37a}$ is as defined hereinbefore);

10) $C_{1-4}$alkyl$R^{37a}$ (wherein $R^{37a}$ is as defined hereinbefore);

11) $C_{3-4}$alkenyl$R^{37a}$ (wherein $R^{37a}$ is as defined hereinbefore);

12) $C_{3-4}$alkenyl$R^{37a}$ (wherein $R^{37a}$ is as defined hereinbefore);

13) $C_{2-4}$alkyl$X^{7a}X^{37a}$ (wherein $X^{7a}$ and $R^{37a}$ are as defined hereinbefore);

14) $C_{4-5}$alkenyl$X^{8a}R^{37a}$ (wherein $X^{8a}$ and $R^{37a}$ are as defined hereinbefore);

15) $C_{4-5}$alkynyl$X^{9a}R^{37a}$ (wherein $X^{9a}$ and $R^{37a}$ are as defined hereinbefore);

16) $C_{2-3}$alkyl$X^{10a}C_{1-2}$alkyl$R^{37a}$ (wherein $X^{10a}$ and $R^{37a}$ are as defined hereinbefore); and 17) $C_{2-3}$alkyl$X^{10a}C_{1-2}$alkyl$R^{36a}$ (wherein $X^{10a}$ and $R^{36a}$ are as defined hereinbefore).

Advantageously $R^{5a}$ is selected from one of the following seventeen groups:

1) $C_{1-4}$alkyl which may be unsubstituted or substituted with one or more fluorine atoms, or $C_{2-4}$alkyl which may be unsubstituted or substituted with one or two groups selected from hydroxy and amino;

2) $C_{2-3}$alkyl$X^{3a}COR^{19a}$ (wherein $X^{3a}$ is as hereinbefore defined and $R^{19a}$ represents —$NR^{21a}R^{22a}$— or —$OR^{23a}$— (wherein $R^{21a}$, $R^{22a}$ and $R^{23a}$ which may be the same or different are each $C_{1-2}$alkyl or $C_{1-2}$alkoxyethyl));

3) $C_{2-4}$alkyl$X^{4a}R^{24a}$ (wherein $X^{4a}$ is as hereinbefore defined and $R^{24a}$ is a group selected from $C_{1-3}$alkyl, cyclopentyl, cyclohexyl, pyrrolidinyl and piperidinyl which group is linked to $X^{4a}$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{5a}C_{2-3}$alkyl$X^{6a}R^{30a}$ (wherein $X^{5a}$ and $X^{6a}$ are as hereinbefore defined and $R^{30a}$ represents hydrogen or $C_{1-3}$alkyl);

5) $R^{36a}$ (wherein $R^{36a}$ is as defined hereinbefore);

6) $C_{1-4}$alkyl$R^{65a}$ wherein $R^{65a}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{66a}$ (wherein $R^{66a}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);

7) $C_{3-4}$alkenyl$R^{67a}$ (wherein $R^{67a}$ represents $R^{65a}$ or $R^{66a}$ as defined hereinbefore);

8) $C_{3-4}$alkynyl$R^{67a}$ (wherein $R^{67a}$ represents $R^{65a}$ or $R^{66a}$ as defined hereinbefore);

9) $R^{37a}$ (wherein $R^{37a}$ is as defined hereinbefore);

10) $R^{37a}$ (wherein $R^{37a}$ is as defined hereinbefore);

11) 1-$R^{37a}$prop-1-en-3-yl or 1-$R^{37a}$but-2-en-4-yl (wherein $R^{37a}$ is as defined hereinbefore with the proviso that when $R^{5a}$ is 1-$R^{37a}$prop-1-en-3-yl, $R^{37a}$ is linked to the alkenyl group via a carbon atom);

12) 1-$R^{37a}$prop-1-yn-3-yl or 1-$R^{37a}$but-2-yn-4-yl (wherein $R^{37a}$ is as defined hereinbefore with the proviso that when $R^{5a}$ is 1-$R^{37a}$prop-1-yn-3-yl, $R^{37a}$ is linked to the alkynyl group via a carbon atom);

13) $C_{2-4}$alkyl$X^{7a}R^{37a}$ (wherein $X^{7a}$ and $R^{37a}$ are as defined hereinbefore);

14) 1-($R^{37a}X^{8a}$)but-2-en-4-yl (wherein $X^{8a}$ and $R^{37a}$ are as defined hereinbefore);

15) 1-($R^{37a}X^{9a}$)but-2-yn-4-yl (wherein $X^{9a}$ and $R^{37a}$ are as defined hereinbefore);

16) $C_{2-3}$alkyl$X^{10a}C_{1-2}$alkyl$R^{37a}$ (wherein $X^{10a}$ and $R^{37a}$ are as defined hereinbefore); and 17) $C_{2-3}$alkyl$X^{10a}C_{1-2}$alkyl$R^{36a}$ (wherein $X^{10a}$ and $R^{36a}$ are as defined hereinbefore).

Preferably $R^{5a}$ is selected from one of the following fifteen groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^{4a}R^{24a}$ (wherein $X^{4a}$ is as defined hereinbefore and $R^{24a}$ is a group selected from $C_{1-2}$alkyl, cyclopentyl, cyclohexyl, pyrrolidinyl and piperidinyl which group is linked to $X^{4a}$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{5a}C_{2-3}$alkyl$X^{6a}R^{30a}$ (wherein $X^{5a}$ and $X^{6a}$ are as hereinbefore defined and $R^{30a}$ represents hydrogen or $C_{1-2}$alkyl);

5) $R^{36a}$ (wherein $R^{36a}$ is as defined hereinbefore);

6) $C_{1-4}$alkyl$R^{65a}$ (wherein $R^{65a}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{66a}$ (wherein $R^{66a}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);

7) $R^{37a}$ (wherein $R^{37a}$ is as defined hereinbefore);

8) $C_{1-4}$alkyl$R^{37a}$ (wherein $R^{37a}$ is as defined hereinbefore);

9) 1-$R^{37a}$but-2-en-4-yl (wherein $R^{37a}$ is as defined hereinbefore);

10) 1-$R^{37a}$but-2-yn-4-yl (wherein $R^{37a}$ is as defined hereinbefore);

11) $C_{2-4}$alkyl$X^{7a}R^{37a}$ (wherein $X^{7a}$ and $R^{37a}$ are as defined hereinbefore);

12) 1-($R^{37a}X^{8a}$)but-2-en-4-yl (wherein $X^{8a}$ and $R^{37a}$ are as defined hereinbefore);

13) 1-($R^{37a}X^{9a}$)but-2-yn-4-yl (wherein $X^{9a}$ and $R^{37a}$ are as defined hereinbefore);

14) ethyl$X^{10a}$methyl$R^{37a}$ (wherein $X^{10a}$ and $R^{37a}$ are as defined hereinbefore); and 15) ethyl$X^{10a}$methyl$R^{36a}$ (wherein $X^{10a}$ and $R^{36a}$ are as defined hereinbefore).

More preferably $R^{5a}$ represents 2-methylthiazol-4-ylmethyl, 2-acetamidothiazol-4-ylmethyl, 1-methylimidazol-2-ylmethyl, 4-pyridylmethyl, 2-(4-pyridyl)ethyl, 3-(4-pyridyl)propyl, 2-((N-(1-methylimidazol-4-ylsulphonyl)-N-methyl)amino)ethyl, 2-((N-(3-morpholinopropylsulphonyl)-N-methyl)amino)ethyl, 2-((1N-methyl-N-4-pyridyl)amino)ethyl, 2-(4-oxidomorpholino)ethyl, 3-(4-oxidomorpholino)propyl, 2-(4-oxo-1,4-dihydro-1-pyridyl)ethyl, 3-(4-oxo-1,4-dihydro-l-pyridyl)propyl, methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl.

Especially $R^{5a}$ represents methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl.

More especially $R^{5a}$ 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl.

In a further aspect of the current invention there are provided compounds of the formula Ib:

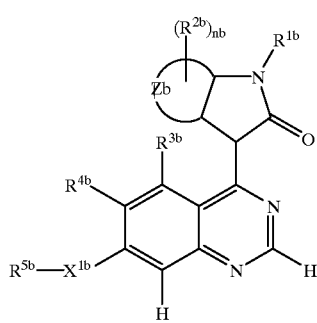

(Ib)

[wherein:

$R^{1b}$ represents hydrogen;

$R^{2b}$ represents halogeno, $C_{1-2}$alkyl, $C_{1-2}$alkoxy, trifluoromethyl, 2,2,2-trifluoroethyl, cyano, nitro, $C_{1-3}$alkanoylamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or $R^{2b}$ is selected from one of the following four groups:

1) $R^{6b}X^{2b}$ wherein $X^{2b}$ represents —O—, —NR$^{7b}$—, $C_{1-3}$alkyl, -CONR$^{8b}$R$^{9b}$— or —SO$_2$NR$^{10b}$R$^{11b}$— (wherein $R^{7b}$, $R^{8b}$, and $R^{10b}$, each independently represents hydrogen or $C_{1-2}$alkyl and $R^{9b}$ and $R^{11b}$ each independently represents $C_{1-3}$alkyl and wherein $R^{6b}$ is linked to $R^{9b}$ or $R^{11b}$) and $R^{6b}$ represents a 5 or 6-membered saturated heterocyclic group with one or two heteroatoms, selected independently from O, S and N, which heterocyclic group may bear two oxo substituents on a ring sulphur heteroatom;

2) $X^{3b}C_{2-3}$alkyl$X^{4b}$methyl (wherein $X^{3b}$ is —O— or —NR$^{12b}$— (wherein $R^{12b}$ is hydrogen or $C_{1-2}$alkyl) and $X^{4b}$ is —O—, —NR$^{13b}$— or —SO$_2$— (wherein $R^{13b}$ is hydrogen or $C_{1-2}$alkyl);

3) $C_{1-2}$alkyl$X^{5b}C_{2-3}$ alkyl$X^{6b}$ methyl (wherein $X^{5b}$ and $X^{6b}$ which may be the same or different are each —NR$^{14b}$— or —SO$_2$— (wherein $R^{14b}$ is hydrogen or $C_{1-2}$alkyl); and 4) $C_{1-2}$alkyl$X^{7b}C_{1-2}$alkyl (wherein $X^{7b}$ is —O—, —NR$^{15b}$— or —SO$_2$— (wherein $R^{15b}$ is hydrogen or $C_{1-2}$alkyl);

nb is an integer from 0 to 2;

ring Zb is a 6-membered aromatic heterocyclic ring containing 1 or 2 nitrogen atoms such that the substituent at the 4-position of the quinazoline ring is selected from the groups 7-azaoxindol-3-yl and 5,7-diazaoxindol-3-yl which group bears $(R^{2b})_{nb}$ as defined hereinbefore;

$R^{2b}$ is attached at the 5- and/or 6-positions of the heteroaromatic oxindole ring, but if $R^{2b}$ is fluoro it can be attached at the 4-, 5-, 6- or 7-position(s) of the heteroaromatic oxindole ring;

$R^{3b}$ represents hydrogen;

$R^{4b}$ represents hydrogen, hydroxy, cyano, nitro, trifluoromethyl, methyl, methoxy or a group $R^{16b}(CH_2)_{tb}X^{8b}$ (wherein $R^{16b}$ represents a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, tb is an integer from 1 to 3 and $X^{8b}$ represents —O—, —S—, —NR$^{17b}$CO—, —NR$^{17b}$SO$_2$— (wherein $R^{17b}$ and $R^{18b}$ each independently represents hydrogen or $C_{1-2}$alkyl) or NH);

$X^{1b}$ represents —O— or —NR$^{19b}$CO— (wherein $R^{19b}$ represents hydrogen or $C_{1-2}$alkyl); and $R^{5b}$ represents methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl) ethyl, (1,3-dioxolan-2-yl)methyl, 2-(1,3-dioxolan-2-yl) ethyl, 2-(2-methoxyethylamino)ethyl, 2-(2-hydroxyethylamino)ethyl, 3-(2-methoxyethylamino) propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy) ethyl, 3-(4-pyridyloxy)propyl, 2-(4-pyridylamino)ethyl, 3-(4-pyridylamino)propyl, 2-(2-methylimidazol-1-yl) ethyl, 3-(2-methylimidazol-1-yl)propyl, 2-(5-methyl-1,2, 4-triazol-1-yl)ethyl, 3-(5-methyl-1,2,4-triazol-1-yl) propyl, morpholino, N-methylpiperazinyl, piperazinyl, 2-(N,N-dimethylamino)ethyl, 3-(N,N-dimethylamino) propyl, 2-morpholinoethyl, 3-morpholinopropyl, 2-piperidinoethyl, 3-piperidinopropyl, 2-(piperazin-1-yl) ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino) ethyl, -3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl) propyl, 3-(methylsulphonyl )propyl, 2-(methylsulphinyl) ethyl or 2-(methylsulphonyl )ethyl;]

and salts thereof.

Preferred compounds are 4-(7-azaoxindol-3-yl)-7-methoxy-6-(3-morpholinopropoxy) quinazoline, 4-(7-azaoxindol-3-yl)-6-methoxy-7-(2-methoxyethoxy) quinazoline and 4-(7-azaoxindol-3-yl)-6-methoxy-7-(2-(pyrrolidin-1-yl) ethoxy)quinazoline and salts thereof, particularly hydrochloride salts thereof.

More preferred compounds are 4-(7-azaoxindol-3-yl)-6-methoxy-7-(3-morpholinopropoxy) quinazoline, 4-(7-azaoxindol-3-yl)-7-(2-(imidazol-1-yl)ethoxy)-6-methoxyquinazoline, 4-(5,7-diaza-6-methyloxindol-3-yl)-7-(3-morpholinopropoxy)quinazoline and 4-(4-aza-6-trifluoromethyloxindol-3-yl) 6-methoxy-7-(3-morpholinopropoxy)quinazoline and salts thereof, particularly hydrochloride salts thereof.

Additional more preferred compounds are 4-(5,7-diaza-6-methyloxindol-3-yl)-7-(3-(1,1-dioxothiomorpholino)propoxy)quinazoline, 4-(7-aza-6-chlorooxindol-3-yl)-7-(3-morpholinopropoxy) quinazoline, 4-(7-azaoxindol-3-yl)-7-(4-morpholinobut-2-en-1-yloxy) quinazoline and 4-(5,7-diaza-6-methyloxindol-3-yl)-7-(3-methylsulphonylpropoxy)quinazoline and salts thereof, particularly hydrochloride salts thereof.

In a particular aspect of the invention a preferred compound is 4-(5,7-diaza-6-methyloxindol-3-yl)-7-(3-morpholinopropoxy)quinazoline and salts thereof, particularly hydrochloride salts thereof.

In a further particular aspect of the invention preferred compounds are 4-(7-azaoxindol-3-yl)-7-(2-(2-methoxyethoxy)ethoxy) quinazoline and 4-(7azaoxindol-3-yl)-7-(3-morpholinopropoxy)quinazoline and salts thereof, particularly hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl" —O—groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"—O—groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and which inhibits FGF R1 receptor tyrosine kinase activity and is not to be limited merely to any one tautomeric form utilised within the formulae drawings. In particular the heteroaromatic oxindole group can exist in at least two forms giving compounds of formulae I and II:

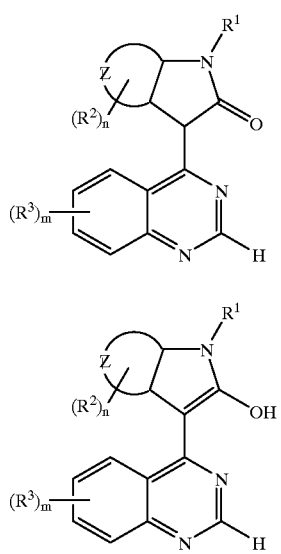

(wherein $R^1$, $R^2$, $R^3$, ring Z, m and n are as hereinbefore defined). The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity and inhibit FGF R1 receptor tyrosine kinase activity.

For the avoidance of any doubt, it is to be understood that when $X^7$ is, for example, a group of formula —$NR^{16}CO$—, it is the nitrogen atom bearing the $R^{16}$ group which is attached to the quinazoline ring and the carbonyl (CO) group is attached to $R^{15}$, whereas when $X^7$ is, for example, a group of formula —$CONR^{17}$—, it is the carbonyl group which is attached to the quinazoline ring and the nitrogen atom bearing the $R^{17}$ group is attached to $R^{15}$. A similar convention applies to the other two atom $X^7$ linking groups such as —$NR^{19}SO_2$— and —$SO_2NR^{18}$—. When $X^7$ is —$NR^{20}$— it is the nitrogen atom bearing the $R^{20}$ group which is linked to the quinazoline ring and to $R^{15}$. An analogous convention applies to other groups. It is further to be understood that when $X^7$ represents —$NR^{20}$— and $R^{20}$ is $C_{1-3}$alkoxy$C_{2-3}$alkyl it is the $C_{2-3}$alkyl moiety which is linked to the nitrogen atom of $X^7$ and an analogous convention applies to other groups.

For the avoidance of any doubt, it is to be understood that in a compound of the formula I when $R^{15}$ is, for example, a group of formula $C_{1-5}$alkyl$X^{15}C_{1-5}$alkyl$R^{39}$, it is the terminal $C_{1-5}$alkyl moiety which is linked to $X^{15}$, similarly when $R^{15}$ is, for example, a group of formula $C_{2-5}$alkenyl$R^{39}$ it is the $C_{2-5}$alkenyl moiety which is linked to $X^7$ and an analogous convention applies to other groups. When $R^{15}$ is a group 1-$R^{39}$prop-1-en-3-yl it is the first carbon to which the group $R^{39}$ is attached and it is the third carbon which is linked to $X^7$ and an analogous convention applies to other groups.

For the avoidance of any doubt, it is to be understood that when $R^{39}$ carries a $C_{1-4}$aminoalkyl substituent it is the $C_{1-4}$alkyl moiety which is attached to $R^{39}$ whereas when $R^{39}$ carries a $C_{1-4}$alkylamino substituent it is the amino moiety which is attached to $R^{39}$ and an analogous convention applies to other groups.

For the avoidance of any doubt when $X^1$ is $C_{2-4}$alkanoyl it is the carbonyl moiety which is linked to the heteroaromatic oxindole group and it is the alkyl moiety which is linked to $R^4$ and an analogous convention applies to other groups.

For the avoidance of any doubt when R is a group $X^2C_{2-4}$alkyl$X^3C_{1-3}$alkyl it is $X^2$ which is linked to the heteroaromatic oxindole group and an analogous convention applies to other groups. When $R^2$ is a group $C_{1-2}$alkyl$X^4C_{2-3}$alkyl$X^5C_{1-3}$alkyl it is the $C_{1-2}$alkyl moiety which is linked to the heteroaromatic oxindole group and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Publication Nos. 0520722, 0566226, 0602851, 0635498 and 0636608. Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (h) and (i) to (viii) constitute further features of the present invention.

Synthesis of Compounds of Formula I (a) Compounds of the formula I and salts thereof may be prepared by the reaction of a compound of the formula III:

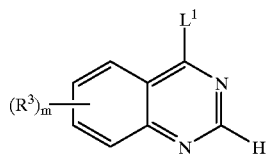

(III)

(wherein $R^3$ and m are as defined hereinbefore and $L^1$ is a displaceable moiety), with a compound of the formula IV:

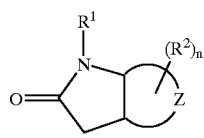

(IV)

(wherein $R^1$, $R^2$ ring Z and n are as defined hereinbefore) whereby to obtain compounds of the formula 1 and salts thereof. A convenient displaceable moiety $L^1$ is, for example, a halogeno, alkoxy (preferably $C_{1-4}$alkoxy), aryloxy, alkylthio, arylthio, alkoxyalkylthio or sulphonyloxy group, for example a chloro, bromo, methoxy, phenoxy, methylthio, 2-methoxyethylthio, methanesulphonyloxy or toluene-4-sulphonyloxy group.

The reaction is advantageously effected in the presence of a base. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 90° C.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) A compound of the formula I and salts thereof can be prepared by the deprotection of a compound of formula V:

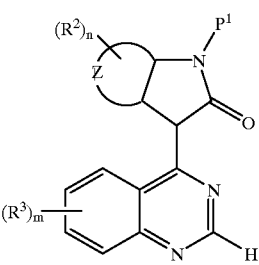

(V)

(wherein $R^2$, $R^3$, n, ring Z and m are as hereinbefore defined and $P^1$ represents a protecting group).

The choice of indole protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and particularly amino acetal derivatives (for example, diethoxymethyl and benzyloxymethyl). The removal of such a protecting group may be effected by any of the procedures known for such a transformation, including those reaction conditions indicated in standard texts such as that indicated hereinbefore, or by a related procedure. For example, where the protecting group $P^1$ is diethoxymethyl, the transformation may conveniently be effected by treatment of the heteroaromatic oxindole derivative with an acid (as defined hereinbefore in process (a)) preferably in the presence of a protic solvent or co-solvent such as water or an alcohol, for example methanol or ethanol. Such a reaction can be effected in the presence of an additional inert solvent or diluent (as defined hereinbefore in process (a)) advantageously at a temperature in the range 0 to 100° C., conveniently in the range 20 to 90° C.

(c) Compounds of the formula I and salts thereof wherein $R^1$ is hydrogen may also be prepared by the reduction and cyclisation of a compound of formula VI:

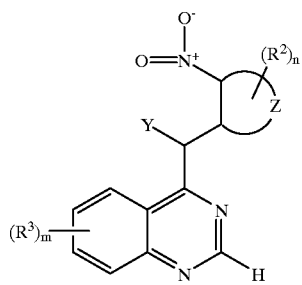

(wherein $R^2$, $R^3$, m, ring Z and n are as defined hereinbefore and Y represents cyano, carboxy or $C_{1-4}$alkoxycarbonyl). The reduction of the nitro group may conveniently be effected as described in process (i) hereinafter. Where Y represents carboxy or $C_{1-4}$alkoxycarbonyl, the cyclisation to a compound of formula I occurs spontaneously after reduction of the nitro group or may be promoted, if necessary, by heating in an inert solvent or diluent such as xylene, toluene or N,N-dimethylformamide, optionally in the presence of an acid (as described hereinbefore in process (a)), advantageously at a temperature in the range of 20 to 150° C. preferably in the range 20 to 100° C. Where Y represents cyano, the cyclisation to a compound of formula I can be effected in the presence of an acid (as described hereinbefore in process (a)) or a Lewis acid, such as a haloborane derivative for example boron trifluoride, and an alcohol or thiol, such as methanol, ethanol or 2-methyl-2-propanethiol, in an inert solvent or diluent (as defined hereinbefore in process (a)) and at a temperature in the range –20 to 50° C. preferably –5 to 10° C., followed by treatment with an aqueous acid, (as defined hereinbefore in process (a)), at a temperature in the range 20 to 150° C. preferably in the range 20 to 100° C.

(d) Compounds of formula I and salts thereof wherein at least one of the $R^2$ groups is hydroxy may also be prepared by the deprotection of a compound of formula VII:

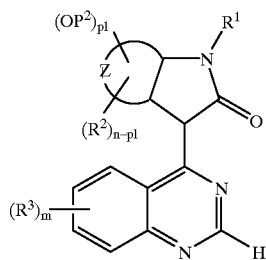

(wherein $R^1$, $R^2$, $R^3$, n, ring Z and m are as defined hereinbefore, $p^2$ represents a phenolic hydroxy protecting group and p1 is an integer from 1 to 3 equal to the number of protected hydroxy groups and such that n–p1 is equal to the number of $R^2$ substituents which are not protected hydroxy). The choice of phenolic hydroxy protecting group $p^2$ is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl, benzyl and benzyl substituted with up to 2 substituents selected from $C_{1-4}$alkoxy and nitro), silyl ethers (for example, t-butyldiphenylsilyl and t-butyldimethylsilyl), esters (for example, acetate and benzoate) and carbonates (for example, methyl, benzyl and benzyl substituted with up to 2 substituents selected from $C_{1-4}$alkoxy and nitro). The removal of such a phenolic hydroxy protecting group may be effected by any of the procedures known for such a transformation, including those reaction conditions indicated in standard texts such as that indicated hereinbefore, or by a related procedure. For example, where the protecting group $p^2$ is benzyl, the transformation may conveniently be effected by treatment of the heteroaromatic oxindole derivative with an acid (as defined hereinbefore in process (a)) particularly trifluoroacetic acid, preferably in the presence of an ether or thioether such as thioanisole. Such a reaction can be effected in the presence of an additional inert solvent or diluent (as defined hereinbefore in process (a)) advantageously at a temperature in the range 0 to 80° C., conveniently at about 40° C.

(e) Production of those compounds of formula I and salts thereof wherein at least one $R^3$ is $R^{15}X^7$ wherein $R^{15}$ is as defined hereinbefore and $X^7$ is —O—, —S—, —SO$_2$—, —CONR$^{17}$—, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxyC$_{2-3}$alkyl) can be achieved by the reaction, conveniently in the presence of a base (as defined hereinbefore in process (a)) of a compound of the formula VIII:

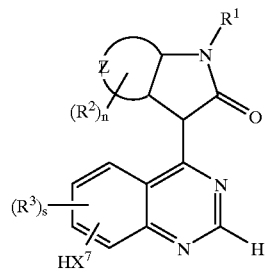

(wherein $R^1$, $R^2$, $R^3$, n, ring Z and $X^7$ are as hereinbefore defined and s is an integer from 0 to 3) with a compound of formula IX:

$$R^{15}—L^1 \quad (IX)$$

(wherein $R^{15}$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for examnple 10 to 150° C., conveniently at about 50° C.

(f) Compounds of the formula I and salts thereof wherein at least one $R^3$ is $R^{15}X^7$ wherein $R^{15}$ is as defined hereinbefore and $X^7$ is —O—, —S—, or —NR$^{20}$— (wherein $R^{20}$ represents hydrogen, $C_{1-3}$alkyl or $C_{1-3}$alkoxyC$_{2-3}$alkyl) may be prepared by the reaction of a compound of the formula X:

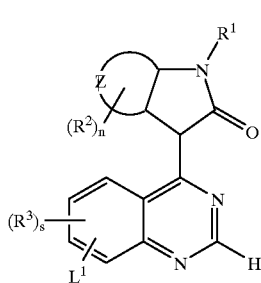

(X)

with a compound of the formula XI:

$$R^{15}-X^7-H \qquad (XI)$$

(wherein $L^1$, $R^1$, $R^2$, $R^3$, $R^{15}$, n, ring Z, s and $X^7$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(g) Compounds of the formula I and salts thereof wherein at least one $R^3$ is $R^{15}X^7$ wherein $X^7$ is as defined hereinbefore and $R^{15}$ is $C_{1-5}$alkyl$R^{70}$, [wherein $R^{70}$ is selected from one of the following six groups:

1) $X^{16}C_{1-3}$alkyl (wherein $X^{16}$ represents —O—, —S—, —SO$_2$—, —NR$^{71}$CO— or —NR$^{72}$SO$_2$— (wherein $R^{71}$ and $R^{72}$ which may be the same or different are each hydrogen, $C_{1-3}$alkyl or $C_{1-3}$alkoxyC$_{2-3}$alkyl);
2) NR$^{73}$R$^{74}$ (wherein $R^{73}$ and $R^{74}$ which may be the same or different are each hydrogen, $C_{1-3}$alkyl or $C_{1-3}$alkoxyC$_{2-3}$alkyl);
3) $X^{17}C_{1-5}$alkyl$X^{11}R^{32}$ (wherein $X^{17}$ represents —O—, —S—, —SO$_2$—, —NR$^{75}$CO—, —NR$^{76}$SO$_2$— or —NR$^{77}$— (wherein $R^{75}$, $R^{76}$, and $R^{77}$ which may be the same or different are each hydrogen, $C_{1-3}$alkyl or $C_{1-3}$alkoxyC$_{2-3}$alkyl) and $X^{11}$ and $R^{32}$ are as defined hereinbefore);
4) $R^{65}$ (wherein $R^{65}$ is as defined hereinbefore);
5) $X^{18}R^{39}$ (wherein $X^{18}$ represents —O—, —S—, —SO$_2$—, —NR$^{78}$CO—, —NR$^{79}$SO$_2$—, or —NR$^{80}$— (wherein $R^{78}$, $R^{79}$, and $R^{80}$ which may be the same or different are each hydrogen, $C_{1-3}$akyl or $C_{1-3}$alkoxyC$_{2-3}$alkyl) and $R^{39}$ is as defined hereinbefore); and
6) $X^{19}C_{1-5}$alkyl$R^{39}$ (wherein $X^{19}$ represents —O—, —S—, —SO$_2$—, —NR$^{81}$CO—, —NR$^{82}$SO$_2$— or —NR$^{83}$— (wherein $R^{81}$, $R^{82}$ and $R^{83}$ each independently represents hydrogen, $C_{1-3}$alkyl or $C_{1-3}$alkoxyC$_{2-3}$alkyl) and $R^{39}$ is as defined hereinbefore);]

may be prepared by reacting a compound of the formula XII:

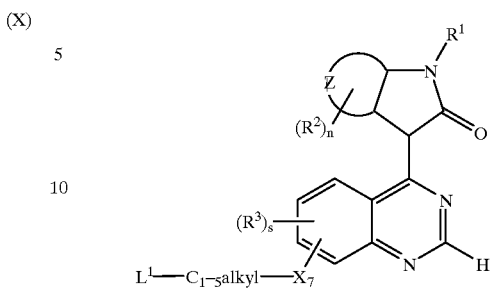

(XII)

(wherein $L^1$, $X^7$, $R^1$, $R^2$, $R^3$, n, ring Z and s are as hereinbefore defined) with a compound of the formula XIII:

$$R^{70}-H \qquad (XMII)$$

(wherein $R^{70}$ is as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a)–(d) are preferred over processes (e)–(g).

(h) The production of those compounds of the formula I and salts thereof wherein one or more of the substituents $(R^3)_m$ is represented by —NR 84R$^{85}$—, where one or both of R$^{84}$ and R$^{85}$ are $C_{1-3}$alkyl, may be effected by the reaction of compounds of formula I wherein the substituent $(R^3)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ or $R^3$ is an amino group may be effected by the reduction of a corresponding compound of formula I wherein the substituent(s) at the corresponding position(s) of the quinazoline and/or heteroaromatic oxindole group is/are a nitro group(s). The reduction may conveniently be effected as described in process (i) hereinafter. The production of a compound of formula I and salts thereof wherein the substituent(s) at the corresponding position(s) of the quinazoline and/or heteroaromatic oxindole group is/are a nitro group(s) may be effected by the processes described hereinbefore and hereinafter in processes (a-g, (preferably a, b or d-g, more preferably a, b or d)) and (i–viii) using a compound selected from the compounds of the formulae (I–XXXIV) in which the substituent (s) at the corresponding position(s) of the quinazoline and/or benz ring of the heteroaromatic oxindole group is/are a nitro group(s).

Synthesis of Intermediates (i) The compounds of formula III and salts thereof, constitute a further feature of the present invention. Such compounds in which $L^1$ is halogeno may for example be prepared by halogenating a compound of the formula XIV:

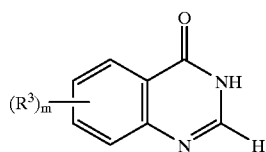 (XIV)

(wherein R³ and m are as hereinbefore defined).

Convenient halogenating agents include inorganic acid halides, for example thionyl chloride, phosphorus(III) chloride, phosphorus(V)oxychloride and phosphorus(V) chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XIV and salts thereof which constitute a further feature of the present invention may for example be prepared by reacting a compound of the formula XV:

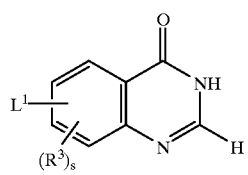 (XV)

(wherein $R^3$, s and $L^1$ are as hereinbefore defined) with a compound of the formula XI as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XIV and salts thereof wherein at least one $R^3$ is $R^{15}X^7$ and wherein $X^7$ is —O—, —S—, —SO$_2$—, —CONR$^{17}$—, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxy$C_{2-3}$alkyl), may for example also be prepared by the reaction of a compound of the formula XVI:

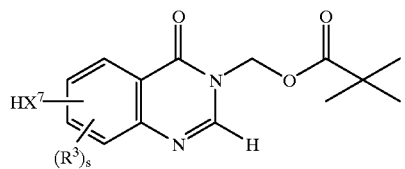 (XVI)

(wherein $R^3$, s and $X^7$ are as hereinbefore defined) with a compound of the formula IX as hereinbefore defined. The reaction may for example be effected as described for process (e) hereinbefore. The pivaloyloxymethyl group can then be cleaved by reacting the product with a base such as, for example, aqueous ammonia, triethylamine in water, an alkali metal or alkaline earth metal hydroxide or alkoxide, preferably aqueous ammonia, aqueous sodium hydroxide or aqueous potassium hydroxide, in a polar protic solvent such as an alcohol, for example methanol or ethanol. The reaction is conveniently effected at a temperature in the range 20 to 100° C., preferably in the range 20 to 50° C.

The compounds of formula XIV and salts thereof may also be prepared by cyclising a compound of the formula XVII:

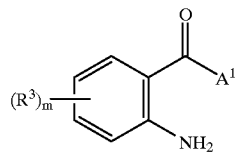 (XVII)

(wherein R³ and m, are as hereinbefore defined, and A¹ is an hydroxy, alkoxy (preferably $C_{1-4}$alkoxy) or amino group) whereby to form a compound of formula XIV or salt thereof. The cyclisation may be effected by reacting a compound of the formula XVII, where A¹ is an hydroxy or alkoxy group, with formamide or an equivalent thereof effective to cause cyclisation whereby a compound of formula XIV or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XIV may also be prepared by cyclising a compound of the formula XVII, where A¹ is an amino group, with formic acid or an equivalent thereof effective to cause cyclisation whereby a compound of formula XIV or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XVII and salts thereof, which constitute a further feature of the present invention, may for example be prepared by the reduction of the nitro group in a compound of the formula XVIII:

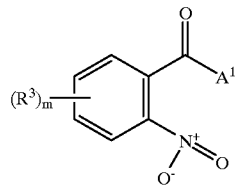 (XVIII)

(wherein R³, m and A¹ are as hereinbefore defined) to yield a compound of formula XVII as hereinbefore defined. The reduction of the nitro group may conveniently be effected by any of the procedures known for such a transformation. The reduction may be carried out, for example, by stirring a solution of the nitro compound under hydrogen at 1 to 4 atmospheres pressure in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound under hydrogen at 2 atmospheres pressure in the presence of the activated metal and a solvent or diluent such as a mixture of water and alcohol, for example methanol or ethanol, at a temperature in the range, for example 50 to 150° C., conveniently at about 70° C.

Compounds of the formula XVIII and salts thereof which constitute a further feature of the present invention, may for example be prepared by the reaction of a compound of the formula XIX:

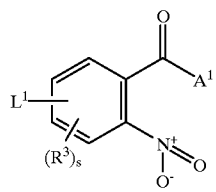

(XIX)

(wherein $R^3$, s, $L^1$ and $A^1$ are as hereinbefore defined) with a compound of the formula XI as hereinbefore defined to give a compound of the formula XVIII. The reaction of the compounds of formulae XIX and XI is conveniently effected under conditions as described for process (f) hereinbefore.

Compounds of formula XVIII and salts thereof wherein at least one $R^3$ is $R^{15}X^7$ and wherein $X^7$ is —O—, —S—, —SO$_2$—, —CONR$^{17}$—, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxyC$_{2-3}$alkyl), may for example also be prepared by the reaction of a compound of the formula XX:

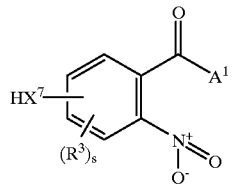

(XX)

(wherein $R^3$, s, $A^1$ and $X^7$ are as hereinbefore defined) with a compound of the formula IX as hereinbefore defined to yield a compound of formula XVIII as hereinbefore defined. The reaction of the compounds of formulae XX and IX is conveniently effected under conditions as described for process (e) hereinbefore.

The compounds of formula III and salts thereof wherein at least one $R^3$ is $R^{15}X^7$ and wherein $X^7$ is —O—, —S—, —SO$_2$—, —CONR$^{17}$—, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxyC$_{2-3}$alkyl), may also be prepared for example by reacting a compound of the formula XXI:

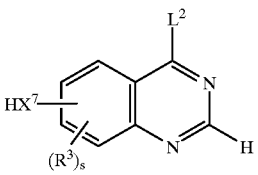

(XXI)

(wherein $R^3$, $X^7$ and s are as hereinbefore defined, and $L^2$ represents a displaceable protecting moiety) with a compound of the formula IX as hereinbefore defined, whereby to obtain a compound of formula III in which $L^1$ is represented by $L^2$.

A compound of formula XXI is conveniently used in which $L^2$ represents a phenoxy group which may if desired carry up to 5 substituents, preferably up to 2 substituents, selected from halogeno, nitro and cyano. The reaction may be conveniently effected under conditions as described for process (e) hereinbefore.

The compounds of formula XXI and salts thereof which constitute a further feature of the present invention may for example be prepared by deprotecting a compound of the formula XXII:

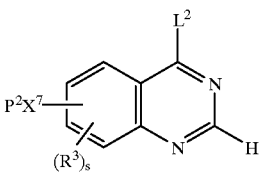

(XXII)

(wherein $R^3$, $P^2$, $X^7$, s and $L^2$ are as hereinbefore defined with the proviso that $X^7$ is not —CH$_2$—). Deprotection may be effected by techniques well known in the literature, for example where $P^2$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XIV as hereinbefore defined, followed by introduction of halide to the compound of formula XIV, thus obtained as hereinbefore defined, to yield a compound of formula III in which $L^1$ represents halogen.

(ii) Compounds of formula IV and salts thereof which constitute a further feature of the present invention, may be prepared by any of the known procedures, references include: "The Chemistry of Indoles" R. J. Sundberg page 341, 1970 Academic, New York; Gassman and Bergen, 1974, Jnl. Am. Chem. Soc., 96, 5508 and 5512; Quallich and Morrissey, 1993, Synthesis, 51; Cherest et al., 1989, Tetrahedron Letters, 30, 715; Marfat et al., 1987, Tetrahedron Letters, 28, 4027–4030; Robinson et al., 1991, J Org Chem 56, 4805; European Patent Application Publication number 0436333 A2; Daisley et al., Synth. Commun. 1981, 11(9), 743–749; Robinson et al., J Heterocyclic Chem 1996, 33, 287.

In particular 5,7-diazaoxindoles may be made by a series of steps commencing with the reaction of a succinate diester with ethyl formate in the presence of a base. Such a base is for example an alkali metal hydride, for example sodium hydride, or an alkali metal or alkaline earth metal amide for example sodium amide, sodium bis(trimethylsilyl)amide, potassium amide or potassium bis(trimethylsilyl)amide, preferably sodium hydride. The reaction is preferably effected in the presence of an inert solvent or diluent (as defined hereinbefore in process (a)), such as benzene, xylene, toluene, preferably in toluene, and at a temperature in the range, for example, 25 to 100° C. preferably in the range 25 to 80° C. The mixture is then reacted with an amidine, such as an alkylamidine, in an alcoholic solvent such as methanol, ethanol, 2-propanol, 2-pentanol, 2-methyl-1-propanol, preferably in 2-propanol. The reaction is conveniently effected at the temperature of reflux of the solvent. (Reference: Biggs, J Amer Chem Soc. 1959, 1849). Halogenation of the product is then conveniently effected under conditions as described in (i) hereinbefore. Displacement of the chlorine atom may be effected by reacting the product with an azide derivative such as sodium azide, trimethylsilyl azide, preferably sodium azide, in a dipolar aprotic solvent (as defined hereinbefore in process (a)), conveniently in N,N-dimethylformamide. The reaction may advantageously be effected at a temperature in the range 50 to 80° C. The resulting azide is hen reduced by any of the procedures known for such a transformation. The reduction may e effected in a similar manner to that described in (i) hereinbefore. Thus for example, the reduction may be effected by stirring the azide in the presence of 10% palladium-on-charcoal catalyst under hydrogen at atmospheric pressure in the presence of a solvent or diluent such as an alcohol, for example methanol, ethanol or N,N-dimethylformamide, at a temperature in the range 15 to 50° C. preferably at ambient temperature. Cyclisation may then be achieved by heating the product in an inert solvent such as toluene, xylene, diphenyl ether, Dowtherm (trade mark of Fluka Chemie AG) mixture, preferably diphenyl ether or Dowtherm mixture. The cyclisation may conveniently be effected at a temperature in the range, for example, 100 to 250° C. preferably in the range 150 to 200° C.

Alternatively (after Seela et. al., Liebgs Ann. Chem. 1984, 275–282 and Seela et. al., Helvetica Chimica Acta 1994, 77, 194) 5,7-diazaoxindoles may also be made by reacting a compound of formula Z1:

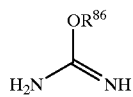

(Z1)

(wherein $R^{86}$ represents $C_{1-3}$alkyl, or any of the values of $R^4$ (wherein $R^4$ is as defined hereinbefore)), with ethyl 2-cyano-4,4-diethoxybutylcarboxylate. The reaction is conveniently done in the presence of a base such as an alkali metal or alkaline earth metal alkoxide, for example sodium methoxide, sodium ethoxide, potassium methoxide or potassium ethoxide. The reaction is preferably effected in the presence of a solvent such as an alcohol conveniently methanol, ethanol, advantageously the alcohol corresponding to the $R^{86}$ substituent, for example if $R^{86}$ is methoxy the solvent is advantageously methanol. The reaction is conveniently effected at a temperature in the range, for example, 50 to 200° C., preferably in the range 50 to 150° C. The resulting azide may then be treated with an inorganic acid such as hydrochloric acid or sulphuric acid to give an azaindole. Halogenation of the azaindole may then be effected with a halogenating agent (as described in (i) hereinbefore) in an inert solvent or diluent, in an aromatic hydrocarbon solvent or in an aromatic amine, for example the reaction may advantageously be effected in methylene chloride, trichloromethane, benzene, toluene, N N-dimethylaniline, N,N-diethylaniline, more preferably in N,N-dimethylaniline. The reaction is conveniently effected at a temperature in the range, for example, 50 to 200° C. preferably in the range 80 to 150° C. The azaindole may then be reduced under similar conditions to those described in (i) hereinbefore for the reduction of a nitro group. For example, the reduction may be achieved by stirring a solution of the azaindole under hydrogen at atmospheric pressure in the presence of 10% palladium-on-charcoal catalyst in the presence of a solvent such as an alcohol, methanol or ethanol, containing an amine such as triethylamine, ethylamine or ammonia, preferably containing ammonia, conveniently at a temperature in the range 15 to 80° C., preferably at ambient temperature. Bromination of the resulting azaindole may then conveniently be effected by treating the azaindole with pyridinium bromide perbromide in a protic solvent such as an alcohol, for example, 2-methyl-2-propanol at a temperature in the range 25 to 75° C., preferably in the range 25 to 45° C. Reduction of the product is then effected, in a similar manner to that described in (i) hereinbefore. For example, the reduction may conveniently be effected by stirring a solution of the product under hydrogen at atmospheric pressure in the presence of an inert solvent or diluent such as methanol, ethanol or N,N-dimethylformamide, in the presence of 10% palladium-on-charcoal catalyst.

Alternatively (after Yamanaka et. al., Chem. Pharm. Bull. 1993, 41, 81–86) 5,7-diazaoxindoles may also be made by reacting a compound of formula Z2:

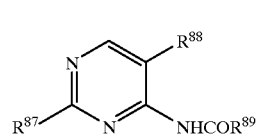

(Z2)

(wherein $R^{87}$ represents hydrogen, $Ca_{1-5}$alkyl, $C_{1-5}$alkoxy or any of the values of $R^2$ as defined hereinbefore with the exception of hydroxy, amino, $C_{2-4}$alkanoyl and $C_{1-4}$alkylsulphinyl, $R^{88}$ represents bromo or iodo and $R^{89}$ represents $C_{1-5}$alkyl or phenyl), with a trialkylstannane, preferably a tributylstannane, such as (2-ethoxyvinyl) tributyltin, in the presence of a palladium salt, preferably dichlorobis(triphenylphosphine)palladium, in the presence of an ammonium salt such as tetraethylammonium chloride. The reaction may be effected in a dipolar aprotic solvent (as defined hereinbefore in process (a)) such as N,N-dimethylformamide, acetonitrile or tetrahydrofuran, preferably in N,N-dimethylformamide or acetonitrile. The reaction is conveniently done at a temperature in the range 50 to 200° C. more preferably in the range 80 to 150° C. Cyclisation of the product may be effected by heating it in a polar protic solvent such as an alcohol, preferably methanol or ethanol, in the presence of an inorganic acid such as hydrochloric, hydrobromic or sulphuric acid. The reaction may conveniently be effected at a temperature in the range 50 to 200° C., preferably in the range 50 to 150° C. Bromination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N N-dimethylformamide, in the presence of 10% palladium-on-charcoal catalyst.

4,6-Diazaoxindoles (after Yamanaka, Chem. Pharm. Bull. 1993, 41, 81–86) may be made by reacting a compound of formula Z3:

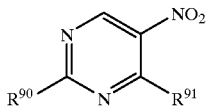

(Z3)

(wherein $R^{90}$ represents hydrogen, $C_{1-5}$alkyl, $C_{1-5}$alkoxy or any of the values of $R^2$ as defined hereinbefore with the exception of hydroxy, amino, $C_{2-4}$alkanoyl, and $C_{1-4}$alkylsulphinyl and $R^{91}$ represents bromo or iodo) with a trialkylstannane, preferably a tributylstannane, such as (2-ethoxyvinyl)tributyltin, in the presence of a palladium salt, preferably dichlorobis(triphenylphosphine)palladium, in the presence of an ammonium salt such as tetraethylammonium chloride. The reaction may conveniently be effected in a dipolar aprotic solvent (as defined hereinbefore in process (a)), such as N,N-dimethylformamide, acetonitrile or tetrahydrofuran, preferably in N,N-dimethylformamide, or acetonitrile. The reaction is advantageously done at a temperature in the range 50 to 200° C. more preferably in the range 80 to 150° C. The reduction of the nitro group in the resulting product may be achieved under similar conditions to those described in (i) hereinbefore. For example the reaction is conveniently effected by stirring the product under hydrogen at atmospheric pressure in the presence of a polar solvent such as methanol, ethanol or a mixture of an alcohol and a chlorinated solvent such as methylene chloride, in the presence of an activated metal catalyst such as Raney nickel. The reaction may conveniently be effected at a temperature in the range 15 to 80° C. more preferably at ambient temperature. Cyclisation of the product may be effected by heating a solution of the product in an alcohol, such as methanol or ethanol, containing inorganic acid, for example, aqueous hydrochloric, hydrobroric or sulphuric acid, at a temperature in the range 50 to 150° C., more preferably at the temperature of reflux of the solvent. The reaction may conveniently be effected at the same time as the reduction of the nitro group and without isolation of the intermediate product. Bromination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N,N dimethylformamide, in the presence of 10% palladium-on-charcoal catalyst.

5,6-Diazaoxindoles (after Marquet et. el., Chimie Therapeutique 1968, 3, 348), may be prepared by reacting a compound of the formula Z4:

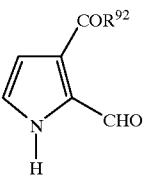

(Z4)

(wherein $R^{92}$ represents $C_{1-5}$alkoxy, halo, amino, $C_{1-5}$alkylamino, di($C_{1-5}$alkyl)amino or arylamino, preferably $C_{1-5}$alkoxy, especially ethoxy) with hydrazine. The reaction may conveniently be effected in a polar protic solvent such as methanol, ethanol, 2-propanol, 3-methyl-1-butanol, preferably in ethanol, at a temperature in the range 50 to 120° C., preferably at the temperature of reflux of the solvent. Halogenation of the product may then be effected by reacting the product with a halogenating agent (as described in (i) hereinbefore). The reaction is conveniently effected without a solvent or in the presence of an inert solvent or diluent such as, for example, a halogenated solvent such as methylene chloride, trichloromethane or carbon tetrachloride, or an aromatic hydrocarbon solvent such as benzene or toluene. The reaction may conveniently be effected at a temperature in the range, for example 10 to 150° C., preferably in the range 40 to 100° C. The resulting azaindole may then be reduced in a similar manner to that described in (i) hereinbefore. The reaction may conveniently be effected in the presence of a base such as an alkali metal or alkaline earth metal alkoxide, for example, sodium ethoxide or sodium methoxide. For example, the reduction may be achieved by heating a solution of the azaindole under hydrogen at 2 atmospheres pressure in the presence of 10% palladium-on-charcoal catalyst in ethanol containing sodium hydroxide, conveniently at a temperature in the range 15 to 80° C., preferably at ambient temperature. Bromination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N,N-dimethylformamide, in the presence of 10% palladium-on-charcoal catalyst.

4,7-Diazaoxindoles may be prepared (after Parrick et al, J. Chem. Soc. Perk 1 1976, 1361) by reacting a compound of the formula Z5:

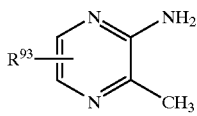

(Z5)

(wherein $R^{93}$ represents hydrogen, $C_{1-5}$alkyl, $C_{1-5}$alkoxy or any of the values for $R^2$ as defined hereinbefore with the exception of hydroxy, amino and $C_{2-4}$alkanoyl) with an orthoformate such as methyl orthoformate or ethyl orthoformate, in the presence of a protic solvent such as an alcohol, for example, methanol, 1-propanol, 2-propanol, preferably methanol. The reaction may conveniently be effected in the presence of an inorganic acid such as hydrochloric, hydrobromic or sulphuric acid. The reaction may conveniently be effected at a temperature in the range 50 to 180° C., preferably in the range 50 to 150° C. The product is then heated in the presence of an amine or alkylaniline such as dimethylamine, diethylamine, methylaniline, ethylaniline, preferably methylaniline. The reaction may conveniently be effected at a temperature in the range 100 to 200° C., preferably in the range 150 to 180° C. The product is then reacted with an alkali metal amide or alkaline earth metal amide such as sodium amide or lithium amide, preferably sodium amide, in the presence of an alkylaniline such as methylaniline, ethylaniline, preferably methylaniline. The reaction may conveniently be effected at a temperature in the range 50 to 200° C., preferably in the range 50 to 150° C. Bromination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N,N-dimethylformamide, in the presence of 10% palladium-on-charcoal catalyst.

4,5-Diazaoxindoles may be prepared (after Parrick et al, J. Chem. Soc. Perk 1, 1976, 1363 and P Cook et al, J. Het. Chem. 1973, 10, 807) by reacting a compound of formula Z6:

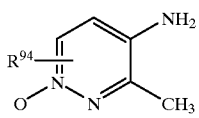

(Z6)

(wherein $R^{94}$ represents hydrogen, $C_{1-5}$alkyl, $C_{1-5}$alkoxy or any of the values for $R^2$ as defined hereinbefore with the exception of hydroxy, amino and $C_{2-4}$alkanoyl) with an orthoformate derivative such as methyl orthoformate or ethyl orthoformate in the presence of an inert solvent such as N,N-dimethylformamide, N,N-dimethylacetamide or 1-methyl-2-pyrrolidinone, in the presence of a protic solvent such as an alcohol, for example methanol, 1-propanol, 2-propanol, advantageously methanol, preferably a mixture of N,N-dimethylformamide and methanol. The reaction may conveniently be effected in the presence of an inorganic acid such as hydrochloric, hydrobromic or sulphuric acid. The reaction may conveniently be effected at a temperature in the range 50 to 180° C., preferably in the range 50 to 150° C. The product may then be reacted with a potassium salt of diethyl or dimethyl oxalate. The reaction may conveniently be effected in a solvent or diluent such as ethanol, methanol, ether or tetrahydrofuran, preferably a mixture of ethanol and ether. The reaction may conveniently be effected at a temperature in, the range 10 to 40° C. preferably in the range 20 to 30° C. Cyclisation of the product may then be achieved by stirring the product in an aqueous solution of concentrated inorganic acid such as hydrochloric or hydrobromic acid at ambient temperature. The reduction of the nitrogen oxide group may then be effected by any procedure known in the literature to reduce nitrogen oxide, (Chemistry of Heterocyclic N-oxides, Katritsky and Lagowski, Academic Press 1971), such as reacting the product with phosphorus (ml)chloride or phosphorus(V)chloride, in a chlorinated solvent such as methylene chloride or trichloromethane, or by reacting the product with trifluoroacetic anhydride in acetonitrile containing sodium iodide. The azaindole is then prepared by the reaction of the product with an aqueous solution of an inorganic base, such as sodium hydroxide, potassium hydroxide, in the presence of an inert solvent or diluent such as methanol, ethanol, preferably sodium hydroxide in a mixture of water and N,N-dimethylformamide or methanol. The reaction may conveniently by effected at a temperature in the range 25 to 100° C. preferably in the range 25 to 50° C. The product is then treated with a solution of a concentrated or dilute inorganic acid such as hydrochloric, hydrobromic or sulphuric acid in the presence of an inert solvent such as methanol, ethanol, methylene chloride, preferably a mixture of water and ethanol. Bromnination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N N-dimethylformamide, in the presence of 10% palladium-on-charcoal catalyst.

In another aspect of the present invention 6,7-diazaoxindoles may be prepared by using a compound of formula Z7:

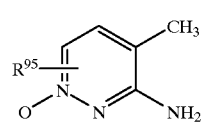

(Z7)

(wherein $R^{95}$ represents hydrogen, $C_{1-5}$alkyl, $C_{1-5}$alkoxy or any of the values for $R^2$ as defined hereinbefore with the exception of hydroxy, amino and $C_{2-4}$alkanoyl), instead of a compound of formula Z6 in the reactions described hereinbefore for the preparation of 4,5-diazaoxindoles.

In another aspect of the present invention 5,6,7-triazaoxindoles may be prepared by reacting a compound of formula Z8:

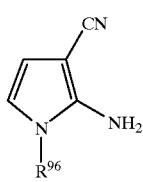

(Z8)

(wherein $R^{96}$ represents hydrogen, $C_{1-5}$alkyl, $C_{1-5}$alkoxymethyl, di($C_{1-5}$alkoxy)methyl, aryl, benzyl, $C_{1-5}$alkoxycarbonyl, di($C_{1-5}$alkoxy)benzyl, preferably hydrogen, benzyl or $C_{1-5}$alkoxycarbonyl) with an inorganic acid such as polyphosphoric acid in phosphoric acid. The reaction may conveniently be effected at a temperature in the range 50 to 150° C. preferably in the range 100 to 150° C. The product may or may not be isolated before cyclisation. Cyclisation of the product may be effected by mixing a solution of the product in polyphosphoric acid with a solution of sodium nitrite. The reaction may conveniently be effected in a solvent such as water and at a temperature in the range −5 to 10° C., preferably 0° C. Halogenation of the cyclised product may then be effected with a halogenating agent, (as described in (i) hereinbefore), preferably with phosphorus(V)chloride. The reaction may conveniently be effected in an inert solvent or diluent such as for example methylene chloride, trichloromethane, in an aromatic hydrocarbon solvent such as for example benzene or toluene, or in an aromatic amine such as N,N-dimethylaniline. N,N- diethylaniline, more preferably N,N-dimethylaniline. The reaction is conveniently effected at a temperature in the range of 50 to 200° C. more preferably in the range 80 to 150° C. The resulting halogenated azaindole may then be reduced in a similar manner to that described in (i) hereinbefore. For example, the reduction may conveniently be effected by stirring a solution of the azaindole under hydrogen at atmospheric pressure in the presence of a solvent such as an alcohol, for example, methanol or ethanol, containing an amine such as triethylamine, ethylamine or ammonia, preferably containing ammonia, in the presence of 10% palladium-on-charcoal catalyst at a temperature in the range 15 to 80° C., preferably at ambient temperature. Bromination of the resulting azaindole may then conveniently be effected as described hereinbefore. Reduction of the product is then effected in a similar manner to that described in (i) hereinbefore. For example, the reduction may conveniently be effected by stirring a solution of the product under hydrogen at atmospheric pressure in the presence of an inert solvent or diluent such as methanol, ethanol or N,N-dimethylformamide, in the presence of 10% palladium-on-charcoal catalyst.

In another aspect of the present invention 4,5,6-triazaoxindoles may be prepared by using a compound of formula Z9:

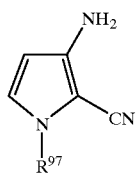

(Z9)

(wherein $R^{97}$ represents hydrogen, $C_{1-5}$alkyl, $C_{1-5}$alkoxymethyl, di($C_{1-5}$alkoxy)methyl, aryl, benzyl, $C_{1-5}$alkoxycarbonyl, di($C_{1-5}$alkoxy)benzyl, preferably hydrogen, benzyl or $C_{1-5}$alkoxycarbonyl), instead of a compound of formula Z8 in the reactions described hereinbefore for the preparation of 5,6,7-triazaoxindoles.

In the preparation of azaoxindoles, diazaoxindoles and triazaoxindoles, substituents on the heteroaromatic oxindole group may be added at any stage of the preparation by any process known to be appropriate for the purpose.

(iii) The compounds of formula V and salts thereof, constitute a further feature of the present invention, and may for example be prepared by the reaction of a compound of formula III as hereinbefore defined with a compound of the formula XXIII:

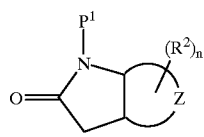

(XXIII)

(wherein $R^2$, n, ring Z and $P^1$ are as hereinbefore defined). The reaction may for example be effected as described for process (a) hereinbefore.

The compounds of formula V and salts thereof may also be prepared by reacting a compound of formula XXIV:

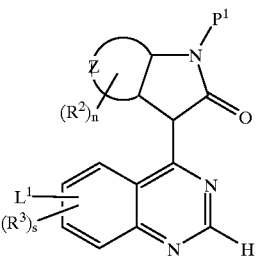

(XXIV)

(wherein $R^2$, $R^3$, $L^1$, n, ring Z, s and $P^1$ are as hereinbefore defined) with a compound of formula XI as hereinbefore defined. The reaction may for example be effected as described for process (f) above.

The compounds of formula V and salts thereof wherein at least one $R^3$ is $R^{15}X^7$ and wherein $X^7$ is —O—, —S—, —SO$_2$—, —CONR$^{17}$—, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxyC$_{2-3}$alkyl), may also be prepared by reacting a compound of formula XXV:

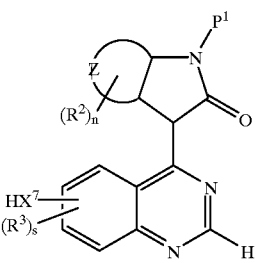

(XXV)

(wherein $R^2$, $R^3$, $X^7$, n, ring Z, s and $P^1$ are as hereinbefore defined) with a compound of the formula IX as hereinbefore defined. The reaction may for example be effected as described for process (e) hereinbefore.

The compounds of formula XXIV and salts thereof constitute a further feature of the present invention and may for example be prepared by reaction of a compound of formula XXVI:

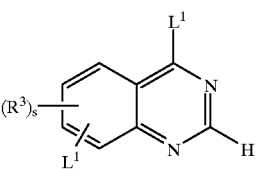

(XXVI)

(wherein $R^3$, s and each $L^1$ are as hereinbefore defined, and the $L^1$ in the 4-position and the other $L^1$ in a further position on the quinazoline ring may be the same or different) with a compound of the formula XXIII as hereinbefore defined. The reaction may be effected for example by a process as described in (a) above.

Compounds of the formula XXV and salts thereof which constitute a further feature of the present invention may be made by reacting compounds of the formulae XXII and XXIII as hereinbefore defined, under conditions described in (a) hereinbefore, to give a compound of formula XXVII:

(XXVII)

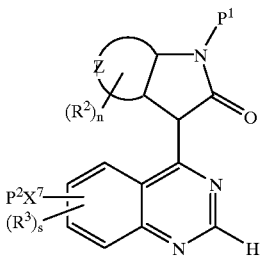

(wherein $R^2$, $R^3$, $P^1$, $P^2$, $X^7$, s, ring Z and n are as hereinbefore defined with the proviso that $X^7$ is not —$CH_2$—) and then deprotecting the compound of formula XXVII for example as described in (i) above.

(iv) Compounds of the formula VI and salts thereof constitue a further feature of the present invention and may be made by the reaction of a compound of formula III as hereinbefore defined with a compound of the formula XXVIII:

(XXVIII)

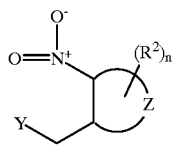

(wherein $R^2$, n, ring Z and Y are as hereinbefore defined). The reaction may for example be effected as described for the process (a) hereinbefore.

(v) The compounds of formula VII and salts thereof, constitute a further feature of the present invention, and may for example be prepared by the reaction of a compound of formula III as hereinbefore defined with a compound of the formula XXIX:

(XXIX)

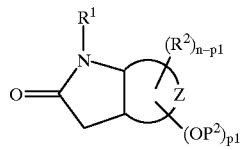

(wherein $R^1$, $R^2$, n, $p^1$, ring Z and p2 are as hereinbefore defined). The reaction may for example be effected as described for process (a) hereinbefore. The compounds of formula VII and salts thereof may also be prepared by reacting a compound of formula XXX:

(XXX)

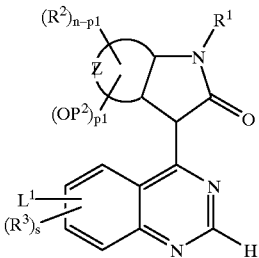

(wherein $R^1$, $R^2$, $R^3$, $L^1$, n, p1, s, ring Z and $p^2$ are as hereinbefore defined) with a compound of formula XI as hereinbefore defined. The reaction may for example be effected as described for process (f) above.

The compounds of formula VII and salts thereof wherein at least one $R^3$ is $R^{15}X^7$ and wherein $X^7$ is —O—, —S—, —$SO_2$—, —$CONR^{17}$—, —$SO_2NR^{18}$— or —$NR^{20}$— (wherein $R^{17}$, $R^{18}$ and $R^{20}$ each independently represents hydrogen, $C_{1-3}$alkyl or $C_{1-3}$alkoxy$C_{2-3}$alkyl), may also be prepared by reacting a compound of formula XXXI:

(XXXI)

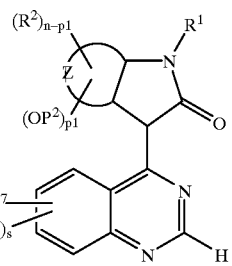

(wherein $R^1$, $R^2$, $R^3$, $X^7$, n, s, p1, ring Z and P are as hereinbefore defined) with a compound of the formula IX as hereinbefore defined. The reaction may for example be effected as described for process (e) hereinbefore.

The compounds of formula XXX and salts thereof may for example be prepared by the reaction of a compound of formula XXVI as hereinbefore defined with a compound of the formula XXIX as hereinbefore defined. The reaction may be effected for example by a process as described in (a) above.

Compounds of the formula XXXI and salts thereof may be made by reacting compounds of the formulae XXII and XXIX as hereinbefore defined, under conditions described in (a) hereinbefore, to give a compound of formula XXXII:

(XXXII)

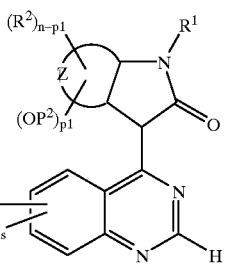

(wherein $R^1$, $R^2$, $R^3$, $P^2$, $X^7$, p1, ring Z, n and s are as hereinbefore defined with the proviso that $X^7$ is not —CH$_2$—) and then deprotecting the compound of formula XXXII for example as described in (i) above.

(vi) Compounds of formula VIII as hereinbefore defined and salts thereof constitute a further feature of the present invention and may be made by deprotecting the compound of formula XXXIII:

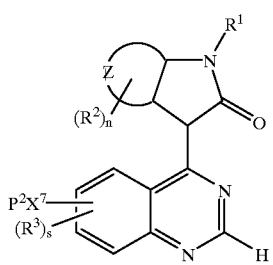

(XXXIII)

(wherein R$^1$, R$^2$, R$^3$, P$^2$, X$^7$, s, ring Z and n are as hereinbefore defined with the proviso that X$^7$ is not —CH$_2$—) by a process for example as described in (i) above.

Compounds of the formula XXXIII and salts thereof which constitute a further feature of the present invention may be made by reacting compounds of the formulae XXII and IV as hereinbefore defined, under the conditions described in (a) hereinbefore, to give a compound of the formula XXXIII or salt thereof.

(vii) Compounds of the formula X and salts thereof constitute a further feature of the present invention and may be made by reacting compounds of the formulae XXVI and IV as hereinbefore defined, the reaction for example being effected by a process as described in (a) above.

(viii) Compounds of formula XII as defined hereinbefore and salts thereof constitute a further feature of the present invention and may for example be made by the reaction of compounds of formula VIII as defined hereinbefore with compounds of the formula XXXIV:

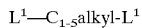

(XXXIV)

(wherein L$^1$ is as hereinbefore defined) to give compounds of formula XII or salts thereof. The reaction may be effected for example by a process as described in (e) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, IV, V, VI, VII, VIII, X, XII, XIV, XV, XVI, XVII, XVIII, XIX, XX, XXI, XXII, XXIII, XXIV, XXV, XXVI, XXVII, XXVIII, XXIX, XXX, XXXI, XXXII and XXXIII and these are provided as a further feature of the invention. The preparation of these compounds is as described herein and/or is by methods well known to persons skilled in the art of organic chemistry.

The identification of compounds which potently inhibit the tyrosine kinase activity associated with VEGF receptors such as Flt and/or KDR and with FGF R1 receptors and which inhibit angiogenesis and/or increased vascular permeability is desirable and is the subject of the present invention. These properties may be assessed, for example, using one or more of the procedures set out below:
(a) In Vitro Receptor Tyrosine Kinase Inhibition Test This assay determines the ability of a test compound to inhibit tyrosine kinase activity. DNA encoding VEGF, FGF or EGF receptor cytoplasrfic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R$^1$ receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X 100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blanki" control wells which contained manganese(II)chloride without ATP. To start the reactions 50µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5kg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and FGF RI receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin $\alpha v \beta 3$ function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone $5\alpha$-dihydroreductase (for example finasteride), anti-invasion agents (for example metalloproteinase inhibitors like marimastat and inhibitors of urokinase plasminogen activator receptor function) and inhibitors of growth factor function, (such growth factors include for example EGF, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF and/or FGF, especially those tumours which are significantly dependent on VEGF and/or FGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity and FGF R1 receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(vii) intermediates were not generally fully characterised and purity was assessed by thin layer chromatography (TLC), high-performance liquid chromatography (HPLC), infra-red (IR) or NMR analysis;

(viii) petroleum ether refers to that fraction boiling between 40–60° C.

(ix) the following abbreviations have been used:

DMF N,N-dimethylformamide

DMSO dimethylsulphoxide
TFA trifluoroacetic acid
THF tetrahydrofuran.]

EXAMPLE 1

7-Azaoxindole hydrobromide (269 mg, 1.25 mmol), (Tet.Let. 1987, 28, 4027), was added to a suspension of sodium hydride (100 mg, 2.5 mmol, prewashed with hexane) in a mixture of THF (3 ml) and DMF (3 ml). After stirring for 40 minutes at ambient temperature, 4-chloro-7-methoxy-6-(3-morpholinopropoxy)quinazoline (169 mg, 0.5 mmol) was added. After heating for 1 hour at 75° C., the volatiles were removed by evaporation. The residue was partitioned between ethyl acetate and water. The aqueous layer was separated and adjusted to pH8 with 2M hydrochloric acid. After extraction with methylene chloride, the organic layer was dried ($MgSO_4$), filtered and the volatiles removed by evaporation. The residue was dissolved in methylene chloride/methanol and 3M hydrogen chloride in ether (0.5 ml) was added. After dilution with ether, the solid was collected by filtration and dried under vacuum to give 4-(7-azaoxindol-3-yl)-7-methoxy-6-(3-morpholinopropoxy) quinazoline (150 mg, 59%).

$^1$H NMR Spectrum: ($DMSOd_6$, $CF_3COOD$) 2.3(m, 2H); 3.1–3.2(m, 2H); 3.3(m, 2H); 3.5(d, 2H); 3.8(t, 2H); 4.0(s, 3H); 4.05(m, 2H); 4.25(t, 2H); 7.25(s, 1H); 7.3(dd, 1H); 7.95(d, 1H); 8.72(s, 1H); 8.6–8.8(m, 2H)

MS-ESI: 436 [MH]$^+$

Elemental analysis: Found C, 51.4; H, 5.8; N, 12.7%
$C_{23}H_{25}N_5O_4$ 2.3HCl 1.2$H_2O$ Requires C, 51.1; H, 5.5; N, 12.9%

The starting material was prepared as follows:

A suspension of 4-(3-chloro-4-fluoroanilino)-7-methoxy-6-(3-morpholinopropoxy)quinazoline (6.0 g, 13.4 mmol), (WO 96/33980), in 6M hydrochloric acid (120 ml) was heated at reflux for 6 hours. The mixture was cooled to 0° C. and carefully, with cooling, was neutralised by addition of concentrated aqueous ammonia. The resulting precipitate was collected by filtration, washed with dilute aqueous ammonia and water and dried under vacuum to give 7-methoxy-6-(3-morpholinopropoxy)-3,4-dihydroquinazolin-4-one (4.2 g, 98%yield).

$^1$H NMR Spectrum: ($DMSOd_6$) 2.4(m, 6H); 3.59(t, 4H); 3.75(t, 2H); 3.90(s, 3H); 4.12(t, 2H); 7.12(s, 1H); 7.43 (s, 1H); 7.98 (s, 1H); 12.0(br s, 1H)

MS-ESI: 320 [MH]$^+$

Elemental analysis: Found C, $_{58.6}$; H, 6.5; N, 12.7%
$C_{16}H_{21}N_3O_4$ 0.5$H_2O$ Requires C, $_{58.5}$; H, 6.7; N, 12.8%

A solution of 7-methoxy-6-(3-morpholinopropoxy)-3,4-dihydroquinazolin-4-one (990 mg, 3.1 mmol) in thionyl chloride (10 ml) containing DMF (0.1 ml) was heated at 80° C. for 1.5 hours. After cooling, toluene was added and the solvent was removed by evaporation. The residue was triturated with ether, and the volatiles were removed by evaporation. The residue was partitioned between ethyl acetate and water and the aqueous layer was adjusted to pH7.5 with 2M sodium hydroxide. The organic layer was washed with brine, dried ($MgSO_4$) and the volatiles removed by evaporation. The residue was purified by flash chromatography eluting with methylene chloride/methanol (1/9 followed by 95/5). The solid was triturated with hexane, collected by filtration and washed with ether to give 4-chloro-7-methoxy-6-(3-morpholinopropoxy)quinazoline (614 mg, 58%).

$^1$H NMR Spectrum: ($CDCl_3$) 2.12(m, 2H); 2.50(br s, 4H); 2.59(t, 2H); 3.73(t, 4H); 4.05(s, 3H); 4.27(t, 2H); 7.33(s, 1H); 7.40(s, 1H); 8.86(s, 1H)

EXAMPLE 2

A solution of 7-azaoxindole (268 mg, 2 mmol) in THF (3 ml) was added to a suspension of sodium hydride (80 mg, 2 mmol, prewashed with THF) in THF (4 ml). After stirring for 20 minutes at ambient temperature a solution of 4-chloro-6-methoxy-7-(2-methoxyethoxy)quinazoline (180 mg, 0.7 mmol) in a mixture of THF (3 ml) and DMF (1 ml) was added. After stirring for 30 minutes at ambient temperature followed by 1 hour at 65° C., the volatiles were removed by evaporation. The residue was partitioned between water and ether. The aqueous layer was separated and adjusted to pH4 with 2M hydrochloric acid. The precipitate was collected by filtration and dried under vacuum, it was then suspended in methylene chloride/methanol (1/1) and 3M hydrogen chloride in ether was added. The solid was collected by filtration, washed with methanol followed by ether and dried under vacuum to give 4-(7-azaoxindol-3-yl)-6-methoxy-7-(2-methoxyethoxy)quinazoline (388 mg, 68%).

$^1$H NMR Spectrum: ($DMSOd_6$, NaOD, $D_2O$) 3.44(s, 3H); 3.85(t, 2H); 3.90(s, 3H); 4.27(t, 2H); 6.51(dd, 1H); 6.98(s, 1H); 7.51(d, 1H); 8.05–8.15(m, 1H); 8.45(s, 1H); 9.3(brs, 1H)

MS-ESI: 367 [MH]$^+$

Elemental analysis: Found C, 50.6; H, 4.7; N, 12.3%
$C_{19}H_{18}N_4O_4$ 0.9$H_2O$ 1.85HCl Requires C, 50.7; H, 4.8; N, 12.4%

The starting material was prepared as follows:

A mixture of ethyl 4-hydroxy-3-methoxybenzoate (9.8 g, 50 mmol), 2-bromoethyl methyl ether (8.46 ml, 90 mmol) and potassium carbonate (12.42 g, 90 mmol) in acetone (60 ml) was heated at reflux for 30 hours. The mixture was allowed to cool and the solids removed by filtration. The volatiles were removed from the filtrate by evaporation and the residue triturated with hexane to give ethyl 3-methoxy-4-(2-methoxyethoxy)benzoate (11.3 g, 89%) as a white solid.

m.p. 57–60° C.

$^1$H NMR Spectrum: ($DMSOd_6$) 1.31(t, 3H); 3.29(s, 3H); 3.32(s, 3H); 3.68(m, 2H); 4.16(m, 2H); 4.28(q, 2H); 7.06(d, 1H); 7.45(d, 1H); 7.56(dd, 1H)

MS-FAB: 255 [MH]$^+$

Ethyl 3-methoxy-4-(2-methoxyethoxy)benzoate (9.5 g, 37 mmol) was added in portions to stirred concentrated nitric acid (75 ml) at 0° C. The mixture was allowed to warm to ambient temperature and stirred for a further 90 minutes. The mixture was diluted with water and extracted with methylene chloride, dried ($MgSO_4$) and the solvent removed by evaporation. The residue was triturated with hexane to give ethyl 5-methoxy-4-(2-methoxyethoxy)-2-nitrobenzoate (10.6 g, 95%) as an orange solid.

m.p. 68–69° C.

$^1$H NMR Spectrum: ($DMSOd_6$) 1.27(t, 3H); 3.30(s, 3H); 3.69(m, 2H); 3.92(s, 3H); 4.25(m, 2H); 4.29(q, 2H); 7.30(s, 1H); 7.65(s, 1H)

MS-CI: 300 [MH]$^+$

A mixture of ethyl 5-methoxy-4-(2-methoxyethoxy)-2-nitrobenzoate (10.24 g, 34 mmol), cyclohexene (30 ml) and 10% palladium-on-charcoal catalyst (2.0 g) in methanol (150 ml) was heated at reflux for 5 hours. The reaction mixture was allowed to cool and diluted with methylene chloride. The catalyst was removed by filtration and the volatiles removed from the filtrate by evaporation. The residue was recrystallised from ethyl acetate/hexane to give ethyl 2-amino-5-methoxy-4-(2-methoxyethoxy) benzoate (8.0 g) as a buff solid. Formamide (80 ml) was added to this product and the mixture heated at 170° C. for 18 hours. About half the solvent was removed by evaporation under high vacuum and the residue was left to stand overnight. The solid product was collected by filtration, washed with ether and dried to give 6-methoxy-7-(2-methoxyethoxy)-3,4-dihydroquinazolin-4-one (5.3 g, 62% over two steps) as a grey solid.

$^1$H NMR Spectrum: (DMSOd$_6$) 3.35(s, 3H); 3.74(m, 2H); 3.89(s, 3H); 4.26(m, 2H); 7.15(s, 1H); 7.47(s, 1H); 7.98(s, 1H); 12.03(br s, 1H)

MS-CI: 251 [MH]$^+$

DMF (0.5 ml) was added to a mixture of 6-methoxy-7-(2-methoxyethoxy)-3,4-dihydroquinazolin-4-one (5.1 g, 20 mmol) in thionyl chloride (50 ml). The mixture was stirred and heated at reflux for 3 hours, allowed to cool and the excess thionyl chloride removed by evaporation. The residue was suspended in methylene chloride and washed with aqueous sodium hydrogen carbonate solution. The aqueous phase was extracted with methylene chloride and the combined extracts dried (MgSO$_4$). The crude product was recrystallised from methylene chloride/hexane to give 4-chloro-6-methoxy-7-(2-methoxyethoxy)quinazoline (2.8 g, 51%) as a fine white solid.

$^1$H NMR Spectrum: (DMSOd$_6$) 3.37(s, 3H); 3.77(m, 2H); 4.01(s, 3H); 4.37(m, 2H); 7.40(s, 1H); 7.49(s, 1H); 8.88(s, 1H)

MS-CI: 269 [MH]$^+$

A suspension of 7-azaoxindole hydrobromide (800 mg, 3.7 mmol), (Tet.Let. 1987, 28, 4027), in methylene chloride (10 ml) was adjusted to pH9 with saturated aqueous sodium hydrogen carbonate solution. The organic layer was separated and the aqueous layer was extracted with methylene chloride. The organic layers were combined, washed with brine, dried (MgSO$_4$) and the volatiles removed by evaporation. The residue was purified by column chromatography eluting with methylene chloride/methanol (95/5) to give 7-azaoxindole free base (238 mg, 48%).

EXAMPLE 3

A solution of 7-azaoxindole (284 mg, 2.1 mmol), (prepared as described for the starting material in Example 2), in THF (10 mn) was added to a suspension of sodium hydride (112 mg, 2.8 mmol, prewashed with petroleum ether) in THF (6 ml). After stirring for 20 minutes at ambient temperature, a solution of 4-chloro-6-methoxy-7-(3-morpholinopropoxy)quinazoline (238 mg, 0.7 mmol) in a mixture of THF (3 ml) and DMF (1 ml) was added. After stirring for 1 hour at 65° C., the volatiles were removed by evaporation. The residue was partitioned between water and ether. The aqueous layer was separated and adjusted to pH7 with 2M hydrochloric acid. After evaporation of water, the precipitate was triturated with ether, collected by filtration, washed with ether, and dried under vacuum. The residue was purified by column chromatography eluting with methylene chloride/methanol (9515 followed by 90110). After evaporation of the solvent, the residue was suspended in methylene chloride/methanol (1/1) and 3M hydrogen chloride in ether was added. After removal of the solvent by evaporation, the solid was collected by filtration, washed with ether and dried under vacuum to give 4-(7-azaoxindol-3-yl)-6-methoxy-7-(3-morpholinopropoxy)quinazoline (150 mg, 51%).

$^1$H NMR Spectrum: (DMSOd$_6$, CF$_3$COOD) 2.25–2.35(m, 2H); 3.1–3.2(m, 2H); 3.3–3.4(m, 2H); 3.5–3.6(d, 2H); 3.8(t, 2H); 3.95(s, 3H); 4.05(d, 2H); 4.35(t, 2H); 7.3(m, 2H); 7.95(d, 1H); 8.5–8.7(m, 2H); 8.85(s, 1H)

MS-ESI: 436 [MH]$^+$

Elemental analysis: Found C, 52.9; H, 5.8; N, 13.2% C$_{23}$H$_2$N$_5$O$_4$ 1.2HCl 0.9H$_2$O Requires C, 53.0; H, 5.6; N, 13.4%

The starting material was prepared as follows:

A mixture of 4-hydroxy-3-methoxybenzoic acid (4.5 g, 26.8 mmol), 3-morpholinopropyl chloride (9.5 g, 58.0 mmol), (prepared according to J. Am. Chem. Soc. 1945, 67, 736), potassium carbonate (8.0 g, 58 mmol), potassium iodide (1.0 g, 0.22 mmol) and DMF (80 ml) was stirred and heated at 100° C. for 3 hours. The solid was removed by filtration and the volatiles were removed from the filtrate by evaporation. The residue was dissolved in ethanol (50 ml), 2M sodium hydroxide (50 ml) was added and the mixture was heated at 90° C. for 2 hours. After partial evaporation, the mixture was acidified with concentrated hydrochloric acid, washed with ether and then subjected to purification on a Diaion (trade mark of Mitsubishi) HP20SS resin column, eluting with water and then with a gradient of methanol (0 to 25%) in hydrochloric acid (pH2). Partial evaporation of the solvents and lyophilisation gave 3-methoxy-4-(3-morpholinopropoxy)benzoic acid (8.65 g, 97%).

$^1$H NMR Spectrum: (DMSOd$_6$, TFA) 2.17–2.24(m, 2H); 3.10–3.16(m, 2H); 3.30(t, 2H); 3.52(d, 2H); 3.71 (t, 2H); 3.82(s, 3H); 4.01(br d, 2H); 4.14(t, 2H); 7.08(d, 1H); 7.48(d, 1H); 7.59(dd, 1H)

MS-ESI: 296 [MH]$^+$

Fuming nitric acid (1.5 ml, 36.2 mmol) was added slowly at 0° C. to a solution of 3-methoxy-4-(3-morpholinopropoxy)benzoic acid (7.78 g, 23.5 mmol) in TFA (25 ml). The cooling bath was removed and the reaction mixture stirred at ambient temperature for 1 hour. The TFA was evaporated and ice was added to the residue. The precipitate was collected by filtration and washed with a minimum of water followed by toluene and ether. The solid was dried under vacuum over phosphorus pentoxide to give 5-methoxy-4-(3-morpholinopropoxy)-2-nitrobenzoic acid trifluoroacetate (7.54 g, 71%yield) which was used without further purification.

$^1$H NMR Spectrum: (DMSOd$_6$, TFA) 2.16–2.23(m, 2H); 3.10–3.17(m, 2H); 3.30(t, 2H); 3.52(d, 2H); 3.66(t, 2H); 3.93(s, 3H); 4.02(br d, 2H); 4.23(t, 2H); 7.34(s, 1H); 7.61(s, 1H)

MS-EI: 340 [M]$^+$

Thionyl chloride (15 ml) and DMF (0.05 ml) were added to 5-methoxy-4-(3-morpholinopropoxy)-2-nitrobenzoic acid trifluoroacetate (7.54 g, 16.6 mmol). The mixture was heated at 50° C. for 1 hour, the excess thionyl chloride was removed by evaporation and by azeotroping with toluene (x2). The resulting solid was suspended in THF (200 ml) and ammonia was bubbled through the mixture for 30 minutes. The precipitate was removed by filtration, washed with THF and discarded. After concentration of the filtrate by evaporation, the product crystallised and was collected by filtration to give 5-methoxy-4-(3-morpholinopropoxy)-2-nitrobenzamide (5.25 g, 93%yield) as light yellow crystals which were used without further purification.

$^1$H NMR Spectrum: (DMSOd$_6$, TFA) 2.17–2.24(m, 2H); 3.11–3.18(m, 2H); 3.31(t, 2H); 3.53(d, 2H); 3.67(t, 2H); 3.93(s, 3H); 4.03(br d, 2H); 4.21(t, 2H); 7.17(s, 1H); 7.62(s, 1H)

MS-EI: 339 [M]$^+$

Concentrated hydrochloric acid (30 ml) was added to a suspension of 5-methoxy-4-(3-morpholinopropoxy)-2- nitrobenzamide (5.67 g, 16.7 mmol) in methanol (150 ml) and the mixture was heated to 60° C. When the 5-methoxy-4-(3-morpholinopropoxy)-2-nitrobenzamide had dissolved, iron powder (5.6 g, 100 mmol) was added in portions to the reaction mixture which was then heated at 60° C. for 90 minutes. After cooling, the insolubles were removed by filtration through diatomaceous earth, the volatiles were removed from the filtrate by evaporation and the residue was purified on a Diaion (trade mark of Mitsubishi) HP20SS resin colurnn, eluting with water and then with hydrochloric acid (pH2). Concentration of the fractions by evaporation gave a precipitate which was collected by filtration and dried under vacuum over phosphorus pentoxide to give 2-amino-5-methoxy4-(3-morpholinopropoxy)benzamide as a hydrochloride salt (4.67 g, 75%) as beige crystals.

$^1$H NMR Spectrum: (DMSOd$_6$, TFA) 2.22–2.28(m, 2H); 3.12(br t, 2H); 3.29(t, 2H); 3.51(d, 2H); 3.75(t, 2H); 3.87(s, 3H); 4.00(br d, 2H); 4.12(t, 2H); 7.06(s, 1H); 7.53(s, 1H)

MS-EI: 309 [M]$^+$

A mixture of 2-amino-5-methoxy-4-(3-morpholinopropoxy)benzamide (4.57 g, 12.25 mmol) and Gold's reagent (2.6 g, 15.89 mmol) in dioxane (35 ml) was heated at reflux for 5 hours. Acetic acid (0.55 ml) and sodium acetate (1.0 g) were added to the reaction mixture which was heated at reflux for a further 3 hours. The mixture was cooled to ambient temperature and the volatiles removed by evaporation. The residue was adjusted to pH7 with 2M sodium hydroxide and then purified on a Diaion (trade mark of Mitsubishi) HP20SS resin column, eluting with methanol (gradient of 0 to 60%) in water. Concentration of the fractions by evaporation gave a precipitate which was collected by filtration and dried under vacuum over phosphorus pentoxide to give 4-hydroxy-6-methoxy-7-(3-morpholinopropoxy)quinazoline (3.04 g, 78%) as a white solid.

$^1$H NMR Spectrum: (CDCl$_3$) 2.10(q, 2H); 2.48(m, 4H); 2.56(t, 2H); 3.72(t, 4H); 4.00(s, 3H); 4.24(t, 2H); 7.18(s, 1H); 7.60(s, 1H); 8.00(s, 1H); 10.86(br s, 1H)

MS-EI: 319 [M]$^+$

A mixture of 4-hydroxy-6-methoxy-7-(3-morpholinopropoxy)quinazoline (638 mg, 2 mmol) and thionyl chloride (8 ml) was heated at reflux for 30 minutes. Excess thionyl chloride was removed by evaporation and by azeotroping with toluene (x2). The residue was suspended in methylene chloride and a 10% aqueous solution of sodium hydrogen carbonate (50 ml) was added to the mixture. The organic layer was separated, dried (MgSO$_4$) and the solvent removed by evaporation. The residue was triturated with ether, the solid was collected by filtration, washed with ether and dried under vacuum to give 4-chloro-6-methoxy-7-(3-morpholinopropoxy)quinazoline (590 mg, 87%).

$^1$H NMR Spectrum: (CDCl$_3$) 2.10–2.16(m, 2H); 2.48(br s, 4H); 2.57(t, 2H); 3.73(t, 4H); 4.05(s, 3H); 4.29(t, 2H); 7.36(s, 1H); 7.39(s, 1H); 8.86(s, 1H)

MS-ESI: 337 [MH]$^+$

EXAMPLE 4

A solution of 7-azaoxindole (170 mg, 1.27 mmol), (prepared as described for the starting material in Example 2), in THF (3 ml) was added to a suspension of sodium hydride (51 mg, 1.27 mmol, prewashed with hexane) in THF (3 ml). After stirring for 30 minutes at ambient temperature, a solution of 4-chloro-6-methoxy-7-(2-(pyrrolidin 1-yl) ethoxyquinazoline (130 mg, 0.42 mmol) in DMF (2 ml) was added. After heating at 60° C. for 30 minutes, the volatiles were removed by evaporation. The residue was partitioned between methylene chloride and water. The aqueous layer was adjusted to pH2 with 2M hydrochloric acid. The aqueous layer was evaporated. The residue was suspended in water and the aqueous layer was adjusted to pH9 with 2M sodium hydroxide and extracted with methylene chloride. The organic layer was washed with brine, dried (MgSO$_4$) and evaporated. The residue was purified by chromatography on neutral alumina eluting with a gradient of methylene chloride/methanol (9/10 to 1/9). After evaporation of the solvent, the residue was dissolved in methylene chloride/methanol (1/1) and 2M hydrogen chloride in methanol was added. The volatiles were removed by evaporation and the residue was triturated with ether, collected by filtration and dried under vacuum to give 4-(7-azaoxindol-3-yl)-6-methoxy-7-(2-(pyrrolidin-1-yl)ethoxy)quinazoline (33 mg, 18%).

$^1$H NMR Spectrum: (DMSOd$_6$, NaOD, D$_2$O) 1.7(br s, 4H); 2.6(s, 4H); 2.9(t, 2H); 3.85(s, 3H); 4.2(t, 2H); 6.4(dd, 1H); 6.9(s, 1H); 7.4(d, 1H); 7.95(d, 1H); 8.35(s, 1H); 9.1(s, 1H)

MS-ESI: 406 [MH]$^+$

Elemental analysis: Found C, 48.2; H, 5.7; N, 12.7% C$_{22}$H$_{23}$N$_5$O$_3$ 2HCl 3.7H$_2$O Requires C, 48.5; H, 6.0; N, 12.8%

The starting material was prepared as follows:

A mixture of 2-amino-4-benzyloxy-5-methoxybenzamide (10 g, 0.04 mol), (J. Med. Chem. 1977, vol 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated at reflux for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The mixture was evaporated and azeotroped with toluene to give 7-benzyloxy-4-chloro-6-methoxyquinazoline hydrochloride (3.35 g). 7-Benzyloxy-4-chloro-6-methoxyquinazoline hydrochloride (3.35 g) was dissolved in methylene chloride (250 ml) and washed with sodium hydrogen carbonate until the aqueous layer was adjusted to pH8. The organic layer was washed with brine, dried (MgSO$_4$) and evaporated to give 7-benzyloxy-4-chloro-6-methoxyquinazoline (2.9 g, 96%).

Sodium hydride (400 mg of an 80% suspension in paraffin oil, 13.3 mmol) was added to a solution of phenol (1.26 g, 13.3 mmol) in dry 1-methyl-2-pyrrolidinone (20 ml) and the mixture stirred for 10 minutes. 7-Benzyloxy-4-chloro-6-methoxyquinazoline (1.6 g, 5.3 mmol), was then added and the reaction mixture heated at 110° C. for 2 hours. The mixture was allowed to cool, water was added and the mixture extracted with ethyl acetate (3×100 ml). The combined extracts were then washed with 2M sodium hydroxide solution, water and brine. Removal of the solvent under reduced pressure gave 7-benzyloxy-6-methoxy4-phenoxyquinazoline (1.6 g, 84%) as a yellowish solid.

$^1$H NMR Spectrum: (DMSOd$_6$) 3.98(s, 3H); 5.37(s, 2H); 7.25–7.6(m, 1H); 7.60(s, 1H); 8.54(s, 1H)

MS-ESI: 300 [MH]$^+$

7-Benzyloxy-6-methoxy-4-phenoxyquinazoline (160 mg, 0.44 mmol) in TFA (3 ml) was heated at reflux for 30 minutes. The solvent was removed by evaporation and the residue treated with aqueous sodium hydrogen carbonate solution. The precipitated product was collected by filtration, washed with water and dried to give 7-hydroxy-6-methoxy-4-phenoxyquinazoline (105 mg, 88%).

$^1$H NMR Spectrum: (DMSOd$_6$) 4.00(s, 3H); 7.20(s, 1H); 7.25–7.35(m, 3H); 7.4–7.55(m, 2H); 7.58(s, 1H); 10.73(s, 1H)

MS-ESI: 269 [MH]$^+$ 1-(2-Chloroethyl)pyrrolidine hydrochloride (1.27 g, 7.5 mmol) was added to 7-hydroxy-6-methoxy-4-phenoxyquinazoline (1.0 g, 3.7 mmol), and potassium carbonate (3.9 g, 28.3 mmol) in DMF (30 ml). The mixture was heated at 110° C. for 4 hours and allowed to cool. The mixture was filtered, and the volatiles were removed from the filtrate by evaporation. The residue was purified by column chromatography eluting with methylene chloride/methanol/ammonia, (100/8/1) to give an oil which was triturated with ethyl acetate to give 6-methoxy-4-phenoxy-7-(2-(pyrrolidin-1-yl)ethoxy)quinazoline (200 mg, 15%) as a white solid.

$^1$H NMR Spectrum: (DMSOd$_6$) 1.65(m, 4H); 2.55(m, 4H); 2.85(t, 2H); 3.95(s, 3H); 4.25(t, 2H); 7.30(m, 3H); 7.38(s, 1H); 7.50(m, 2H); 7.55(s, 1H); 8.5(s, 1H)

MS-ESI: 366 [MH]$^+$

A mixture of 6-methoxy-4-phenoxy-7-(2-(pyrrolidin-1-yl)ethoxy)quinazoline (565 mg, 1.55 mmol) and 2M hydrochloric acid (5 ml) was heated at 90° C. for 90 minutes and allowed to cool. The solution was neutralised with aqueous sodium hydrogen carbonate, and the water removed by evaporation. The residue was purified by column chromatography eluting with methylene chloride/methanol/ammonia (100/8/1) to give 6-methoxy-7-(2-(pyrrolidin-1-yl)ethoxy)-3,4-dihydroquinazolin-4-one (440 mg, 98%yield). This material was used without further characterisation.

A solution of 6-methoxy-7-(2-(pyrrolidin-1-yl)ethoxy-3,4-dihydroquinazolin-4-one (909 mg, 3.14 mmol) in thionyl chloride (12 ml) containing DMF (0.5 ml) was refluxed for I hour. After cooling toluene was added and the volatiles were removed by evaporation. The residue was partitioned between methylene chloride and water and the aqueous layer was adjusted to pH8 with sodium hydrogen carbonate. The organic layer was separated, washed with brine, dried (MgSO$_4$), filtered and evaporated. The residue was purified by flash chromatography eluting with methylene chloride/methanol (95/5 followed by 85/15). The residue was triturated with ether, collected by filtration and dried under vacuum to give 4-chloro-6-methoxy-7-(2-(pyrrolidin-1-yl)ethoxyquinazoline (638 mg, 66%).

$^1$H NMR Spectrum: (DMSOd6) 1.7(br s, 4H); 2.56(br s, 4H); 2.9(t, 2H); 4.0(s, 3H); 4.32(t, 2H); 7.4(s, 1H); 7.48(s, 1H); 8.9(s, 1H)

MS-ESI: 308 [MH]$^+$

EXAMPLE 5

A solution of 7-azaoxindole (165 mg, 1.23 mmol), (prepared as described for the starting material in Example 2), in DMF (3 ml) was added dropwise to a suspension of sodium hydride (50 mg, 1.23 mmol, prewashed with hexane) in DMF (3 ml). After stirring for 30 minutes at ambient temperature, 4-chloro-7-(2-(imidazol-1-yl)ethoxy)-6-methoxyquinazoline (125 mg, 0.41 mmol) in DMF (3 ml) was added. The mixture was heated at 65° C. for 30 minutes. After cooling the mixture was partitioned between saturated aqueous ammonium chloride and methylene chloride. The precipitate was collected by filtration, dried and purified by flash chromatography eluting with methylene chloride/methanol (8/2). After evaporation of the solvent, the solid was dissolved in methylene chloride/methanol and 2.2 M hydrogen chloride in ether was added. After stirring for 10 minutes at ambient temperature, the volatiles were removed by evaporation. The residue was triturated with ether, collected by filtration and dried under vacuum to give 4-(7-azaoxindol-3-yl)-7-(2-(imidazol-1-yl)ethoxy)-6-methoxyquinazoline (110 mg, 53%).

$^1$H NMR Spectrum: (DMSOd$_6$, CF$_3$COOD) 3.89(s, 3H); 4.65(t, 2H); 4.8(t, 2H); 7.29(d, 1H); 7.31(s, 1H); 7.73(s, 1H); 7.84(s, 1H); 7.92(d, 1H); 8.5–8.6(m, 1H); 8.65–8.70(m, 1H); 8.71(s, 1H);9.22(s, IH)

MS-ESI: 403 [MH]$^+$

Elemental analysis: Found C, 49.3; H, 4.4; N, 16.3% C$_{21}$H$_{18}$N$_6$O$_3$ 1.8H$_2$O 2.1HCl Requires C, 49.3; H, 4.7; N, 16.4%

The starting material was prepared as follows:

A mixture of 2-amino-4-benzyloxy-5-methoxybenzamide (10 g, 0.04 mol), (J. Med. Chem. 1977, vol 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated at reflux for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol) in DMF (70 ml) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (100 ml) and poured onto ice/water (400 ml) and 2M hydrochloric acid (4 ml). The organic layer was separated and the aqueous layer extracted with ethyl acetate, the combined extracts were washed with brine, dried (MgSO$_4$) and the volatiles removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: (DMSOd$_6$) 1.11(s, 9H); 3.89(s, 3H); 5.3(s, 2H); 5.9(s, 2H); 7.27(s, 1H); 7.35(m, 1H); 7.47(t, 2H); 7.49(d, 2H); 7.51(s, 1H); 8.34(s, 1H)

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the volatiles removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: (DMSOd$_6$) 1.1(s, 9H); 3.89(s, 3H); 5.89(s, 2H); 7.0(s, 1H); 7.48(s, 1H); 8.5(s, 1H)

Diethyl azodicarboxylate (435 mg, 2.5 mmol) was added dropwise to a suspension of 7-hydroxy-6-methoxy-3-

((pivaloy(oxy)methyl)-3,4-dihydroquinazolin-4-one (612 mg, 2 mmol), 2-(imidazol-1-yl)ethanol (280 mg, 2.5 mmol), (J. Med. Chem. 1993, 25, 4052–4060), and triphenylphosphine (655 mg, 2.5 mmol) in methylene chloride (10 ml) at 5° C. The mixture was stirred for 10 minutes at 5° C. and then for 1 hour at ambient temperature. The mixture was poured directly on to a silica column and eluted with methylene chloride/methanol (95/5) to give 7-(2-(imidazol-1-yl)ethoxy)-6-methoxy-3-((pivaloyloxy)methyl)-3,4-dihydroquinazolin-4-one (640 mg, 80%).

$^1$H NMR Spectrum: (CDCl$_3$) 1.19(s, 9H); 3.98(s, 3H); 4.34(m, 2H); 4.45(m, 2H); 5.94(s, 2H); 7.02(s, 1H); 7.07(s, 1H); 7.1 1(s, 1H); 7.64(s, 1H); 7.67(s, 1H); 8.17(s, 1H)

MS-ESI: 423 [MNa]$^+$

Elemental Analysis: Found C, 58.3; H, 6.4; N, 13.9% C$_{20}$H$_{24}$N$_4$O$_5$ 0.7H$_2$O Requires C, 58.2; H, 6.2; N, 13.6%

A solution of 7-(2-(imidazol-1-yl)ethoxy)-6-methoxy-3-((pivaloyloxy)methyl)-3,4-dihydroquinazolin-4-one (640 mg, 1.6 mmol) in saturated methanolic ammonia (10 ml) was stirred for 15 hours at ambient temperature. The volatiles were removed by evaporation, the solid was triturated with ether, collected by filtration and dried under vacuum to give 7-(2-(imidazol-1-yl)ethoxy)-6-methoxy-3,4-dihydroquinazolin-4-one (412 mg, 90%).

$^1$H NMR Spectrum: (DMSOd$_6$) 3.89(s, 3H); 4.4–4.5(m, 4H); 6.9(s, 1H); 7.16(s, 1H); 7.28(s, 1H); 7.47(s, 1H); 7.7(s, 1H); 7.99(s, 1H)

MS-ESI: 287 [MH]$^+$

Elemental Analysis: Found C, 57.8; H, 5.2; N, 19.3% C$_{14}$H$_{14}$N$_4$O$_3$ 0.3H$_2$O Requires C, 57.7; H, 5.1; N, 19.2%

A mixture of 7-(2-(imidazol-1-yl)ethoxy)-6-methoxy-3,4-dihydroquinazolin-4-one (412 mg, 1.44 mmol), thionyl chloride (5 ml) and DMF (0.2 ml) was heated at reflux for 1 hour. The mixture was diluted with toluene and the volatiles were removed by evaporation. The residue was suspended in methylene chloride, cooled to 0° C. and aqueous sodium hydrogen carbonate solution was added. The resulting precipitate was collected by filtration and dried under vacuum to give 4-chloro-7-(2-(imidazol-1-yl)ethoxy)-6-methoxyquinazoline (258 mg, 59%).

$^1$H NMR Spectrum: (DMSOd$_6$) 4.01(s, 3H); 4.47(m, 2H); 4.53(m, 2H); 6.89(s, 1H); 7.27(s, 1H); 7.41(s, 1H); 7.49(s, 1H); 7.70(s, 1H); 8.88(s, 1H)

MS-ESI: 327 [MNa]$^+$

EXAMPLE 6

5,7-Diaza-6-methyloxindole (1.3 g, 8.7 mmol) was added dropwise to a suspension of sodium hydride (500 mg, 8.3 mmol, prewashed with hexane) in DMF (100 ml). After stirring for 20 minutes at ambient temperature, 4-chloro-7-(3-morpholinopropoxy)quinazoline (1.6 g, 5.2 mmol) in DMF (10 ml) was added and the mixture was heated at 70° C. for 1 hour. After cooling, the mixture was diluted with water and adjusted to pH1 with 2M hydrochloric acid. The mixture was extracted with ether. The aqueous layer was basified with aqueous sodium hydrogen carbonate and the precipitate was collected by filtration, washed with water, ether and dried under vacuum. The solid was purified by flash chromatography eluting with methylene chloride/methanol (90/10 followed by 80/20) to give a solid. The solid was dissolved in methylene chloride/methanol (1/1) and 5M hydrogen chloride in methanol (0.5 ml) was added. The solution was concentrated to a total volume of 2 ml and ether (15 ml) was added. The solid was filtered, washed with ether and dried under vacuum to give 4-(5,7-diaza-6-methyloxindol-3-yl)-7-(3-morpholinopropoxy)quinazoline (1.29 g, 59%).

$^1$H NMR Spectrum: (DMSOd$_6$, CF$_3$COOH) 2.2(m, 2H); 2.65(s, 3H); 3.1(m, 2H); 3.3(t, 2H); 3.5(d, 2H); 3.6(t, 2H); 4.0(d, 2H); 4.2(t, 2H); 7.05(d, 1H); 7.2(dd, 1H); 8.7(s, 1H); 8.95(s, 1H); 9.6(m, 1H); 9.9(m, 1H); 12.3(s, 1H)

MS-ESI: 421 [MH]$^+$

Elemental analysis: Found C, 51.1; H, 5.3; N, 16.1% C$_{22}$H$_{24}$N$_6$O$_3$ 2HCl 1.2H$_2$O Requires C, 51.3; H, 5.6; N, 16.3%

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water 1/1 (250 ml). The precipitated solid was collected by filtration, washed with water and dried to give 7-fluoro-3,4-dihydroquinazolin-4-one (2.6 g, 82%).

Sodium metal (4.4 g, 19 mmol) was added to benzyl alcohol (100 ml) at ambient temperature and the mixture stirred for 30 minutes then heated at 80° C. for 1 hour. The mixture was then cooled to 40° C. and 7-fluoro-3,4-dihydroquinazolin-4-one (7.8 g, 47 mmol) was added. The reaction mixture was stirred at 130° C. for 4 hours and allowed to cool to ambient temperature and stirred for 18 hours. The solution was quenched with water (800 ml) and acidified to pH3 with concentrated hydrochloric acid. The resulting precipitate was collected by filtration, washed with water and ether and dried for 4 hours at 60° C. under high vacuum to give 7-benzyloxy-3,4-dihydroquinazolin-4-one (7.02 g, 63%). 7-Benzyloxy-3,4-dihydroquinazolin-4-one (7.0 g, 27 mmol) was suspended in dry DMF (50 ml) and sodium hydride was added (1.22 g of a 60% suspension in mineral oil, 30 mmol). The reaction mixture was allowed to return to ambient temperarture, chloromethyl pivalate (4.75 g, 31.5 mmol) was added over 10 minutes and the mixture was stirred for 1 hour. The reaction mixture was quenched into water (250 ml), the aqueous phase adjusted to pH5 with 2M hydrochloric acid and extracted with ether (3×300 ml). The combined ether phases were washed with brine, dried (MgSO$_4$) and the volatiles were removed by evaporation. The solid residue was triturated with isohexane, collected by filtration and dried under vacuum to give 7-benzyloxy-3-((pivaloyloxy)methyl)-3,4-dihydroquinazolin-4-one (9.1 g, 90%). 7-Benzyloxy-3-((pivaloyloxy)methyl)-3,4-dihydroquinazolin-4-one (8.0 g, 22 mmol) was dissolved in TFA (40 ml) and the mixture was heated at reflux for 3 hours then allowed to cool to ambient temperature and stirred for 18 hours. The TFA was removed by evaporation and the residue resuspended in a mixture of ether and aqueous sodium hydrogen carbonate solution. The solid was collected by filtration, washed with water and ether and dried at 40° C. for 3 hours under high vacuum to give 7-hydroxy-3-((pivaloyloxy)methyl)-3,4-dihydroquinazolin-4-one (5.42 g, 90%).

Morpholine (94 g, 1.08 mol) was added dropwise to a solution of 3-bromo-1-propanol (75 g, 0.54 mol) in toluene (750 ml) and the reaction then heated at 80° C. for 4 hours. The mixture was allowed to cool to ambient temperature and the precipitated solid was removed by filtration. The volatiles were removed from the filtrate and the resulting yellow oil was purified by distillation at 0.4–0.7 mmHg to give 4-(3-hydroxypropyl)morpholine (40 g, 50%) as a colourless oil.

b.p. 68–70° C. (~0.5 mmHg)

$^1$H NMR Spectrum: (DMSOd$_6$) 1.65–1.78(m, 2H); 2.50(t, 4H); 2.60(t, 2H); 3.68(t, 4H); 3.78(t, 2H); 4.90(br d, 1H)

7-Hydroxy-3-((pivaloyloxy)methyl)-3,4-dihydroquinazolin-4-one (750 mg, 2.7 mmol) was suspended in methylene chloride (40 ml) at 5° C. and 4-(3-hydroxypropyl)morpholine (490 mg, 3.4 mmol) and triphenylphosphine (890 mg, 3.4 mmol) were added. The mixture was stirred for 5 minutes and diethyl azodicarboxylate (590 mg, 3.4 mmol) was added over 5 minutes at 5° C. The reaction mixture was stirred at 5° C. for 30 minutes then at ambient temperature for 1 hour. The solution was then purified directly by column flash chromatography eluting with methylene chloride, and then ethyl acetate, acetonitrile/ethyl acetate (20/80), and acetonitrile/ethyl acetate/ammonia (50/50/0.5). The purified product was triturated with ether/isohexane and collected by filtration to give 7-(3-morpholinopropoxy)-3-((pivaloyloxy)methyl)-3,4-dihydroquinazolin4-one (745 mg, 68%).

7-(3-Morpholinopropoxy)-3-((pivaloyloxy)methyl)-3,4-dihydroquinazolin4-one (680 mg, 1.6 mmol) was stirred in methanolic ammonia (20 ml) at 40° C. for 6 hours then for 18 hours at ambient temperature. The solvent was removed by evaporation, the residue was triturated with ether/isohexane and collected by filtration to give 7-(3-morpholinopropoxy)-3,4-dihydroquinazolin-4-one (450 mg, 92%) as a white solid.

$^1$H NMR Spectrum: (DMSOd$_6$) 1.9(quin, 2H); 2.35(t, 4H); 2.4(t, 2H); 3.55(t, 4H); 4.15(t, 2H); 7.05(m, 2H); 7.97(d, 1H); 8.02(s, 1H)

MS: 290 [MH]$^+$

A mixture of 7-(3-morpholinopropoxy)-3,4-dihydroquinazolin-4-one (500 mg, 1.7 mmol), thionyl chloride (10 ml) and DMF (0.1 ml) was heated at reflux for 2 hours. The volatiles were removed by evaporation and the residue azeotroped with toluene. The crude product was partitioned between methylene chloride (50 ml) and saturated aqueous sodium hydrogen carbonate solution (50 ml) and the mixture was stirred for 10 minutes. The organic phase was separated and the aqueous phase extracted with methylene chloride. The combined extracts were dried (MgSO$_4$) and the solvent removed by evaporation to give 4-chloro-7-(3-morpholinopropoxy)quinazoline (425 mg, 80%).

Sodium hydride (10 g of a 60% suspension in oil, 0.25 mol) was suspended in toluene (100 ml) and diethyl succinate (40 g, 0.23 mol) was added followed by ethyl formate (21 g, 0.285 mol). No reaction seemed to take place during the first 30 minutes then the temperature slowly rose to 35° C. at which point a strong exotherm was recorded with the temperature rising to 90° C. over a few minutes. Once the reaction mixture had cooled to ambient temperature, acetamidine hydrochloride (21 g, 0.22 mol) in 2-propanol (250 ml) was added and the solution heated at reflux for 4 hours. The reaction mixture was directly adsorbed onto 100 g of silica and the solvents removed by rotary evaporation under vacuum. The free flowing powder was poured on the top of a flash chromatography column pre-equilibrated with 5% methanol in ethyl acetate. The polarity of the solvent was gradually increased to 15% methanol in ethyl acetate to give ethyl (2-methyl-4-hydroxypyrimidin-5-yl) acetate (21.3 g, 51%). 5 Ethyl (2-methyl-4-hydroxypyrimidin-5-yl) acetate (19.2 g, 99 mmol) and phosphorus oxychloride (75 ml) were heated at 80° C. for 2 hours to give an orange solution. The phosphorus oxychloride was removed by rotary evaporation under vacuum and the residual oil was partitioned between methylene chloride (100 ml), sodium hydrogen carbonate (250 ml of a saturated solution) and ice. More sodium hydrogen carbonate was added until the pH remained at about 8 after a few minutes of stirring. The methylene chloride was separated and the aqueous phase re-extracted again with methylene chloride. The organic phases were combined, washed once with a saturated solution of sodium hydrogen carbonate and brine (1/1) and dried by filtration through a phase separator filter paper (Whatman). Removal of the volatiles by evaporation gave ethyl (2-methyl-4-chloropyrimidin-5-yl) acetate (20.3 g, 96%) as an orange oil.

Ethyl (2-methyl-4-chloropyrimidin-5-yl) acetate (19.9 g, 93 mmol) was dissolved in DMF (50 mml), sodium azide (6.5 g, 100 mmol) was added and this solution was stirred at 60–70° C. for 3 hours. The DMF was removed by evaporation and the residual oil was suspended in methylene chloride, washed once with water (250 ml), brine (250 ml) and dried by filtration through a phase separator filter paper (Whatman). Removal of the volatiles by evaporation gave ethyl (4-azido-2-methylpyrimidin-5-yl) acetate (19.6 g, 95%) as a yellow/orange oil which crystallised overnight.

Ethyl (4-azido-2-methylpyrimidin-5-yl) acetate (19.5 g, 88 mmol) was dissolved in a mixture of ethanol (100 ml) and methanol (100 ml) and 10% palladium-on-charcoal catalyst (1.5 g of a 50% suspension in water) was added. The mixture was then stirred under hydrogen at atmospheric pressure at ambient temperature for 6 hours. Methylene chloride was then added to dissolve the product and the catalyst was removed by filtration. The solvents were evaporated using a rotary evaporator and the residue was triturated with ether and collected by filtration to give ethyl (4-amino-2-methylpyrimidin-5-yl) acetate as an orange solid (16.3 g, 95%).

Ethyl (4-amino-2-methylpyrimidin-5-yl) acetate (7.2 g, 37 mmol) was suspended in Dowtherm A (14 ml) and heated at 230° C. for 3 hours. The reaction mixture was allowed to cool to about 120° C., diluted with toluene (100 ml) and stirred until the mixture returned to ambient temperature. The brown solid obtained was collected by filtration, redissolved into methylene chloride and methanol, silica (15 g) was added and the volatiles were removed by evaporation. The free flowing powder was placed on the top of a flash chromatography column pre-equilibrated in methylene chloride/methanol/ammonia (100/0 5/0.5) and the product was eluted using methylene chloride/methanol/ammonia (100/10/1). Removal of the volatiles by evaporation gave 5,7-diaza-6-methyloxindole (3.8 g, 70%).

EXAMPLE 7

Sodium hydride (83 mg, 2.1 mmol) was added to 4-aza-6-trifluoromethyloxindole (360 mg, 1.8 mmol) in DMF (7 ml) and the solution was carefully degassed using alternatively vacuum and argon. After being stirred for 15 minutes at ambient temperature, 4chloro-6-methoxy-7-(3-morpholinopropoxy)quinazoline (200 mg, 5.9 mmol), (prepared as described for the starting material in Example 3), in DMF (7 ml) was added and the reaction mixture was degassed again before being heated at 100° C. for 1 hour. Upon cooling to ambient temperature, the DMF was removed by evaporation and the residue taken up in methylene chloride (20 ml) and methanol (20 ml). Silica was added to this solution and the volatiles were removed by evaporation. The free flowing powder was placed on the top of a flash chromatography column pre-equilibrated in 100% methylene chloride. Elution was done using methylene chloride/methanol (a gradient of 100/0 to 10/1). The product was triturated with methanol and collected by filtration to give 4-(4-aza-6-trifluoromethyloxindol-3-yl) 6-methoxy-7-(3-morpholinopropoxy)quinazoline (35 mg, 12%) as an orange solid.

$^1$H NMR Spectrum: (DMSOd$_6$, TFA) 2.3(m, 2H); 3.1(m, 2H); 3.3(m, 2H); 3.5(d, 2H); 3.65(t, 2H); 4.0(m, 5H); 4.3(m, 2H); 7.3(s, 1H); 7.46(s, 1H); 8.24(s, 1H); 8.94(s, 1H); 9.7(s, 1H); 10.08(s, 1H); 11.30(s, 1H)

MS-ESI: 504 [MH]+

The starting material was prepared as follows:

Sodium hydride (880 mg, 20 mmol) was added to dibenzyl malonate (5.5 ml, 20 mmol) in anhydrous DMF (35 ml) at ambient temperature. The mixture was stirred for 15 minutes and 2-chloro-2-nitro-5-trifluoromethyl pyridine (2.5 g, 10 mmol, in 5 ml of DMF) was added and the reaction mixture stirred at ambient temperature for 1 hour. The dark red solution was then poured into ice/water and extracted with ether (500 ml). The ether phase was washed with water (4×250 ml), brine, dried (MgSO$_4$), filtered and the volatiles removed by evaporation to give a red oil. Purification by flash chromatography using isohexanes/ethyl acetate (12/1) gave dibenzyl (3-nitro-5-trifluoromethyl-2-pyridyl) malonate as a white solid (3.5 g, 67%).

Dibenzyl (3-nitro-5-trifluoromethyl-2-pyridyl) malonate (3.5 g, 7.4 mmol) was dissolved in DMSO, and lithium chloride (620 mg, 14 mmol) and water (130 mg, 7.4 mmol) were added. The reaction mixture was heated at 100° C. for 3 hours then left to cool to ambient temperature. The solution was diluted with ethyl acetate (500 ml) and washed with water and brine, dried (MgSO$_4$) and the volatiles were removed by evaporation. Purification by flash chromatography using isohexanes/ethyl acetate (17/1) gave benzyl (3-nitro-5-trifluoromethyl-2-pyridyl) acetate (2.45 g, 70%) as a pink solid.

Benzyl (3-nitro-5-trifluoromethyl-2-pyridyl) acetate (2.4 g, 7.1 mmol) was dissolved in acetic acid (15 ml), iron powder (1.58 g, 28 mmol) was added and the mixture heated at 100° C. for 1 hour. The reaction mixture was allowed to cool to ambient temperature, it was diluted with methanol and ethyl acetate and the iron salts were removed by filtration. Silica was added to the filtrate and the volatiles were removed by evaporation. The free flowing powder was placed on the top of a flash chromatography column pre-equilibrated in methylene chloride and the product was eluted using methylene chloride/methanol (25/1). Removal of the volatiles by evaporation, trituration of the solid with ether and filtration gave 4-aza-6-trifluoromethyloxindole (376 mg, 26%).

$^1$H NMR Spectrum: (DMSOd$_6$, TFA) 5.8 (s, 1H); 7.9 (s, 1H); 8.56 (s, 1H); 12.58 (s, 1H)

EXAMPLE 8

Using a procedure analogous to that described for the synthesis of Example 9, 4-methylsulphanyl-7-(3-morpholinopropoxy)quinazoline (160 mg, 0.8 mmol) was reacted with 7-aza-6-chlorooxindole (185 mg, 1.1 mmol), (prepared as described for the starting material in Example 9), in DMSO (3 ml) to give 4-(7-aza-6-chlorooxindol-3-yl)-7-(3-morpholinopropoxy)quinazoline hydrochloride (150 mg, 64%).

$^1$H NMR Spectrum: (DMSOd$_6$, CF$_3$COOD) 2.2–2.3(m, 2H); 3.05–3.15(t, 2H); 3.35(t, 2H); 3.52(d, 2H); 3.75(t, 2H); 4.0(d, 2H); 4.28(t, 2H); 7.02(d, 1H); 7.25(s, 1H); 7.25(dd, 1H); 8.0(d, 1H); 8.55(br s, 1H); 8.62(s, 1H)

MS-ESI: 440 [MH]+

The starting material was prepared as follows:

A suspension of 7-benzyloxy-3,4-dihydroquinazolin-4-one (7 g, 28 mmol), (prepared as described for the starting material in Example 6), in pyridine (350 ml) containing phosphorus pentasulphide (12.5 g, 33 mmol) was heated at reflux for 8 hours. After cooling, the mixture was poured into water (1 liter). The precipitate was collected by filtration, and washed with water. The solid was dissolved in 6M sodium hydroxide and the solution was filtered. The filtrate was acidified to pH2 with 6M hydrochloric acid. The precipitate was collected by filtration, washed with water, and dried under vacuum at 60° C. to give 7-benzyloxy-3,4-dihydroquinazolin-4-thione (7.42 g, 99%).

$^1$H NMR Spectrum: (DMSOd$_6$) 5.32(s, 2H); 7.25(d, 1H); 7.32(dd, 1H); 7.4(m, 1H); 7.45(t, 2H); 7.55(d, 2H); 8.15(s, 1H); 8.5(d, 1H)

MS-ESI: 269 [MH]+

Methyl iodide (0.97 ml, 15.4 mmol) was added dropwise to a solution of 7-benzyloxy-3,4-dihydroquinazolin-4-thione (3.45 g, 12.9 mmol) in THF (13 ml) containing 1M sodium hydroxide (25.7 ml). After stirring for 30 minutes at ambient temperature, the mixture was adjusted to pH7 with 2M hydrochloric acid. After dilution with water, the solid was collected by filtration, washed with water and dried under vacuum to give 7-benzyloxy-4-methylsulphanylquinazoline (3.3 g, 92%).

$^1$H NMR Spectrum: (DMSOd$_6$) 2.67(s, 3H); 5.32(s, 2H); 7.3–7.45(m, 5H); 7.5(d, 2H); 8.05(d, 1H); 8.9(s, 1H)

MS-ESI: 283 [MH]+

A solution of 7-benzyloxy4-methylsulphanylquinazoline (3 g, 10.6 mmol) in TFA (30 ml) was heated at reflux for 5 hours. After cooling, the volatiles were removed by evaporation. The residue was suspended in water and solid sodium hydrogen carbonate was added until complete dissolution. After extraction with ether, the aqueous layer was acidified to pH2 with 2M hydrochloric acid. The precipitate was collected by filtration, washed with water, followed by ether and dried under vacuum to give 7-hydroxy4-methylsulphanylquinazoline (2 g, quant.).

$^1$H NMR Spectrum: (DMSOd$_6$) 2.7(s, 3H); 7.15(d, 1H); 7.25(dd, 1H); 8.0(d, 1H); 8.9(s, 1H)

MS-EI: 222 [M.]+

7-Hydroxy-4-methylsulphanylquinazoline (2.5 g, 13 mmol) was suspended in methylene chloride (65 ml), triphenylphosphine (4.45 g, 17 mmol) was added followed by 4-(3-hydroxypropyl)morpholine (2.47 g, 17 mmol), (Bull Soc. Chim. Fr. 1962, 1117), and diethyl azodicarboxylate (2.92 g, 17 mmol) dropwise. After stirring for 1 hour the volatiles were removed by evaporation and the residue was partitioned between ethyl acetate/ether (20 ml/20 ml) and 1M hydrogen chloride (20 ml). The aqueous layer was separated and adjusted to pH9 with solid sodium hydrogen carbonate. The aqueous layer was extracted with methylene chloride. The organic layer was separated, washed with water, brine and dried (MgSO$_4$). The volatiles were removed by evaporation and the residue was purified by chromatography eluting with methylene chloride/ethyl acetate/methanol (6/3/1 followed by 5/3/2 and 75/0/25) to give 4-methylsulphanyl-7-(3-morpholinopropoxy)quinazoline (2.03 g 49%).

$^1$H NMR Spectrum: (DMSOd$_6$, CF$_3$COOD) 2.2–2.3(m, 2H); 2.7(s, 3H); 3.05–3.25(–m, 2H); 3.35(t, 2H); 3.55(d, 2H); 3.7(t, 2H); 4.05(d, 2H); 4.32(t, 2H); 7.38(d, 1H); 7.4(s, 1H); 8.1(d, 1H); 9.05(d, 1H)

MS-EI: 320 [MH]+

EXAMPLE 9

7-Aza 6-chlorooxindole (148 mg, 0.88 mmol) was added to a suspension of sodium hydride (40 mg, 1 mmol, pre-washed with hexane) in DMSO (2 ml). After stirring for 15 minutes at ambient temperature, 7-(2-(2-methoxyethoxy)

ethoxy)-4-methylsulphanylquinazoline (118 mg, 0.4 mmol) was added. After heating for 1.5 hours at 105° C., the volatiles were removed by evaporation. The residue was partitioned between ethyl acetate/ether (3 ml/3 ml) and saturated aqueous ammonium chloride. The emulsion was filtered. The solid was dissolved in methylene chloride/methanol and the volatiles were removed by evaporation. The residue was purified by chromatography eluting with methylene chloride/methanol (90/10) and the solvents were removed by evaporation. The solid was dissolved in methylene chloride/methanol (1/1) and 3M hydrogen chloride in ether (1 ml) was added. After removal of the volatiles, the residue was collected by filtration, washed with ether and dried under vacuum to give 4-(7-aza-6-chlorooxindol-3-yl)-7-(2-(2-methoxyethoxy)ethoxy)quinazoline hydrochloride (90 mg, 54%).

$^1$H NMR Spectrum: (DMSOd$_6$, CF$_3$COOD) 3.25(s, 3H); 3.5(t, 2H); 3.65(t, 2H); 3.85(t, 2H); 4.3(t, 2H); 7.01(d, 1H); 7.15(s, 1H); 7.3(dd, 1H); 8.0(d, 1H); 8.5(d, 1H); 8.65(s, 1H)

MS-ESI: 415 [MH]$^+$

Elemental analysis: Found C, 53.9; H, 4.6; N, 12.8% C$_{20}$H$_{19}$N$_4$O$_4$Cl 0.92HCl Requires C, 53.6; H, 4.5; N, 12.5%

The starting material was prepared as follows:

Pyridinium bromide perbromide (6.3 g, 20 mmol) was added to a solution of 7-aza-6-chloroindole (1 g, 6.6 mmol), (Synthesis 1992, 661), in 2-methyl-2-propanol (50 ml) and the mixture was stirred at ambient temperature for 3.5 hours. The volatiles were removed by evaporation and the residue was partitioned between ethyl acetate and water. The organic layer was washed with water, brine and dried (MgSO$_4$) and the volatiles were removed by evaporation to give 7-aza-6-chloro-3,3-dibromo-1,3-dihydro-2H-indol-2-one (2.1 g, 100%).

$^1$H NMR Spectrum: (CDCl$_3$) 7.16(d, 1H); 7.80(d, 1H); 8.53(br s, 1H)

Zinc powder (4.3 g, 66 mmol) was added in portions with vigorous stirring to a solution of 7-aza-6-chloro-3,3-dibromo-1,3-dihydro-2H-indol-2-one (2.17 g, 6.6 mmol) in glacial acetic acid (40 ml). After 30 minutes, the suspension was filtered, the residue was washed with acetic acid and the volatiles were removed under vacuum. The residue was suspended in water and the mixture was adjusted to pH6 with solid sodium hydrogen carbonate. The solid was collected by filtration, washed with water, followed by ether and dried under vacuum to give 7-aza-6-chlorooxindole (825 mg, 75%).

$^1$H NMR Spectrum: (DMSOd$_6$) 3.57(s, 2H); 7.03(d, 1H); 7.59(d, 1H); 11.2(br s, 1H)

MS-EI: 168 [MH]$^+$

7-Hydroxy-4-methylsulphanylquinazoline (4.8 g, 25 mmol), (prepared as described for the starting material in Example 8), was suspended in methylene chloride (100 ml), triphenylphosphine (8.51 g, 32.5 mmol) was added, followed by 2-(2-methoxyethoxy)ethanol (3.9 g, 32.5 mmol), followed by diethyl azodicarboxylate (5.66 g, 32.5 mmol) dropwise. After stirring for 1 hour at ambient temperature, the volatiles were removed under vacuum. The residue was partitionned between ether and 1M hydrogen chloride. The aqueous layer was adjusted to pH7 with solid sodium hydrogen carbonate. The aqueous layer was extracted with a mixture of ether and ethyl acetate (1/1). The organic layer was dried (MgSO$_4$), filtered and the volatiles were removed by evaporation. The residue was purified by column chromatography eluting with methylene chloride/ethyl acetate (1/1) to give after evaporation of the solvent 7-(2-(2-methoxyethoxy)ethoxy)4-methylsulphanylquinazoline (4.69 g, 63%).

$^1$H NMR Spectrum: (CDCl$_3$) 2.65(s, 3H); 3.30(s, 3H); 3.55(m, 2H); 3.65(m, 2H); 3.85(t, 2H); 4.25(t, 2H); 7.1–7.2 (m, 2H); 7.9(d, 1H); 8.85(s, 1H)

EXAMPLE 10

5,7-Diaza-6-methyloxindole (131 mg, 0.88 mmol), (prepared as described for the starting material in Example 6), was added to a suspension of sodium hydride (40 mg, 1 mnmol, prewashed with pentane) in DMF (3 ml). After stirring for 1 hour at ambient temperature 4-chloro-6-methoxy-7-(2-(1,2,3-triazol-1-yl)ethoxy)quinazoline (122 mg, 0.4 mmol) was added and the mixture was heated at 60° C. for 2 hours. After cooling, the mixture was poured into water and adjusted to pH7 with 2M hydrochloric acid. The precipitate was collected by filtration, washed with ether and dried under vacuum. The solid was purified by column chromatography eluting with methylene chloride/methanol (90/10 followed by 80120) to give, after removal of the volatiles by evaporation, an orange solid. The solid was dissolved in methylene chloride/methanol and 0.5 ml of 3M hydrogen chloride in ether was added. After removal of the solvents, the residue was collected by filtration, washed with ether and dried under vacuum to give 4-(5,7-diaza-6-methyloxindol-3-yl)-6-methoxy-7-(2-(1,2,3-triazol-1-yl) ethoxy)quinazoline hydrochloride (40 mg, 20%).

$^1$H NMR Spectrum: (DMSOd$_6$, CF$_3$COOD) 2.75(s, 3H); 3.95(s, 3H); 4.65(t, 2H); 4.95(t, 2H); 7.2(s, 1H); 7.8(s, 1H); 8.22(s, 1H); 8.8(s, 1H); 9.05(s, 1H); 9.4–9.5(br s, 1H)

MS-ESI: 419 [MH]$^+$

Elemental analysis: Found C, 46.3; H, 4.2; N, 21.6% C$_{20}$H$_{18}$N$_8$O$_3$ 1.5H$_2$O 2HCl Requires C, 46.3; H, 4.5; N, 21.6%

The starting material was prepared as follows:

Triphenylphosphine (2.82 g, 10.7 mmol) was added to a solution of 2-(1,2,3-triazol-1-yl)ethanol (609 mg, 5.4 mmol), (J. Antib. 1993, 46, 177), and 7-hydroxy-6-methoxy-3-((pivaloyloxy)methyl)-3,4-dihydroquinazolin4-one (1.1 g, 3.6 mmol), (prepared as described for the starting material in Example 5), in methylene chloride (70 ml), diethyl azodicarboxylate (600 µl, 10.7 mmol) was then added. After stirring for 2 hours at ambient temperature, the volatiles were removed by evaporation and the residue was purified by column chromatography eluting with methylene chloride/methanol (98/2) to give 6-methoxy-3-((pivaloyloxy)methyl)-7-(2-(1,2,3-triazol-1-yl)ethoxy)-3,4-dihydroquinazolin4-one (4 g, 97%).

5.1 M Ammonia in methanol (30 ml) was added to a solution of 6-methoxy-3-((pivaloyloxy)methyl)-7-(2-(1,2,3-triazol-1-yl)ethoxy)-3,4-dihydroquinazolin-4-one (1.4 g, 3.5 mmol) in a solution of methanol (30 ml). After stirring overnight at ambient temperature, the volatiles were removed by evaporation and the residue was triturated with ether, collected by filtration, washed with ether and dried under vacuum to give 6-methoxy-7-(2-(1,2,3-triazol-1-yl) ethoxy)quinazoline (946 mg, 92%).

$^1$H NMR Spectrum: (DMSOd$_6$, CF$_3$COOD) 3.9(s, 3H); 4.6(t, 2H); 4.9(t, 2H); 7.25(s, 1H); 7.52(s, 1H); 7.77(s, 1H); 8.19(s, 1H); 8.9(s, 1H)

MS-ESI: 170 [MH]$^+$

A solution of 6-methoxy-7-(2-(1,2,3-triazol-1-yl)ethoxy) quinazoline (920 mg, 3.2 mmol) in thionyl chloride (10 ml) containing DMF (0.9 ml) was heated at 80° C. for 1 hour. After evaporation of the volatiles, the residue was azeotroped with toluene. The residue was partitioned between ethyl acetate and water and the aqueous layer was adjusted to pH8 with solid sodium hydrogen carbonate. The organic layer was washed with water, brine, dried (MgSO$_4$), and the volatiles were removed by evaporation. The residue was purified by column chromatography eluting with methylene chloride/methanol (96/4) to give 4-chloro-6-methoxy-7-(2-(1,2,3-triazol-1-yl)ethoxy)quinazoline (693 mg, 71%).

$^1$H NMR Spectrum: (CDCl$_3$) 4.1(s, 3H); 4.55(t, 2H); 4.95(t, 2H); 7.3(s, 1H); 7.4(s, 1H); 7.75(s, 1H); 7.95(s, 1H); 8.85(s, 1H)

MS-EI: 305 [MH]$^+$

Elemental analysis: Found C, 51.0; H, 4.0; N, 22.6% C$_{13}$H$_{12}$N$_5$O$_2$Cl Requires C, 51.0; H, 3.9; N, 22.9%

EXAMPLE 11

Under nitrogen, 5,7-diaza-6-methyloxindole (105 mg, 0.70 mmol), (prepared as described for the starting material in Example 6), in DMSO (2 ml) was added dropwise to a suspension of sodium hydride (25 mg, 0.70 mmol ; prewashed with pentane). After stirring for 30 minutes at ambient temperature, 4-(2-methoxyethylsulphanyl)-7-(3-methylsulphonylpropoxy)quinazoline (100 mg, 0.28 mmol) was added. The mixture was heated at 100° C. for 2.5 hours. After cooling, the mixture was poured onto a saturated aqueous solution of ammonium chloride (15 ml). The precipitate was collected by filtration and purified by column chromatography eluting with methylene chloride/methanol (97/3 followed by 95/5 and 93/7) to give a solid. The solid was dissolved in methanol/methylene chloride (1/1) and 3.8M hydrogen chloride in ether (0.5 ml) was added. After removal of the volatiles, the residue was triturated with ether, collected by filtration, washed with ether and dried under vacuum to give 4-(5,7-diaza-6-methyloxindol-3-yl)-7-(3-methylsulphonylpropoxy)quinazoline hydrochloride (47 mg, 15%).

$^1$H NMR Spectrum: (DMSOd$_6$, CF$_3$COOD) 2.2–2.35(t, 2H); 2.75(s, 3H); 3.1(s, 3H); 3.35(t, 2H); 4.3(t, 2H); 7.05(s, 1H); 7.25(d, 1H); 8.75(s, 1H); 9.05(s, 1H); 9.6–9.7(br s, 1H)

MS-ESI: 414 [MH]$^+$

Elemental analysis: Found C, 46.3; H, 13.5; N, 4.8% C$_{19}$H$_{19}$N$_5$O$_4$S 2.5H$_2$O 1HCl Requires C, 46.1; H, 14.1; N, 5.1%

The starting material was prepared as follows:

2-Bromoethyl methyl ether (3.2 ml, 33 mmol) was added dropwise to a solution of 7-benzyloxy-3,4-dihydroquinazolin-4-thione (7.4 g, 28 mmol), (prepared as described for the starting material in Example 8), in DMF (275 ml) containing potassium carbonate (4.6 g, 33 mmol). After stirring for 4 hours, water was added and the precipitate was collected by filtration, washed with water, and dried under vacuum to give 7-benzyloxy4-(2-methoxyethylsulphanyl)quinazoline (8 g, 89%).

$^1$H NMR Spectrum: (DMSOd$_6$) 3.3(s, 3H); 3.56(t, 2H); 3.64(t, 2H); 5.32(s, 2H); 7.35–7.5(m, 5H); 7.52(d, 2H); 8.05(d, 1H); 8.9(s, 1H)

MS-ESI: 327 [MH]$^+$

A solution of 7-benzyloxy-4-(2-methoxyethylsulphanyl)quinazoline (8 g, 24.5 mmol) in TFA (80 ml) was refluxed for 5 hours. After cooling and removal of the volatiles by evaporation, the residue was triturated with water, collected by filtration, washed with water and then ethyl acetate. The residue was resuspended in methylene chloride, filtered, washed with petroleum ether and dried under vacuum to give 7-hydroxy-4-(2-methoxyethylsulphanyl)quinazoline (5.8 g, quant.).

$^1$H NMR Spectrum: (DMSOd$_6$, CF$_3$COOD) 3.35(s, 3H); 3.7(s, 4H); 7.24(s, 1H); 7.4(d, 1H); 8.25(d, 1H); 9.2(s, 1H)

MS-ESI: 237 [MH]$^+$

3-Chloroperoxybenzoic acid (25 g, 97.2 mmol) was added in portions to a solution of 3-(methylsulphanyl)-1-propanol (5 ml, 48.6 mmol) in methylene chloride (100 ml) while maintaining the reaction temperature at 25° C. After stirring for 1 hour at ambient temperature, the solid was removed by filtration and the filtrate was diluted with an aqueous solution of sodium sulphite (6.5 g, 51.6 mmol) in water (200 ml). The organic layer was separated and the volatiles were removed by evaporation. The white residue was triturated with acetone and the volatiles were again removed by evaporation. The solid was then dissolved in methylene chloride and aluminum oxide (90 Å mesh) was added. After standing for 15 minutes, the solid was removed by filtration and the volatiles were removed by evaporation to give 3-(methylsulphonyl)-1-propanol as a colourless oil (4.46 g, 66%).

$^1$H NMR Spectrum: (CDCl$_3$) 1.9–2.1(br s, 1H); 2.15(m, 2H); 2.95(s, 3H); 3.2(t, 2H); 3.85(t, 2H)

MS-EI: 139 [MH]+

A solution of 7-hydroxy-4-(2-methoxyethylsulphanyl)quinazoline (0.1 g, 3.8 mmol) in methylene chloride (20nil) containing triphenylphosphine (1.7 g, 6.36 mmol), 3-(methylsulphonyl)-1-propanol (0.85 g, 6 mmol) and diethyl azodicarboxylate (1.05 ml, 6.36 mmol) was stirred for 3 hours at ambient temperature. After partial evaporation of the methylene chloride, ethyl acetate was added. The precipitate was collected by filtration, washed with ether and dried under vacuum to give 4-(2-methoxyethylsulphanyl)-7-(3-methylsulphonylpropoxy)quinazoline (960 mg, 71%).

$^1$H NMR Spectrum: (DMSOd$_6$, CF$_3$COOD) 2.2–2.35(m, 2H); 3.05(s, 3H); 3.3(s, 3H); 3.35(t, 2H); 3.64(d, 2H); 3.67(d, 2H); 4.35(t, 2H); 7.35(d, 1H); 7.42(dd, 1H); 8.15(d, 1H); 9.1(s, 1H)

MS-ESI: 379 [MNa]$^+$

EXAMPLE 12

5,7-Diaza-6-methyloxindole (215 mg, 1.44 mmol), (prepared as described for the starting material in Example 6), in DMSO (2.5 ml) was added dropwise to a suspension of sodium hydride (58 mg, 1.44 mmol, prewashed with pentane) in DMSO (1 ml). After stirring for 30 minutes at ambient temperature, 7-(2-(2-methoxyethoxy)ethoxy)4-methylsulphanylquinazoline (140 mg, 0.578 mmol), (prepared as described for the starting material in Example 9), was added. After heating for 2 hours at 105° C., the mixture was poured onto methylene chloride/saturated aqueous ammonium chloride (40 ml/40 ml). The organic layer was separated and the aqueous layer was extracted with methylene chloride. The organic layer were combined, washed with brine, dried (MgSO$_4$), filtered and the volatiles were removed by evaporation. The residue was purified by column chromatography eluting with methylene chloride/methanol (95/5 followed by 94/6). After partial removal of the solvent, 3.8M hydrogen chloride in ether (1 ml) was added. After removal of the volatiles by evaporation, the solid was triturated with ether, collected by filtration, washed with ether and dried under vacuum to give 4-(5,7-diaza-6-methyloxindol-3-yl)-7-(2-(2-methoxyethoxy)ethoxy)quinazoline hydrochloride (72 mg, 28%).

$^1$H NMR Spectrum: (DMSOd$_6$, CF$_3$COOD) 2.7(s, 3H); 3.26(s, 3H); 3.45(t, 2H); 3.65(t, 2H); 3.85(t, 2H); 4.30(t, 2H); 7.1(d, 1H); 7.25(dd, 1H); 8.75(s, 1H); 9.05(s, 1H); 9.6–9.7(br s, 1H)

MS-ESI: 396 [MH]+

Elemental analysis: Found C, 53.7; H, 5.3; N, 15.8%
$C_{20}H_{21}N_5O_4$ 1H$_2$O 1HCl Requires C, $_{53.4}$; H, 5.4; N, 15.6%

EXAMPLE 13

Using a procedure similar to the one described for the synthesis of Example 12, 5,7-diaza-6-methyloxindole (167 mg, 1.1 mmol), (prepared as described for the starting material in Example 6), in DMF (4 ml) was added to sodium hydride (45 mg, 1.1 mmol) in DMF (1 ml) and the solution was reacted with 4-chloro-6-methoxy-7-(2-(2-methoxyethoxy)ethoxy)quinazoline (140 mg, 0.45 mmol) to give after work up, purification and hydrochloride salt formation 4-(5,7-diaza-6-methyloxindol-3-yl)-6-methoxy-7-(2-(2-methoxyethoxytethoxy)quinazoline hydrochloride (70 mg, 32%).

$^1$H NMR Spectrum: (DMSOd$_6$, CF$_3$COOD) 2.7(s, 3H); 3.26(s, 3H); 3.5(t, 2H); 3.65(t, 2H); 3.85(t, 2H); 3.95(s, 3H); 4.32(t, 2H); 7.2(s, 1H); 8.8(s, 1H); 9.05(s, 1H); 9.35–9.5(br s, 1H)

MS-ESI: 426 [MH]+

Elemental analysis: Found C, 51.2; H, 5.6; N, 14.4%
$C_{21}H_{23}N_5O_5$ 1.6H$_2$O 1.05HCl Requires C, 51.2; H, 5.6; N, 14.2%

The starting material was prepared as follows:

7-Hydroxy-6-methoxy-3-((pivaloyloxy)methyl-3,4-dihydroquinazolin-4-one (1.2 g, 3.9 mmol), (prepared as described for the starting material in Example 5), was suspended in methylene chloride (70 ml) cooled at 5° C. and 2-(2-methoxyethoxy)ethanol (653 μl, 5.5 mmol) was added followed by triphenylphosphine (1.44 g, 5.5 mmol) and diethyl azodicarboxylate (864 μl, 5.5 mmol) dropwise. After stirring for 1.5 hours at ambient temperature, the volatiles were removed under vacuum. The residue was purified by column chromatography eluting with ethyl acetate/methylene chloride (1/1 followed by 80/20) to give, after removal of the volatiles by evaporation, 6-methoxy-7-(2-(2-methoxyethoxy)-ethoxy)-3-((pivaloyloxy)methyl-3,4-dihydroquinazolin-4-one (1.6 g, 95%).

$^1$H NMR Spectrum: (DMSOd$_6$) 1.2(s, 9H); 3.26(s, 3H); 3.5(t, 2H); 3.6(t, 2H); 3.8(t, 2H); 3.9(s, 3H); 4.25(t, 2H); 5.95(s, 2H); 7.2(s, 1H); 7.5(s, 1H); 8.4(s, 1H)

A solution of saturated ammonia in methanol (20 ml) was added to a solution of 6-methoxy-7-(2-(2-methoxyethoxy)ethoxy)-3-((pivaloyloxy)methyl-3,4-dihydroquinazolin-4-one (2.26 g, 5.5 mmol) in a mixture of methylene chloride (15 ml) and ethanol (40 ml). After stirring for 24 hours at ambient temperature ammonia in methanol (20 ml) was added and stirring was continued for a further 24 hours. The volatiles were removed under vacuum and the residue was triturated with ether, collected by filtration, washed with ether and dried under vacuum to give 6-methoxy-7-(2-(2-methoxyethoxy)ethoxy)quinazolin-4-one (975 mg, 78%).

$^1$H NMR Spectrum: (DMSOd$_6$) 3.25(s, 3H); 3.45(t, 2H); 3.6(t, 2H); 3.8(t, 2H); 3.85(s, 3H); 4.25(t, 2H); 7.15(s, 1H); 7.45(s, 1H); 7.95(s, 1H)

MS-EI: 294 [M.]+

A solution of 6-methoxy-7-(2-(2-methoxyethoxy)ethoxy) quinazolin-4-one (930 mg, 3.2 mmol) in thionyl chloride (15 ml) containing DMF (150 μl) was heated at 60° C. for 1.5 hours. The volatiles were removed by evaporation. The residue was dissolved in methylene chloride, the solution was cooled to 5° C. and adjusted to pH8 by the addition of 5% aqueous sodium hydrogen carbonate solution. The organic layer was separated, washed with brine, dried (MgSO$_4$), filtered and the volatiles were removed under vacuum. The residue was purified by column chromatography eluting with ethyl acetate to give 4-chloro-6-methoxy-7-(2-(2-methoxyethoxy)ethoxy)quinazoline (863 mg, 87%).

$^1$H NMR Spectrum: (DMSOd$_6$) 3.25(s, 3H); 3.45(t, 2H); 3.65(t, 2H); 3.85(t, 2H); 4.0(s, 3H); 4.35(t, 2H); 7.4(s, 1H); 7.5(s, 1H); 8.9(s, 1H)

EXAMPLE 14

Using a procedure analogous to the one described for the synthesis of Example 10, 7-azaoxindole (147 mg, 1.1 mmol), (prepared as described for the starting material in Example 2), in DMF (2.5 ml) was added to sodium hydride (43.6 mg, 1.1 mmol) in DMF (1.5 ml) and the solution was reacted with 4-chloro-7-(3-morpholinopropoxy)quinazoline (134 mg, 0.43 mmol), (prepared as described for the starting material in Example 6), to give after work up, purification and hydrochloride salt formation, 4-(7-azaoxindol-3-yl)-7-(3-morpholinopropoxy)quinazoline hydrochloride (147 mg, 66%).

$^1$H NMR Spectrum: (DMSOd$_6$, CF$_3$COOD) 2.3(m, 2H); 3.15(t, 2H); 3.35(t, 2H); 3.55(d, 2H); 3.75(t, 2H); 4.05(d, 2H); 4.3(t, 2H); 7.15(s, 1H); 7.2–7.3(m, 2H); 7.95(d, 1H); 8.7(s, 1H); 8.6–8.8(br s, 1H); 9–9.1 (br s, 1H)

MS-ESI: 406 [MH]+

Elemental analysis: Found C, 51.8; H, 5.4; N, 13.7%
$C_{22}H_{23}N_5O_3$ 2H$_2$O 1.95HCl Requires C, 51.5; H, 5.7; N, 13.7%

EXAMPLE 15

Using a procedure analogous to the one described for the synthesis of Example 3, 7-azaoxindole (191 mg, 1.43 mmol), (prepared as described for the starting material in Example 2), in DMSO (2 ml) was added to sodium hydride (57 mg, 1.4 mmol) in DMSO (1 ml) and the solution was reacted with 7-(2-(2-methoxyethoxy)ethoxy)4-methylsulphanyl-quinazoline (140 mg, 0.47 mmol), (prepared as described for the starting material in Example 9), at 110° C. for 40 minutes to give after work-up, purification, and hydrochloride salt formation 4-(7-azaoxindol-3-yl)-7-(2-(2-methoxyethoxy)ethoxy) quinazoline hydrochloride (118 mg, 56%).

$^1$H NMR Spectrum: (DMSOd$_6$, CF$_3$COOD) 3.25(s, 3H); 3.5(t, 2H); 3.65(t, 2H); 3.85(t, 2H); 4.35(t, 2H); 7.15(s, 1H); 7.25–7.3(m, 2H); 7.95(d, 1H); 8.7(s, 1H); 8.65–8.8(br s, 1H); 8.95–9.1(br s, 1H)

MS-ESI: 381 [MH]+

Elemental analysis: Found C, 54.2; H, 5.3; N, 12.8%
$C_{20}H_{20}N_4O_4$ 1.15H$_2$O 1.22HCl Requires C, 53.9; H, 5.3; N, 12.5%

EXAMPLE 16

Using a procedure analogous to the one described for the synthesis of Example 3, 7-azaoxindole (171 mg, 1.27 mmol), (prepared as described for the starting material in Example 2), in DMSO (2 ml) was added to sodium hydride (51 mg, 1.3 mmol) in DMSO (1 ml) and the solution was reacted with 4-methylsulphanyl-7-(4-morpholinobut-2-yn-1-yloxy)quinazoline (140 mg, 0.425 mmol) to give after work up, purification and hydrochloride salt formation, 4-(7-azaoxindol-3-yl)-7-(4-morpholinobut-2-yn-1-yloxy) quinazoline hydrochloride (138 mg, 57%).

$^1$H NMR Spectrum: (DMSOd$_6$, CF$_3$COOD) 3.05–3.2(br s, 2H); 3.4–3.5(br s, 2H); 3.65–3.8(br t, 2H); 3.9–4.0(br s, 2H); 4.3(s, 2H); 5.2(s, 2H); 7.2–7.35(m, 3H); 7.95(d, 1H); 8.7(s, 1H); 8.7–8.8(br s, 1H); 9.0–9.1(br s, 1H)

MS-ESI: 416 [MH]$^+$

The starting material was prepared as follows:

Triphenylphosphine (4.09 g, 1.56 mmol) was added dropwise to a solution of 7-hydroxy-4-methylsulphanylquinazoline (1.2 g, 6.25 mmol), (prepared as described for the starting material in Example 8), in methylene chloride (30 ml), followed by 4-morpholinobut-2-yn-1-ol (1.26 g, 8.3 mmol), (J. Am. Chem. Soc. 1957, 79, 6184), in methylene chloride (5 ml) and diethyl azodicarboxylate (2.46 ml, 1.56 mmol) was added dropwise. After stirring for 3 hours at ambient temperature, the volatiles were removed under vacuum and the residue was purified by column chromatography eluting with methylene chloride/methanol (100/0 followed by 95/5). After removal of the solvent, the residue was triturated with ether, collected by filtration and dried under vacuum to give 4-methylsulphanyl-7-(4-morpholinobut-2-yn-1-yloxy) quinazoline (1.3 g, 63%).

$^1$H NMR Spectrum: (CDCl$_3$) 2.5(t, 4H); 2.7(s, 3H); 3.32(t, 2H); 3.7(t, 4H); 4.9(t, 2H); 7.2(d, 1H); 7.35(d, 1H); 8.0(d, 1H); 8.9(s, 1H)

MS-ESI: 330 [MH]$^+$

EXAMPLE 17

Using a procedure analogous to the one described for the synthesis of Example 3, 7-azaoxindole (146 mg, 1.09 mmol), (prepared as described for the starting material in Example 2), in DMSO (20 ml) was added to sodium hydride (43.5 mg, 1.09 mmol) in DMSO (0.5 ml) and the solution was reacted with 4-methylsulphanyl-7-(4-morpholinobut-2-en-1-yloxy)quinazoline (120 mg, 0.36 mmol) to give after work up, purification and hydrochloride salt formation, 4-(7-azaoxindol-3-yl)-7-(4-morpholinobut-2-en-1-yloxy) quinazoline hydrochloride (100 mg, 49%).

$^1$H NMR Spectrum: (DMSOd$_6$, CF$_3$COOD) 3.05(t, 2H); 3.35(d, 2H); 3.7(t, 2H); 3.85(d, 2H); 4.0(d, 2H); 4.9(d, 2H); 6.0(td, 1H); 6.25(td, 1H); 7.2(s, 1H); 7.25–7.35(m, 2H); 7.95(d, 1H); 8.7(s, 1H); 8.7–8.8(br s, 1H); 9.0–9.1 (br s, 1H)

MS-ESI: 418 [MH]$^+$

Elemental analysis: Found C, 49.0; H, 5.4; N, 12.4% C$_{23}$H$_{23}$N$_5$O$_3$ 2.5H$_2$O 2.8HCl Requires C, 48.9; H, 5.5; N, 12.4%

The starting material was prepared as follows:

Using a procedure analogous to the one described for the synthesis of the starting material in Example 16, 4-morpholinobut-2-en-1-ol (1.27 g, 8.13 mmol), (J. Med. Chem. 1972, 15, 110–112), was reacted with 7-hydroxy-4-methylsulphanylquinazoline (1.2 g, 6.25 mmol), (prepared as described for the starting material in Example 8), in methylene chloride (30 ml) in the presence of triphenylphosphine (4.09 g, 1.56 mmol) and diethyl azodicarboxylate (2.46 ml, 1.56 mmol) to give 4-methylsulphanyl-7-(4-morpholinobut-2-en-1-yloxy)quinazoline (1.15 g, 55%).

$^1$H NMR Spectrum: (CDCl$_3$) 2.45(br s, 4H); 2.7(s, 3H); 3.05(d, 2H); 3.7(t, 4H); 4.7(d, 2H); 5.9(m, 2H); 7.15–7.25 (m, 2H); 7.95(d, 1H); 8.9(d, 1H)

MS-ESI: 332 [MH]$^+$

EXAMPLE 18

A solution of 4-azaoxindole (268 mg, 2 mmol) in DMF (2.5 ml) was added to sodium hydride (80 mg, 2 mmol) in DMF (1.5 ml) and the solution was reacted with 4-chloro-7-(3-morpholinopropoxy)quinazoline (201 mg, 0.65 mmol), (prepared as described for the starting material in Example 6), in DMF (2 ml). After stirring for 45 minutes at 75° C., the solvent was removed by evaporation. The residue was purified by column chromatography eluting with methylene chloride/methanol (9317) to give, after evaporation of the solvent and hydrochloride salt formation (as described in Example 3), 4-(4-azaoxindol-3-yl)-7-(3-morpholinopropoxy)quinazoline hydrochloride (93 mg, 10%).

$^1$H NMR Spectrum: (DMSOd$_6$, CF$_3$COOD) 2.35(m, 2H); 3.15(m, 2H); 3.35(m, 2H); 3.52(d, 2H); 3.70(t, 2H); 4.0(d, 2H); 4.40(t, 2H); 7.20(m, 1H); 7.42(dd, 1H); 7.70(m, 2H); 7.8(t, 1H); 8.25(m, 1H); 9.40(s, 1H)

MS (ESI): 406 [MH]$^+$

Elemental analysis: Found C, 50.9; H, 5.6; N, 13.4% C$_{22}$H$_{23}$N$_5$O$_3$ 2.5H$_2$O 1.9HCl Requires C, 50.8; H, 5.8; N, 13.5%

The starting material was prepared as follows:

Sodium hydride (5.65 g, 130 mmol) was suspended in anhydrous DMF (100 ml) and diethyl malonate (19.15 ml, 130 mmol) was added dropwise over a 30 minute period. The reaction was stirred for 30 minutes after which 2-chloro-3-nitropyridine (9.9 g, 62.4 mmol) was added in one portion giving an instant red colour to the reaction mixture. After 3 hours at ambient temperature the DMF was evaporated off under vacuum and the residue purified by flash chromatography using increasingly polar solvent mixtures using first isohexane and ending with isohexane/ethyl acetate (3/2). Evaporation of the solvent gave 2-(3-nitro-2-pyridyl)diethyl malonate (11 g, 62%) as a yellow oil.

MS (ESI): [MH] 281

2-(3-Nitro-2-pyridyl)diethyl malonate (16 g, 57 mmol) was dissolved in DMSO (250 ml). Lithium chloride (4.8 g, 113 mmol) and water (1.02 g, 57 mmol) were added and the mixture was stirred at 120° C. for 5 hours. The reaction was allowed to cool to ambient temperature and diluted with ethyl acetate (500 ml). The organic phase was washed with brine (2×500 ml), dried (MgSO$_4$), filtered and evaporated. The resulting oil was purified by flash chromatography using isohexanes/ethyl acetate (1/1) as the eluent to give 2-(3-nitro-2-pyridyl)ethyl acetate (11.2 g, 94%) as a red oil.

A mixture of 2-(3-nitro-2-pyridyl)ethyl acetate (10.1, 48 mmol), tin(II)chloride dihydrate (54.3 g, 240 mmol) and ethyl acetate was stirred and heated at reflux for 5 hours. The reaction mixture was allowed to cool overnight, filtered through diatomaceous earth and the solvent was removed by evaporation. The resulting oil was purified by flash chromatography using increasingly polar solvent mixtures starting with methylene chloride and ending with methylene chloride/methanol (10/1). Removal of the solvent by evaporation gave 4-azaoxindole (2.1 g, 33%).

$^1$H NMR Spectrum: (DMSOd$_6$) 3.35(br s, 2H); 7.15(m, 2H); 8.05(d, 1H); 10.50(br s, 1H)

MS (ESI): [MH]$^+$ 133

EXAMPLE 19

Sodium hydride (53 mg, 1.3 mmol) was washed with pentane then suspended in anhydrous DMSO (0.5 ml). 5,7-Diaza-6-propyloxindole (234 mg, 1.3 mmol) in solution in DMSO (1.7 ml) was added and the mixture was stirred for 10 minutes under argon. 4-Methylsulphanyl-7-(2-(2-methoxyethoxy)ethoxy)quinazoline (130 mg, 0.44 mmol), (prepared as described for the starting material in Example 9), was then added and the reaction mixture was stirred at 100° C. for 4.5 hours. The solvent was then partially removed by rotary-evaporation and the residue was adsorbed onto silica and purified by flash chromatography using methylene chloride/methanol (95/5) as eluent. The product obtained was slightly impure and was further purified by flash chromatography using methylene chloride/acetonitrile/methanol (60/35/5) as eluent. The obtained solid was suspended in methylene chloride/methanol and treated with an ethereal solution of hydrogen chloride. The solvent was removed by evaporation to give 4-(5,7-diaza-6-propyloxindol-3-yl)-7-(2-(2-methoxyethoxy)ethoxy)quinazoline hydrochloride (125 mg, 59%).

$^1$H NMR Spectrum: (DMSOd$_6$, CF$_3$COOD) 0.95(t, 3H); 1.85(m, 2H); 2.95(t, 2H); 3.25(s, 3H); 3.50(m, 2H); 3.65(m, 2H); 3.85(m, 2H); 4.35(m, 2H); 7.1(d, 1H); 7.25(dd, 1H); 8.75(s, 1H); 9.05(s, 1H); 9.65(br s, 1H)

MS (ESI): 424 [MH]$^+$

Elemental analysis: Found C, 55.3; H, 6.0; N, 14.6% C$_{22}$H$_{25}$N$_5$O$_4$ 0.7H$_2$O 1.1HCl Requires C, 55.3; H, 5.8; N, 14.7%

The starting material was prepared as follows:

Hydrogen chloride gas (7.4 g, 200 mmol) was bubbled for 45 minutes through a mixture of butyronitrile (10 g, 145mnmol) and absolute ethanol (8.65 ml, 148 mmol) cooled to −5° C. The solution was kept at the same temperature for a further 2 hours then kept for 3 days in a cold room at 4° C. to produce a viscous oil. To the viscous oil a solution of ammonia in ethanol (8% w/w, 35 ml) was added. The reaction gave an exotherm and ammonium chloride precipitated out. The precipitate was removed by filtration and more ammonia in ethanol was added (100 ml). The colourless solution was stirred overnight at ambient temperature. The solution was concentrated by rotary evaporation then cooled in an ice bath to give butamidine hydrochloride which was collected by filtration and washed with ether (9.88 g, 55%, hygroscopic solid).

Sodium hydride (2.85 g, 71 mmnol) was washed with pentane then suspended in toluene (128 ml). Diethyl succinate (11.5 g, 66 mmol) was added (strong exotherm) followed 5 minutes later by ethyl formate (6.6 ml, 82 mmol). The reaction mixture was stirred for 45 minutes at ambient temperature. Isopropanol (70 ml) and butamidine hydrochloride (8.1 g, 66 mmol) were added and the mixture was heated at reflux for 3 hours. The solvent was removed by evaporation and the residue was dissolved in methylene chloride (150 ml) and methanol (600 ml). Silica was added and the solvent was removed by rotary evaporation. The powder obtained was placed on the top of a flash chromatography column and the product eluted using methylene chloride/methanol (95/5) to give ethyl (4-hydroxy-2-propylpyrimidin-5-yl) acetate (5.35 g, 36%) as a white solid.

Using a procedure analogous to the one described for the synthesis of the starting material in Example 6, ethyl (4-hydroxy-2-propylpyrimidin-5-yl) acetate (3 g, 13 mmol) was converted into ethyl (4-chloro-2-propylpyrimidin-5-yl) acetate (3.2 g, 99%).

Using a procedure analogous to the one described for the synthesis of the starting material in Example 6, ethyl (4-chloro-2-propylpyrinidin-5-yl) acetate (3.2 g, 13 mmol) was reacted with sodium azide to give, after purification by flash chromatography (petroleum ether/ether, 1/1), ethyl (4-azido-2-propylpyrimidin-5-yl) acetate (2.87 g, 88%).

Using a procedure analogous to the one described for the synthesis of the starting material in Example 6, ethyl (4-azido-2-propylpyrimnidin-5-yl) acetate (2.85 g, 11.4 mmol) was hydrogenated at 1.2 atmospheres at ambient temperature over 1.5 hours to give ethyl (4-amino-2-propylpyrinidin-5-yl) acetate (2.36 g, 93%).

MS (ESI): [MH]$^+$ 224

Ethyl (4-amino-2-propylpyrimidin-5-yl) acetate (1 g, 4.5 mmol) was dissolved in diphenyl ether (4 ml) and heated to 220–240° C. under argon for 3 hours. The partially-cooled solution (120° C.) was diluted with toluene (14 ml) then left to return to ambient temperature and petroleum ether (50 ml) was added. The formed precipitate was collected by filtration, washed with petroleum ether and redissolved in methylene chloride/methanol. To this solution, silica was added and the solvent was removed by rotary evaporation. The resulting powder was placed on the top of a silica column and the product was eluted off using methylene chloride/methanol (96/4) as the eluent. Removal of the solvent by evaporation gave 5,7-diaza-6-propyloxindole (307 mg, 38%) as a beige solid.

$^1$H NMR Spectrum: (DMSOd$_6$) 0.90(t, 3H); 1.75(q, 2H); 2.75(t, 2H); 3.55(s, 2H); 8.25(s, 1H); 11.3(br s, 1H)

EXAMPLE 20

Using a procedure analogous to the one described for the synthesis of Example 19, 4-aza-oxindole (153 mg, 1.14 mmol), (prepared as described for the starting material in Example 18), was added to sodium hydride (123 mg, 3 mmol) in DMSO (4 ml) and the solution was reacted with 4-methylsulphanyl-7-(2-(2-methoxyethoxy)ethoxy)quinazoline (223 mg, 0.76 mmol), (prepared as described for the starting material in Example 9), to give after work-up, purification and hydrochloride salt formation, 4-(4-azaoxindol-3-yl)-7-(2-(2-methoxyethoxy)ethoxy)quinazoline hydrochloride (57 mg, 16%).

$^1$H NMR Spectrum: (DMSOd$_6$, CF$_3$COOD) 3.25(s, 3H); 3.5(m, 2H); 3.65(m, 2H); 3.85(m, 2H); 4.35(m, 2H); 7.25(d, 1H); 7.3(m, 2H); 7.5(d, 1H); 8.0(d, 1H); 8.9(s, 1H); 10.1(d, 1H)

MS (ESI): 381 [MH]$^+$

Elemental analysis: Found C, 50.8; H, 5.5; N, 11.5% C$_{20}$H$_{20}$N$_4$O$_4$ 2.8H$_2$O 1.2HCl Requires C, 50.6; H, 5.7; N, 11.8%

EXAMPLE 21

Using a procedure analogous to the one described for the synthesis of Example 19, 5,7-diaza-6-propyloxindole (283 mg, 1.6 mmol), (prepared as described for the starting material in example 19), was reacted with 4-methylsulphanyl-7-(3-morpholinopropoxy)quinazoline (170 mg, 0.53 mmol), (prepared as described for the starting material in Example 8), to give 4-(5,7-diaza-6-propyloxindol-3-yl)-7-(3-morpholinopropoxy)quinazoline hydrochloride (135 mg, 47%).

$^1$H NMR Spectrum: (DMSOd$_6$, CF$_3$COOD) 0.95(t, 3H); 1.85(m, 2H); 2.45(m, 2H); 2.95(t, 2H); 3.15(m, 2H); 3.40(m, 2H); 3.55(m, 2H); 3.75(m, 2H);4.05(m, 2H); 4.30(m, 2H); 7.10(d, 1H); 7.25(dd, 1H); 8.75(s, 1H); 9.05(s, 1H); 9.65(br s, 1H)

MS (ESI): [MH]$^+$ 449

Elemental analysis: Found C, 53.1; H, 6.0; N, 15.3% C$_{24}$H$_{28}$N$_6$O$_3$ 0.8H$_2$O 2.2HCl Requires C, 53.1; H, 5.9; N, 15.5%

EXAMPLE 22

Sodium hydride (59 mg, 1.46 mmol, 60% in oil) was suspended in DMF (5 ml) and DMSO (1 ml). 5,7-Diaza-6- methyloxindole (218 mg, 1.46 mmol), (prepared as described for the starting material in Example 6), was added in one portion and the solution was carefully degassed using alternatively vacuum and argon and stirred for 20 minutes at ambient temperature under argon. 7-(3-(1,1-Dioxothiomorpholino)propoxy)-4-(2-methoxyethylsulphanyl)quinazoline (200 mg, 0.49 mmol) was then added in one portion and the reaction mixture was stirred at 70° C. for 5 hours. To complete the reaction the temperature was then raised to 100° C. for 12 hours. After cooling the DMF was removed by evaporation under vacuum and the residue was redissolved using methanol, dichloromethane and triethylamine. Silica was added and the solvent was removed by evaporation. The resulting powder was placed on the top of a flash chromatography column pre-equilibrated with dichloromethane/triethylamine (95/5). Elution was done using increasingly polar solvent mixture up to dichloromethane/methanol/triethylamine (85/10/5). Removal of the solvent by evaporation gave 4-(5,7-diaza-6-methyloxindol-3-yl)-7-(3-(1,1-dioxothiomorpholino)propoxy)quinazoline (126 mg, 56%). The hydrochloride salt was made by adding an ethereal solution of hydrogen chloride to the product in solution in dichloromethane/methanol followed by removal of the solvent by evaporation and trituration in ether.

$^1$H NMR Spectrum: (DMSOd$_6$, CF$_3$COOD) 2.30(m, 2H); 2.72(s, 3H); 3.50(m, 2H); 3.70(br s, 4H); 3.85(br s, 4H); 4.30(m, 2H); 7.12(d, 1H); 7.25(dd, 1H); 8.8(s, 1H); 9.05(s, 1H); 9.70(br s, 1H)

MS (ESI): 469 [MH]$^+$

Elemental analysis: Found C, 47.0; H, 5.3; N, 15.3% C$_{22}$H$_{24}$N$_6$O$_3$ 1.5H$_2$O 1.8HCl Et$_3$NHCl 0.25 Requires C, 47.4; H, 5.5; N, 14.7%

The starting material was prepared as follows:

A mixture of 3-amino-1-propanol (650 μl, 8.4 mmol) and vinyl sulphone (1 g, 8.4 mmol) was heated at 110° C. for 45 minutes. The mixture was allowed to cool and was purified by column chromatography eluting with methylene chloride/methanol (95/5) to give 3-(1,1-dioxothiomorpholino)-1-propanol (800 mg, 90%).

$^1$H NMR Spectrum: (CDCl$_3$) 1.7–1.8(m, 2H); 2.73(t, 2H); 3.06(br s, 8H); 3.25(s, 1H); 3.78(t, 2H)

MS-ESI: 194 [MH]$^+$

Diethyl azodicarboxylate (100 μl; 0.63 mmol) was added dropwise to a solution of 7-hydroxy-4-(2-methoxyethylsulphanyl)quinazoline (100 mg, 0.42 mmol), (prepared as described for the starting material in Example 11), 3-(1,1-dioxothiomorpholino)-1-propanol (99 mg, 0.51 mmol) and triphenylphosphine (167 mg, 0.63 mmol) in methylene chloride (6 ml). After stiring for 4 hours, triphenylphosphine (167 mg, 0.63 mmol) and diethyl azodicarboxylate (100 μl, 0.63 mmol) were added and stirring was continued for 1 hour. The volatiles were removed by evaporation and the residue was purified by column chromatography eluting with ethyl acetate/methanol (100/0 followed by 92/8). After removal of the solvent by evaporation, the residue was triturated with ether and the solid was collected by filtration and dried under vacuum to give 7-(3-(1,1-dioxothiomorpholino)propoxy)4-(2-methoxyethylsulphanyl)quinazoline (72 mg, 41%).

$^1$H NMR Spectrum: (CDCl$_3$) 2.05(m, 2H); 2.7(t, 2H); 3.0–3.1(m, 8H); 3.42(s, 3H); 3.6(t, 2H); 3.72(t, 2H); 4.2(t, 2H); 7.15(dd, 1H); 7.2(d, 1H); 8.0(d, 1H); 8.9(s, 1H)

MS-ESI: 434 [MNa]$^+$

EXAMPLE 23

5,7-Diaza-6-methyloxindole (440 mg, 3 mmol), (prepared as described for the starting material in Example 6), was dissolved in anhydrous DMF (15 ml), the solution was degassed and sodium hydride (120 mg, 3 mmol) was added in one portion. The reaction mixture was degassed again and gave a green solution after 5 minutes at ambient temperature. Crude 4-chloro-6-methoxy-7-(2-(4-pyridyloxy)ethoxy)quinazoline was dissolved in DMF (10 ml) and the solution was degassed prior to its addition to the oxindole anion solution. The reaction mixture was stirred at 95° C. for 90 minutes, cooled to ambient temperature and the solvent was removed by evaporation. The residue was redissolved in a mixture of methylene chloride/methanol/ammonia (100/10/1) and 2 g of silica were added. The solvent was removed by evaporation again, the free flowing powder was placed on the top of a silica column and the product was eluted off using the above solvent system. Evaporation of the solvent gave 210 mg of the free base which was converted to the hydrochloride salt using an ethereal solution of hydrogen chloride to give 4-(5,7-diaza-6-methyloxindol-3-yl)-6-methoxy-7-(2-(4-pyridyloxy)ethoxy)quinazoline hydrochloride (145 mg, 26%).

$^1$H NMR Spectrum: (DMSOd$_6$, CF$_3$COOD) 2.7(s, 3H); 3.9(s, 3H); 4.6(m, 2H); 4.8(m, 2H); 7.2(s, 1H); 7.65(d, 2H); 8.7(s, 1H); 8.8(d, 2H); 8.9(s, 1H); 9.4(br s, 1H); 12.2(s, 1H)

MS (ESI): 445 [MH]$^+$

Elemental analysis: Found C, 48.5; H, 4.5; N, 14.9% C$_{23}$H$_{20}$N$_6$O$_4$ 2.7H$_2$O 2HCl Requires C, 48.8; H, 4.9; N, 14.9%

The starting material was prepared as follows:

4-Pyridyloxyethanol (3.5 g, 25.2 mmol), (J. Chem. Soc. Perk Trans 2, 1987, 1867), was suspended in methylene chloride (75 ml) and triethylarnine (2.6 g, 26 mmol) and tosyl chloride (4.7 g, 0.25 mmol) was added. The reaction mixture was stirred at ambient temperature for 10 minutes then washed with water and the organic phase was passed through a Bond Elute (Trade mark of Varian Associates Corp.) column to remove any residual salts. The solvent was removed by evaporation and the residue was triturated with ether to give 2-(4-pyridyloxy)ethyl paratoluene sulphonate (3.94 g, 53% yield).

4-Benzyloxy-5-methoxy-2-nitrobenzamide (26 g, 91 mmol), (J. Med. Chem. 1977, vol 20, 146–149), was dissolved in TFA and heated at reflux for 2 hours. After cooling the TFA was removed by evaporation and the residue was stirred with 2M sodium hydroxide and insoluble material was removed by filtration. The red aqueous solution was acified to pH1 with concentrated hydrochloric acid and allowed to cool back to ambient temperature before collecting the product by filtration. The obtained solid was washed with water and ether and dried in a vacuum oven at 60° C. to give 4-hydroxy-5-methoxy-2-nitrobenzamide (11.04 g, 62%).

4-Hydroxy-5-methoxy-2-nitrobenzamide (1.86 g, 9.5 mmol) and 2-(4-pyridyloxy)ethyl paratoluene sulphonate (3.3 g, 11.2 mmol) were mixed in the presence of potassium carbonate (1.7 g, 12.3 mmol) and anhydrous DMF (25 ml) and heated at 80° C. for 2 hours. The reaction mixture was allowed to cool overnight, the DMF was removed by evaporation and the residue was quenched into water (250 ml). The solid was collected by filtration and washed with a mixture of acetone/ether (1/1) to give 5-methoxy-2-nitro-4-(2-(4-pyridyloxy)ethoxy)benzamide as a cream solid (2.16 g, 68%).

5-Methoxy-2-nitro-4-(2-(4-pyridyloxy)ethoxy) benzamide (2.15 g, 6.4 mmol) and 10% palladium-on-charcoal catalyst (100 mg) were suspended in methanol (400 ml) and placed under hydrogen at atmospheric pressure. The reaction mixture was heated at 40° C. for 1 hour, cooled to ambient temperature, filtered through diatomaceous earth and the solvent was removed by evaporation. The precipitate was slurried with ether and collected by filtration to give 2-amino-5-methoxy-4-(2-(4-pyridyloxy)ethoxy)benzamide as a cream solid (1.95 g, 99%). 2-Amino-5-methoxy-4-(2-(4-pyridyloxy)ethoxy)benzamide (1.95 g, 6.4 mmol) and formamide (10 ml) were heated at 190–200° C. for 1 hour. The reaction mixture was allowed to cool to 50° C. as the product precipitated out. Water (50 ml) was added and the solid was collected by filtration, washed with more water and ether and dried under vacuum to give 6-methoxy-7-(2-(4-pyridyloxy)ethoxy)-3,4-dihydroquinazolin-4-one (0.99 g, 49%) as a cream solid. The 6-methoxy-7-(2-(4-pyridyioxy)ethoxy)-3,4-dihydroquinazolin-4-one (312 mg, 1 mmol) was heated at reflux in thionyl chloride (10 ml) and DMF (5 drops) for 1 hour, then evaporated to dryness and partitioned between a saturated solution of sodium hydrogen carbonate and methylene chloride. The methylene chloride phase was dried by filtration through a phase separator paper and the solvent was removed by evaporation to give crude 4-chloro-6-methoxy-7-(2-(4-pyridyloxy)ethoxy)quinazoline which was used without further purification.

EXAMPLE 24

Using a procedure analogous to the one described for the synthesis of Example 23, 7-(2-(imidazol-1-yl)ethoxy)-6-methoxy-3,4-dihydroquinazoline-4-one (286 mg, 1 mmol) was reacted with thionyl chloride (50 ml) to give 4-chloro-7-(2-(imidazol-1-yl)ethoxy)-6-methoxyquinazoline which was then reacted with 5,7-diaza-6-methyloxindole (440 mg, 3 mmol) and sodium hydride (120 mg, 3 mmol) to give 4-(5,7-diaza-6-methyloxindol-3-yl)-7-(2-(imidazol-1-yl)ethoxy)-6-methoxyquinazoline hydrochloride (80 mg, 15%).

$^1$H NMR Spectrum: (DMSOd$_6$, CF$_3$COOD) 2.7(s, 3H); 3.9(s, 3H); 4.2(m, 2H); 4.7(m, 2H); 7.2(s, 1H); 7.7(s, 1H); 7.8(s, 1H); 8.7(s, 1H); 9.0(s, 1H); 9.2(s, 1H); 9.4(br s, 1H); 12.2(s, 1H)

MS (ESI): 418 [MH]$^+$

Elemental analysis: Found C, 48.8; H, 4.4; N, 18.8% C$_{21}$H$_{19}$N$_7$O$_3$ 1.5H$_2$O 2HCl Requires C, 48.8; H, 4.7; N, 19.0%

The starting material was prepared as follows:

Imidazole (20.4 g, 300 mmol) and ethylene carbonate (28.6 g, 325 mmol) were heated at 125° C. for 1 hour. Once the CO$_2$ evolution had ceased the reaction mixture was allowed to cool to ambient temperature, was suspended in methylene chloride/methanol (10/1, 50 ml) and was placed on the top of a short plug of silica. Elution was done using an increasingly polar solvent mixture of methylene chloride/methanol (100/10 up to 100/15). Removal of the solvent by evaporation gave crude 2-(imidazol-1-yl)ethanol (20.1 g, 60%).

A portion of the crude 2-(imidazol-1-yl)ethanol (10 g, 89 mmol) and triethylamine (10.1 g, 100 mmol) were dissolved in methylene chloride (250 ml), tosyl chloride (17.5 g, 92 mmol) was added over 5 minutes as a solid, giving an exotherm to reflux. The reaction was stirred for 30 minutes at ambient temperature then quenched into 250 ml of 1M hydrogen chloride and 250 ml of methylene chloride. The organic phase was washed with brine and dried by passing it through a phase separator paper. Removal of the solvent by evaporation and purification by flash chromatography using methylene chloride/methanol/ammonia (100/10/1) gave 2-(imidazo]-1-yl)ethyl paratoluene sulphonate (10.95 g, 46%, impure). 4-Hydroxy-5-methoxy-2-nitrobenzamide (3 g, 15.3 mmol), (prepared as described for the starting material in Example 23), and 2-(imidazol-1-yl)ethyl para-toluene sulphonate (7 g, impure) were mixed in the presence of potassium carbonate (5 g, 72 mmol) and anhydrous DMF (20 ml) and heated at 100° C. for 3 hours. The reaction mixture was allowed to cool to ambient temperature and the DMF was removed by evaporation. The residue was resuspended in methylene chloride/methanol/ammnonia (100/10/1) and silica (15 g) was added. The solvent was removed by evaporation and the resulting powder was placed on the top of a silica gel column and eluted using first methylene chloride and slowly increasing the solvent polarity up to methylene chloride/methanol/ammnonia (100/10/1). Removal of the solvent by evaporation gave 4-(2-(imidazol-1-yl)ethoxy)-5-methoxy-2-nitrobenzaride as a cream solid (2.53 g, 55%).

Using a procedure analogous to the one described for the starting material in Example 23, reduction of the nitro group of 4-(2-(imidazol-1-yl)ethoxy)-5-methoxy-2-nitrobenzamide (2.4 g, 7.8 mmol) gave 2-amino-4-(2-(imidazol-1-yl)ethoxy)-5-methoxybenzamide (2.12 g, 98%).

2-Amino-4-(2-(imidazol-1-yl)ethoxy)-5-methoxybenzamide (2.10 g, 7.6 mmol) and formamide (10 ml) were heated at 190–200° C. for 3 hours. The reaction mixture was allowed to cool to ambient temperature and quenched into water (20 ml). The precipitate was collected by filtration and washed with water and ether and dried under vacuum to give 7-(2-(imidazol-1-yl))-6-methoxy-3,4-dihydroquinazolin-4-one (1.42 g, 65%).

EXAMPLE 25

Using a procedure analogous to the one described for the synthesis of Example 18, 5-azaoxindole (130 mg, 0.97 mmol), (Tet. 1993, 49, 2885), was reacted with 4-chloro-7-(3-morpholinopropoxy)quinazoline (234 mg, 0.76 mmol), (prepared as described for the starting material in Example 6), to give after work-up, purification and hydrochloride salt formation, 4-(5-azaoxindol-3-yl)-7-(3-morpholinopropoxy) quinazoline hydrochloride (112 mg, 27%).

$^1$H NMR Spectrum: (DMSOd$_6$, CF$_3$COOD) 2.25(m, 2H); 3.15(m, 2H); 3.35(m, 2H); 3.50(d, 2H); 3.75(t, 2H); 4.0(d, 2H); 4.30(t, 2H); 7.15(s, 1H); 7.25(dd, 1H); 7.30(d, 1H); 8.35(d, 1H); 8.75(s, 1H); 9.30(s, 1H); 9.55(d, 1H)

MS (ESI): 391 [MH]$^+$

Elemental analysis: Found C, 47.5; H, 5.4; N, 12.5% C$_{22}$H$_{23}$N$_5$O$_3$ 3H$_2$O 2.6HCl Requires C, 47.7; H, 5.8; N, 12.6%

EXAMPLE 26

The following illustrate representative pharmaceutical dosage forms containing the compound of formula 1, or a pharmaceutically acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

-continued

| (b) Tablet II | mg/tablet |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
| --- | --- |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
| --- | --- |
| Compound X | 10 |
| Lactose Ph.Eur | 488.5 |
| Magnesium stearate | 1.5 |

| (e) Injection I | (50 mg/ml) |
| --- | --- |
| Compound X | 5.0% w/v |
| 1N Sodium hydroxide solution | 15.0% v/v |
| 0.1N Hydrochloric acid | 4.5% w/v |
| (to adjust pH to 7.6) | |
| Polyethylene glycol 400 | |
| Water for injection to 100% | |

| (f) Injection II | 10 mg/ml) |
| --- | --- |
| Compound X | 1.0% w/v |
| Sodium phosphate BP | 3.6% w/v |
| 0.1N Sodium hydroxide solution | 15.0% v/v |
| Water for injection to 100% | |

| (g) Injection III | (1 mg/ml, buffered to pH6) |
| --- | --- |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

What is claimed is:
1. A compound of the formula I:

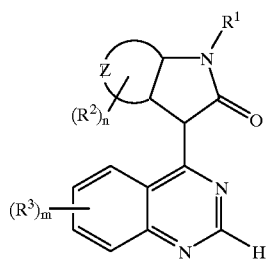

(I)

wherein:
  ring Z is a 6-membered heterocyclic ring containing 1 to 3 nitrogen atoms with the proviso that the group at the 4-position of the quinazoline ring is not a substituted or unsubstituted group selected from 4,5,7-triazaoxindol-3-yl and 4,6,7-triazaoxindol-3-yl;

$R^1$ represents hydrogen, $C_{1-4}$alkyl, $C_{1-4}$alkoxymethyl, di($C_{1-4}$alkoxy)methyl or $C_{1-4}$alkanoyl;

$R^2$ represents hydroxy, halogeno, $C_{1-3}$alkyl, $C_{1-3}$alkoxy, $C_{1-3}$alkanoyloxy, trifluoromethyl, 2,2,2-trifluoroethyl, cyano, amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkyl-aminosulphonyl, N,N-di($C_{1-4}$alkyl) aminosulphonyl or $C_{1-4}$alkylsulphonylamino or $R^2$ is selected from one of the following four groups:
  1) $R^4X^1$ wherein $X^1$ represents a direct bond, —O—, —$NR^5$—, $C_{1-3}$alkyl, $C_{2-4}$alkanoyl, —$CONR^6R^7$—, —$SO_2NR^8R^9$— or —$SO_2R^{10}$— (wherein $R^5$, $R^6$ and $R^8$, each independently represents hydrogen or $C_{1-2}$alkyl and $R^7$, $R^9$ and $R^{10}$ each independently represents $C_{1-4}$alkyl and wherein $R^4$ is linked to $R^7$, $R^9$ or $R^{10}$) and $R^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;
  2) $X^2C_{2-4}$alkyl$X^3C_{1-3}$alkyl (wherein $X^2$ is —O— or —$NR^{11}$— (wherein $R^{11}$ is hydrogen, $C_{1-3}$alkyl or $C_{1-3}$alkoxy$C_{2-3}$alkyl) and $X^3$ is —O—, —$NR^{12}$—, —S—, —SO— or —$SO_2$— (wherein $R^{12}$ is hydrogen, $C_{1-3}$alkyl or $C_{1-3}$alkoxy$C_{2-3}$alkyl);
  3) $C_{1-2}$alkyl$X^4C_{2-3}$alkyl$X^5C_{1-3}$alkyl (wherein $X^4$ and $X^5$ which may be the same or different are each —O—, —S—, —SO—, —$SO_2$— or —$NR^{13}$— (wherein $R^{13}$ is hydrogen, $C_{1-3}$alkyl or $C_{1-3}$alkoxy$C_{2-3}$alkyl); and
  4) $C_{1-3}$alkyl$X^6C_{1-3}$alkyl (wherein $X^6$ is —O—, —S—, —SO—, —$SO_2$— or —$NR^{14}$— (wherein $R^{14}$ is hydrogen, $C_{1-3}$alkyl or $C_{1-3}$alkoxy$C_{2-3}$alkyl);

n is an integer from 0 to 3;
m is an integer from 0 to 4; and
$R^3$ represents hydroxy, halogeno, nitro, trifluoromethyl, $C_{1-3}$alkyl, cyano, amino or $R^{15}X^7$, wherein $X^7$ represents a direct bond, —O—, —$CH_2$—, —S—, —SO—, —$SO_2$—, —$NR^{16}CO$—, —$CONR^{17}$—, —$SO_2NR^{18}$—, —$NR^{19}SO_2$— or —$NR^{20}$— (wherein $R^{16}$, $R^{17}$, $R^{18}$, $R^{19}$ and $R^{20}$ each independently represents hydrogen, $C_{1-3}$alkyl or $C_{1-3}$alkoxy$C_{2-3}$alkyl), and $R^{15}$ is selected from one of the following seventeen groups:
  1) hydrogen or $C_{1-5}$alkyl which may be unsubstituted or which may be substituted with one or more groups selected from hydroxy, fluoro and amino;
  2) $C_{1-5}$alkyl$X^8COR^{21}$, wherein $X^8$ represents —O— or —$NR^{22}$— (in which $R^{22}$ represents hydrogen, $C_{1-3}$alkyl or $C_{1-3}$alkoxy$C_{2-3}$alkyl) and $R^{22}$ represents $C_{1-3}$alkyl, —$NR^{23}R^{24}$— or —$OR^{25}$— (wherein $R^{23}$, $R^{24}$ and $R^{25}$ which may be the same or different each represents hydrogen, $C_{1-3}$alkyl or $C_{1-3}$alkoxy$C_{2-3}$alkyl);
  3) $C_{1-5}$alkyl$X^9R^{26}$, wherein $X^9$ represents —O—, —S—, —SO—, —$SO_2$—, —OCO—, —$NR^{27}CO$—, —$CONR^{28}$—, —$SO_2NR^{29}$—, —$NR^{30}SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen, $C_{1-3}$alkyl, cyclopentyl, cyclohexyl or a 5 or 6-membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy;

4) $C_{1-5}$alkyl$X^{10}C_{1-5}$alkyl$X^{11}R^{32}$, wherein $X^{10}$ and $X^{11}$ which may be the same or different are each —O—, —S—, —SO—, —SO$_2$—, —NR$^{33}$CO—, —CONR$^{34}$—, —SO$_2$NR$^{35}$—, —NR$^{36}$SO$_2$— or —NR$^{37}$— (wherein $R^{33}$, $R^{34}$, $R^{35}$, $R^{36}$ and $R^{37}$ each independently represents hydrogen, $C_{1-3}$alkyl or $C_{1-3}$alkoxy$C_{2-3}$alkyl) and $R^{32}$ represents hydrogen or $C_{1-3}$alkyl;

5) $R^{38}$, wherein $R^{38}$ is a 5 or 6-membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy;

6) $C_{1-5}$alkyl$R^{38}$, wherein $R^{38}$ is as defined herein;
7) $C_{2-5}$alkenyl$R^{38}$, wherein $R^{38}$ is as defined herein;
8) $C_{2-5}$alkynyl$R^{38}$, wherein $R^{38}$ is as defined herein;
9) $R^{39}$, wherein $R^{39}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from hydroxy halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{40}$R$^{41}$ and —NR$^{42}$COR$^{43}$— (wherein $R^{40}$, $R^{41}$, $R^{42}$ and $R^{43}$, which may be the same or different, each represents hydrogen, $C_{1-4}$alkyl or $C_{1-3}$alkoxy$C_{2-3}$alkyl);

10) $C_{1-5}$alkyl$R^{39}$, wherein $R^{39}$ is as defined herein;
11) $C_{2-5}$alkenyl$R^{39}$, wherein $R^{39}$ is as defined herein;
12) $C_{2-5}$alkynyl$R^{39}$, wherein $R^{39}$ is as defined herein;
13) $C_{1-5}$alkyl$X^{12}R^{39}$, wherein $X^{12}$ represents —O—, —S—, —SO—, —SO$_2$—, —NR$^{44}$CO—, —CONR$^{45}$—, —SO$_2$NR$^{46}$—, —NR$^{47}$SO$_2$— or —NR$^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{39}$ is as defined herein;

14) $C_{2-5}$alkenyl$X^{13}R^{39}$, wherein $X^{13}$ represents —O—, —S—, —SO—, —SO$_2$—, —NR$^{49}$CO—, —CONR$^{50}$—, —SO$_2$NR$^{51}$—, —NR$^{52}$SO$_2$— or —NR$^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{39}$ is as defined herein;

15) $C_{2-5}$alkynyl$X^{14}R^{39}$, wherein $X^{14}$ represents —O—, —S—, —SO—, —SO$_2$—, —NR$^{54}$CO—, —CONR$^{55}$—, —SO$_2$NR$^{56}$—, —NR$^{57}$SO$_2$— or —NR$^{58}$— (wherein $R^{54}$, $R^{55}$, $R^{56}$, $R^{57}$ and $R^{58}$ each independently represents hydrogen, $C_{1-3}$alkyl or $C_{1-3}$alkoxy$C_{2-3}$alkyl) and $R^{39}$ is as defined herein;

16) $C_{1-3}$alkyl$X^{15}C_{1-3}$alkyl$R^{39}$, wherein $X^{15}$ represents —O—, —S—, —SO—, —SO$_2$—, —NR$^{59}$CO—, —CONR$^{60}$—, —SO$_2$NR$^{61}$—, —NR$^{62}$SO$_2$— or —NR$^{63}$— (wherein $R^{59}$, $R^{60}$, $R^{61}$, $R^{62}$ and $R^{63}$ each independently represents hydrogen, $C_{1-3}$alkyl or $C_{1-3}$alkoxy$C_{2-3}$alkyl) and $R^{39}$ is as defined herein); and 17) $C_{1-3}$alkyl$X^{15}C_{1-3}$alkyl$R^{38}$, wherein $X^{15}$ and $R^{38}$ are as defined herein;

and salts thereof.

2. A compound as claimed in claim 1 wherein ring Z is a 6-membered heterocyclic ring containing 1 or 2 nitrogen atoms with the proviso that where $R^2$ is a group $R^4X^1$, $X^1$ is not $C_{2-4}$alkanoyl or —SO$_2$R$^{10}$— and $R^4$ is not optionally substituted phenyl or an optionally substituted 5 or 6-membered unsaturated heterocyclic ring.

3. A compound as claimed in claim 1 or 2 wherein $R^1$ is hydrogen.

4. A compound as claimed in claim 1 or 2 wherein $R^2$ is halogeno, $C_{1-2}$alkyl, $C_{1-2}$alkoxy, trifluoromethyl, 2,2,2-trifluoroethyl, cyano, nitro, $C_{1-3}$alkanoylamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl or $C_{1-3}$alkylsulphonylamino or R is selected from one of the following four groups:

1) $R^4X^1$ wherein $X^1$ represents —O—, —NR$^5$—, $C_{1-3}$alkyl, —CONR$^6$R$^7$— or —SO$_2$NR$^8$R$^9$— (wherein $R^5$, $R^6$, and $R^8$, each independently represents hydrogen or $C_{1-2}$alkyl and $R^7$ and R9 each independently represents $C_{1-3}$alkyl and wherein $R^4$ is linked to $R^7$ or $R^9$) and $R^4$ represents a 5 or 6-membered saturated heterocyclic group with one or two heteroatoms, selected independently from O, S and N, which heterocyclic group may bear two oxo substituents on a ring sulphur heteroatom;

2) $X^2C_{2-3}$alkyl$X^3$methyl, wherein $X^2$ is —O— or —NR$^{11}$— (wherein $R^{11}$ is hydrogen or $C_{1-2}$alkyl) and $X^3$ is —O—, —NR$^{12}$— or —SO$_2$— (wherein $R^{12}$ is hydrogen or $C_{1-2}$alkyl);

3) $C_{1-2}$alkyl$X^4C_{2-3}$alkyl$X^5$methyl, wherein $X^4$ and $X^5$ which may be the same or different are each —NR$^{13}$— or —SO$_2$— (wherein $R^{13}$ is hydrogen or $C_{1-2}$alkyl); and 4) $C_{1-2}$alkyl$X^6C_{1-2}$alkyl, wherein $X^6$ is —O—, —NR$^{14}$— or —SO$_2$— (wherein $R^{14}$ is hydrogen or $C_{1-2}$alkyl).

5. A compound as claimed in claim 1 or 2 wherein $R^3$ is hydroxy, halogeno, nitro, trifluoromethyl, $C_{1-3}$alkyl, cyano, amino or $R^{15}X^7$ wherein $X^7$ is as defined in claim 1 and $R^{15}$ is selected from one of the following fifteen groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl; 1

3) $C_{2-3}$alkyl$X^9R^{26}$, wherein $X^9$ is as defined in claim 1 and $R^{26}$ is a group selected from $C_{1-2}$alkyl, cyclopentyl, cyclohexyl, pyrrolidinyl and piperidinyl which group is linked to $X^9$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy;

4) $C_{2-3}$alkyl$X^{10}C_{2-3}$alkyl$X^{11}R^{32}$, wherein $X^{10}$ and $X^{11}$ arc as defined in claim 1 and $R^{32}$ represents hydrogen or $C_{1-2}$alkyl;

5) $R^{38}$, wherein $R^{38}$ is as defined in claim 1;
6) $C_{1-2}$alkyl$R^{67}$ (wherein $R^{67}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$akyl$R^{68}$ (wherein $R^{68}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);
7) $R^{39}$, wherein $R^{39}$ is as defied in claim 1;
8) $C_4$alkyl$R^{39}$, wherein $R^{39}$ is as defined in claim 1;
9) 1-$R^{39}$but-2-en-4-yl, wherein $R^{39}$ is as defined in claim 1;
10) 1-$R^{39}$but-2-yn-4-yl, wherein $R^{39}$ is as defined in claim 1;
11) $C_{2-4}$alkyl$X^{12}R^{39}$, wherein $X^{12}$ and $R^{39}$ are as defined in claim 1;
12) 1-$(R^{39}X^{13})$but-2-en-4-yl, wherein $X^{13}$ and $R^{39}$ are as defined in claim 1;
13) 1-$(R^{39}X^{14})$but-2-yn-4-yl, wherein $X^{14}$ and $R^{39}$ are as defined in claim 1;
14) ethyl$X^{15}$methyl$R^{39}$, wherein $X^{15}$ and $R^{39}$ are as defined in claim 1; and
15) ethyl$X^{15}$methyl$R^{38}$, wherein $X^{15}$ and $R^{38}$ are as defined in claim 1.

6. A compound of the formula Ia:

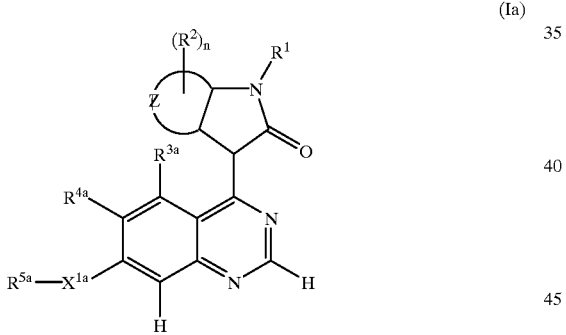

(Ia)

wherein:
ring Z is a 5 or 6-membered heterocyclic ring containing 1 to 3 nitrogen atoms with the proviso that the group at the 4-position of the quinazoline ring is not a substituted or unsubstituted group selected from 4,5,7-triazaoxindol-3-yl and 4,6,7-triazaoxindol-3-yl;

$R^1$ represents hydrogen, $C_{1-4}$alkyl, $C_{1-4}$alkoxymethyl, di($C_{1-4}$alkoxy)methyl or $C_{1-4}$alkanoyl;

$R^2$ represents hydroxy, halogeno, $C_{1-3}$alkyl, $C_{1-3}$alkoxy, $C_{1-3}$alkanoyloxy, trifluoromethyl, 2,2,2-trifluoroethyl, cyano, amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkyl-aminosulphonyl, N,N-di($C_{1-4}$alkyl) aminosulphonyl or $C_{1-4}$alkylsulphonylamino or $R^2$ is selected from one of the following four groups:
1) $R^4X^1$ wherein $X^1$ represents a direct bond, —O—, —$NR^5$—, $C_{1-3}$alkyl, $C_{2-4}$alkanoyl, —$CONR^6R^7$—, —$SO_2NR^8R^9$— or —$SO_2R^{10}$— (wherein $R^5$, $R^6$ and $R^8$, each independently represents hydrogen or $C_{1-2}$alkyl and $R^7$, $R^9$ and $R^{10}$ each independently represents $C_{1-4}$alkyl and wherein $R^4$ is linked to $R^7$, $R^9$ or $R^{10}$) and $R^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;
2) $X^2C_{2-4}$alkyl$X^3C_{1-3}$alkyl (wherein $X^2$ is —O— or —$NR^{11}$— (wherein $R^{11}$ is hydrogen, $C_{1-3}$alkyl or $C_{1-3}$alkoxy$C_{2-3}$alkyl) and $X^3$ is —O—, —$NR^{12}$—, —S—, —SO— or —$SO_2$— (wherein $R^{12}$ is hydrogen, $C_{1-3}$alkyl or $C_{1-3}$alkoxy$C_{2-3}$alkyl);
3) $C_{1-2}$alkyl$X^4C_{2-3}$alkyl$X^5C_{1-3}$alkyl (wherein $X^4$ and $X^5$ which may be the same or different are each —O—, —S—, —SO—, —$SO_2$— or —$NR^{13}$— (wherein $R^{13}$ is hydrogen, $C_{1-3}$alkyl or $C_{1-3}$alkoxy$C_{2-3}$alkyl); and
4) $C_{1-3}$alkyl$X^6C_{1-3}$alkyl (wherein $X^6$ is —O—, —S—, —SO—, —$SO_2$— or —$NR^{14}$— (wherein $R^{14}$ is hydrogen, $C_{1-3}$alkyl or $C_{1-3}$alkoxy$C_{2-3}$alkyl);
is an integer from 0 to 3;

$R^{3a}$ represents hydrogen, hydroxy, methoxy, amino, nitro or halogeno;

$R^{4a}$ represents hydrogen, hydroxy, halogeno, cyano, nitro, trifluoromethyl, $C_{1-3}$alkyl, $C_{1-3}$alkoxy, $C_{1-3}$alkylthio, —$NR^{6a}R^{7a}$— (wherein $R^{6a}$ and $R^{7a}$, which may be the same or different, each represents hydrogen or $C_{1-3}$alkyl), or a group $R^8a(CH_2)_{ta}X^{2a}$ (wherein $R^{8a}$ is a 5 or 6-membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, ta is an integer from 0 to 4 and $X^{2a}$ represents a direct bond, —O—, —$CH_2$—, —S—, —$SO_2$—, —$SO_2$—, —$NR^{9a}CO$—, —$CONR^{10a}$—, —$SO_2NR^{11a}$—, —$NR^{12a}SO_2$— or —$NR^{13a}$— (wherein $R^{9a}$, $R^{10a}$, $R^{11a}$, $R^{12a}$ and $R^{13a}$ each independently represents hydrogen, $C_{1-3}$alkyl or $C_{1-3}$alkoxy$C_{2-3}$alkyl));

$X^{1a}$ represents a direct bond, —O—, —$CH_2$—, —S—, —SO—, —$SO_2$—, —$NR^{14a}CO$—, —$CONR^{15a}$—, —$SO_2NR^{16a}$—, —$NR^{17a}SO_2$— or —$NR^{18a}$— (wherein $R^{14a}$, $R^{15a}$, $R^{16a}$, $R^{17a}$ and $R^{18a}$ each independently represents hydrogen, $C_{1-3}$alkyl or $C_{1-3}$alkoxy$C_{2-3}$alkyl);

$R^{5a}$ is selected from one of the following seventeen groups:
1) hydrogen or $C_{1-5}$alkyl which may be unsubstituted or which may be substituted with one or more groups selected from hydroxy, fluoro and amino;
2) $C_{1-5}$alkyl$X^{3a}COR^{19a}$, wherein $X^{3a}$ represents —O— or —$NR^{20a}$— (in which $R^{20a}$ represents hydrogen, $C_{1-3}$ alkyl or $C_{1-3}$ alkoxy$C_{2-3}$alkyl) and $R^{19a}$ represents $C_{1-3}$alkyl, —$NR^{21a}R^{22a}$— or —$OR^{23a}$— (wherein $R^{21a}$, $R^{22a}$ and $R^{23a}$ which may be the same or different each represents hydrogen, $C_{1-3}$alkyl or $C_{1-3}$alkoxy$C_{2-3}$alkyl);
3) $C_{1-5}$alkyl$X^{4a}R^{24a}$, wherein $X^{4a}$ represents —O—, —S—, —SO—, —$SO_2$—, —OCO—, —$NR^{25a}CO$—, , —$CONR^{26a}$—, —$SO_2NR^{27a}$—, —NR$^{28a}$SO$_2$— or —NR$^{29a}$— (wherein R$^{25a}$ R$^{26a}$, R$^{27a}$, R$^{28a}$ and R$^{29a}$ each independently represents hydrogen, C$_{1-3}$alkyl or C$_{1-3}$alkoxyC$_{2-3}$alkyl) and R$^{24a}$ represents hydrogen, C$_{1-3}$alkyl, cyclopentyl, cyclohexyl or a 5 or 6-membered saturated heterocyclic group with one or two heteroatoms, selected independently from O, S and N, which C$_{1-3}$alkyl group may bear one or two substituents selected from oxo, hydroxy, halogeno and C$_{1-4}$alkoxy and which cyclic group may bear one or two substituents selected from oxo, hydroxy, halogeno, C$_{1-4}$alkyl, C$_{1-4}$hydroxyalkyl and C$_{1-4}$alkoxy;

4) C$_{1-5}$alkylX$^{5a}$C$_{1-5}$alkylX$^{6a}$R$^{30a}$, wherein X$^{5a}$ and X$^{6a}$ which may be the same or different are each —O—, —S—, —SO—, —SO$_2$—, —NR$^{31a}$CO—, —CONR$^{32a}$—, —SO$_2$NR$^{33a}$—, —NR$^{34a}$SO$_2$— or —NR$^{35a}$— (wherein R$^{31a}$, R$^{32a}$, R$^{33a}$, R$^{34a}$ and R$^{35a}$ each independently represents hydrogen, C$_{1-3}$alkyl or C$_{1-3}$alkoxyC$_{2-3}$alkyl) and R$^{30a}$ represents hydrogen or C$_{1-3}$alkyl;

5) R$^{36a}$, wherein R$^{36a}$ is a 5 or 6-membered saturated heterocyclic group with one or two heteroatoms, selected independently from O, S and N, which heterocyclic group may bear one or two substituents selected from oxo, hydroxy, halogeno, C$_{1-4}$alkyl, C$_{1-4}$hydroxyalkyl and C$_{1-4}$alkoxy;

6) C$_{1-5}$alkylR$^{36a}$, wherein R$^{36a}$ is as defined herein;

7) C$_{2-5}$alkynylR$^{36a}$, wherein R$^{36a}$ is as defined herein;

8) C$_{2-5}$alkenylR$^{36a}$, wherein R$^{36a}$ is as defined herein;

9) R$^{37a}$, wherein R$^{37a}$ represents a pyridone group, a phenyl group or a 5 or 6-membered aromatic heterocyclic group with 1 to 3 hetcroatoms selected from O, N and S, which pyridone, phenyl or heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —CONR$^{38a}$R$^{39a}$ and —NR$^{40a}$COR$^{41a}$— (wherein R$^{38a}$, R$^{39a}$, R$^{40a}$ and R$^{41a}$, which may be the same or different, each represents hydrogen, C$_{1-4}$alkyl or C$_{1-3}$alkoxyC$_{2-3}$alkyl);

10) C$_{1-5}$alkylR$^{37a}$, wherein R$^{37a}$ is as defined herein;

11) C$_{2-5}$ alkenyR$^{37a}$, wherein R$^{37a}$ is as defined herein;

12) C$_{2-5}$ alkynylR$^{37a}$, wherein R$^{37a}$ is as defined herein;

13) C$_{1-5}$alkyX$^{7a}$R$^{37a}$, wherein X$^{7a}$ represents —O—, —S—, —SO—, —SO$_2$—, —NR$^{42a}$CO—, —CONR$^{43a}$—, —SO$_2$NR$^{44a}$—, —NR$^{45a}$SO$_2$— or —NR$^{46a}$— (wherein R$^{42a}$, R$^{43a}$, R$^{44a}$, R$^{45a}$ and R$^{46a}$ each independently represents hydrogen, C$_{1-3}$alkyl or C$_{1-3}$alkoxyC$_{2-3}$alkyl) and R$^{37a}$ is as defined herein;

14) C$_{2-5}$alkenylX$^{8a}$R$^{37a}$, wherein X$^{8a}$ represents —O—, —S—, —SO—, —SO$_2$—, —NR$^{47a}$CO—, —CONR$^{48a}$—, —SO$_2$NR$^{49a}$—, —NR$^{50a}$SO$_2$— or —NR$^{51a}$— (wherein R$^{47a}$, R$^{48a}$, R$^{49a}$, R$^{50a}$ and R$^{51a}$ each independently represents hydrogen, C$_{1-3}$alkyl or C$_{1-3}$alkoxyC$_{2-3}$alkyl) and R$^{37a}$ is as defined herein;

15) C$_{2-5}$alkynylX$^{9a}$R$^{37a}$, wherein X$^{9a}$ represents —O—, —S—, —SO—, —SO$_2$—, —NR$^{52a}$CO—, —CONR$^{53a}$—, —SO$_2$NR$^{54a}$—, —NR$^{55a}$SO$_2$— or —NR$^{56a}$— (wherein R$^{52a}$, R$^{53a}$, R$^{54a}$, R$^{55a}$ and R$^{56a}$ each independently represents hydrogen, C$_{1-3}$alkyl or C$_{1-3}$alkoxyC$_{2-3}$alkyl) and R$^{37a}$ is as defined herein;

16) C$_{1-3}$alkylX$^{10a}$C$_{1-3}$alkylR$^{37a}$, wherein X$^{10a}$ represents —O—, —S—, —SO—, —SO$_2$—, NR$_{57a}$CO—, —CONR$^{58a}$, —SO$_2$NR$^{59a}$—, —NR$^{60a}$SO$_2$— or —NR$^{61a}$— (wherein R$^{57a}$, R$^{58a}$, R$^{59a}$, R$^{60a}$ and R$^{61a}$ each independently represents hydrogen, C$_{1-3}$alkyl or C$_{1-3}$alkoxyC$_{2-3}$alkyl) and R$^{37a}$ is as defined herein; and 17) C$_{1-3}$alkylX$^{10a}$C$_{1-3}$alkylR$^{36a}$, wherein X$^{10a}$ and R$^{36a}$ are as defined herein.

7. A compound as claimed in claim 6 wherein ring Z is a 6-membered heterocyclic ring containing 1 or 2 nitrogen atoms with the proviso that where R$^2$ is a group R$^4$X$^1$, X$^1$ is not C$_{2-4}$alkanoyl or —SO$_2$R$^{10}$— and R$^4$ is not optionally substituted phenyl or an optionally substituted 5 or 6-membered unsaturated heterocyclic ring.

8. A compound as claimed in claim 6 or 7 wherein R$^1$ is hydrogen.

9. A compound as claimed in claim 6 or 7 wherein R$^2$ is halogeno, C$_{1-2}$alkyl, C$_{1-2}$alkoxy, trifluoromethyl, 2,2,2-trifluoroethyl, cyano, nitro, C$_{1-3}$alkanoylamino, C$_{1-3}$alkylsulphonyl, carbamoyl, N-C$_{1-3}$alkylcarbamoyl, N,N-di(C$_{1-3}$alkyl)carbamoyl, aminosulphonyl, N-C$_{1-3}$alkylaminosulphonyl, N,N-di(C$_{1-3}$alkyl)aminosulphonyl or C$_{1-3}$alkylsulphonylamino or R$^2$ is selected from one of the following four groups:

1) R$^4$X$^1$, wherein X$^1$ represents —O—, —NR$^5$—, C$_{1-3}$alkyl, —CONR$^6$R$^7$— or —SO$_2$NR$^8$R$^9$— (wherein R$^5$, R$^6$, and R$^8$, each independently represents hydrogen or C$_{1-2}$alkyl and R$^7$ and R$^9$ each independently represents C$_{1-3}$alkyl and wherein R$^4$ is linked to R$^7$ or R$^9$) and R$^4$ represents a 5 or 6-membered saturated heterocyclic group with one or two heteroatoms, selected independently from O, S and N, which heterocyclic group may bear two oxo substituents on a ring sulphur heteroatom;

2) X$^2$C$_{2-3}$alkylX$^3$methyl, wherein X$^2$ is —O— or —NR$^{11}$— (wherein R$^{11}$ is hydrogen or C$_{1-2}$alkyl) and X$^3$ is —O—, —NR$^{12}$or —SO$_2$— (wherein R$^{12}$ is hydrogen or C$_{1-2}$alkyl);

3) C$_{1-2}$alkylX$^4$C$_{2-3}$alkylX$^5$methyl, wherein X$^4$ and X$^5$ which may be the same or different are each —NR$^{13}$— or —SO$_2$— (wherein R$^{13}$ is hydrogen or C$_{1-2}$alkyl); and 4) C$_{1-2}$alkylX$^6$C$_{1-2}$alkyl, wherein X$^6$ is —O—, —NR$^{14}$— or —SO$_2$— (wherein R$^{14}$ is hydrogen or C$_{1-2}$alkyl).

10. A compound as claimed in claim 6 or 7 wherein R$^3$, is hydrogen.

11. A compound as claimed in claim 6 or 7 wherein R$^{4a}$ is hydrogen, hydroxy, cyano, nitro, trifluoromethyl, methyl, ethyl, methoxy, ethoxy or a group R$^{8a}$ (CH$_2$)$_{ta}$X$^{2a}$, wherein R$^{8a}$ is a group selected from pyrrolidinyl, piperazinyl, piperidinyl, morpholino and thiomorpholino which group may carry one or two substituents selected from oxo, hydroxy, halogeno, C$_{1-2}$alkyl, C$_{1-2}$hydroxyalkyl and C$_{1-2}$alkoxy, X$^{2a}$ is —O—, —S—, —NR$^{9a}$CO—, —NR$^{12a}$SO$_2$— (wherein R$^{9a}$ and R$^{12a}$ each independently represents hydrogen or C$^{1-2}$alkyl) or NH, and ta is an integer from 1 to 3.

12. A compound as claimed in claim 6 or 7 herein X$^{1a}$ is —O—, —S—, —NR$^{14a}$CO—, —NR$^{17a}$SO$_2$— (wherein R$^{14a}$ and R$^{17a}$ each independently represents hydrogen or C$_{1-2}$alkyl) or NH.

13. A compound as claimed in claim 6 or 7 wherein $R^{5a}$ is selected from one of the following fifteen groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)etlhyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^{4a}R^{24a}$, wherein $X^{4a}$ is as defined in claim 6 and $R^{24a}$ is a group selected from $C_{1-2}$alkyl, cyclopentyl, cyclohexyl, pyrrolidinyl and piperidinyl which group is linked to $X^{4a}$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy;

4) $C_{2-3}$alkyl$X^{5a}C_{2-3}$alkyl$X^{6a}R^{30a}$, wherein $X^{5a}$ and $X^{6a}$ are as defined in claim 6 and $R^{30a}$ represents hydrogen or $C_{1-2}$alkyl;

5) $R^{36a}$, wherein $R^{36a}$ is as defined in claim 6;

6) $C_{1-2}$alkyl$R^{65a}$ (wherein $R^{65a}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{66a}$ (wherein $R^{66a}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);

7) $R^{37a}$, wherein $R^{37a}$ is as defined in claim 6;

8) $C_{1-4}$alkyl$R^{37a}$, wherein $R^{37a}$ is as defined in claim 6;

9) 1-$R^{37a}$but-2-en-4-yl, wherein $R^{37a}$ is as defined in claim 6;

10) 1-$R^{37a}$but-2-yn-4-yl, wherein $R^{37a}$ is as defined in claim 6;

11) $C_{2-4}$alkyl$X^{7a}R^{37a}$, wherein $X^{7a}$ and $R^{37a}$ are as defined in claim 6;

12) 1-($R^{37a}X^{8a}$)but-2-en-4-yl, wherein $X^{8a}$ and $R^{37a}$ are as defined in claim 6;

13) 1-($R^{37a}X^{9a}$)but-2-yn-4-yl, wherein $X^{9a}$ and $R^{37a}$ are as defined in claim 6;

14) ethyl$X^{10a}$methyl$R^{37a}$, wherein $X^{10a}$ and $R^{37a}$ are as defined in claim 6; and 15) ethyl$X^{10a}$methyl$R^{36a}$, wherein $X^{10a}$ and $R^{36a}$ are as defined in claim 6.

14. A compound of the formula Ib:

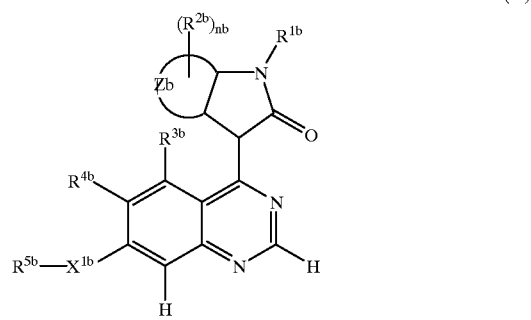

(Ib)

wherein:
$R^{1b}$ represents hydrogen;
$R^{2b}$ represents halogeno, $C_{1-2}$alkyl, $C_{1-2}$alkoxy, trifluoromethyl, 2,2,2-trifluoroethyl, cyano, nitro, $C_{1-3}$alkanoylamino, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)-aminosulphonyl or $C_{1-3}$alkylsulphonylamino or $R^{2b}$ is selected from one of the following four groups:

1) $R^{6b}X^{2b}$, wherein $X^{2b}$ represents —O—, —NR$^{7b}$—, $C_{1-3}$alkyl, —CONR$^{8b}$R$^{9b}$— or —SO$_2$NR$^{10b}$R$^{11b}$— (wherein R$^{7b}$, R$^{8b}$, and R$^{10b}$, each independently represents hydrogen or $C_{1-2}$alkyl and R$^{9b}$ and R$^{11b}$ each independently represents $C_{1-3}$alkyl and wherein R$^{6b}$ is linked to R$^{9b}$ or R$^{11b}$) and R$^{6b}$ represents a 5 or 6-membered saturated heterocyclic group with one or two heteroatoms, selected independently from O, S and N, which heterocyclic group may bear two oxo substituents on a ring sulphur heteroatom;

2) $X^{3b}C_{2-3}$alkyl$X^{4b}$methyl, wherein $X^{3b}$ is —O— or —NR$^{12b}$— (wherein R$^{12b}$ is hydrogen or $C_{1-2}$alkyl) and $X^{4b}$ is —O—, —NR$^{13b}$— or —SO$_2$— (wherein R$^{13b}$ is hydrogen or $C_{1-2}$alkyl);

3) $C_{1-2}$alkyl$X^{5b}C^{2-3}$alkyl$X^{6b}$methyl, wherein $X^{5b}$ and $X^{6b}$ which may be the same or different are each —NR$^{14b}$— or —SO$_2$— (wherein R$^{14b}$ is hydrogen or $C_{1-2}$alkyl); and 4) $C_{1-2}$alkyl$X^{7b}C_{1-2}$alkyl, wherein $X^{7b}$ is —O—, —NR$^{15b}$ or —SO$_2$— (wherein R$^{15b}$ is hydrogen or $C_{1-2}$alkyl);

nb is an integer from 0 to 2;

ring Zb is a 6-membered aromatic heterocyclic ring containing 1 or 2 nitrogen atoms such that the substituent at the 4-position of the quinazoline ring is selected from the groups 7-azaoxindol-3-yl and 5,7-diazaoxindol-3-yl which group bears ($R^{2b}$)$_{nb}$ as defined herein;

$R^{2b}$ is attached at the 5- and/or 6-positions of the heteroaromatic oxindole ring, but if $R^{2b}$ is fluoro it can be attached at the 4-, 5-, 6- or 7-position(s) of the heteroaromatic oxindole ring;

$R^{3b}$ represents hydrogen;

$R^{4b}$ represents hydrogen, hydroxy, cyano, nitro, trifluoromethyl, methyl, methoxy or a group $R^{16b}$(CH$_2$)$_{tb}X^{8b}$, wherein $R^{16b}$ represents a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, tb is an integer from 1 to 3 and Xsb represents —O—, —S—, —NR$^{17b}$CO—, —NR$^{18b}$SO$_2$— (wherein R$^{17b}$ and R$^{18b}$ each independently represents hydrogen or C$_{1-2}$alkyl) or NH;

X$^{1b}$ represents —O— or —NR$^{19b}$CO— (wherein R$^{19b}$ represents hydrogen or C$_{1-2}$alkyl); and R$^{5b}$ represents methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(1,2,4-triazol-1-yl)ethyl, 2-(1,2,4-triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl)ethyl, 3-(5-methyl-1,2,4-triazol-1-yl)propyl, morpholino, N-methylpiperazinyl, piperazinyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-methoxyethyl, 3-methoxypropyl, 2-(imidazol-1-yl)ethyl, 2-(1,2,3-triazol-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(methylsulphinyl)ethyl or 2-(methylsulphonyl)ethyl.

15. A compound selected from:
4-(7-azaoxindol-3-yl)-6-methoxy-7-(3-morpholinopropoxy)quinazoline;
4-(7-azaoxindol-3-yl)-7-(2-(imidazol-1-yl)ethoxy)-6-methoxyquinazoline;
4-(5,7-diaza-6-methyloxindol-3-yl)-7-(3-morpholinopropoxy)quinazoline; and
4-(4-aza-6-trifluoromethyloxindol-3-yl) 6-methoxy-7-(3-morpholinopropoxy)quinazoline;
and salts thereof.

16. A compound selected from:
4-(5,7-diaza-6-methyloxindol-3-y)-7-(3-(1,1-dioxothiomorpholino)propoxy)quinazoline;
4-(7-aza-6-chlorooxindol-3-yl)-7-(3-morpholinopropoxy)quinazoline;
4-(7-azaoxindol-3-yl)-7-(4-morpholinobut-2-en-1-yloxy)quinazoline; and
4-(5,7-diaza-6-methyloxindol-3-yl)-7-(3-methylsulphonylpropoxy)quinazoline;
and salts thereof.

17. A compound selected from:
4-(5,7-diaza-6-methyloxindol-3-yl)-7-(3-morpholinopropoxy)quinazoline;
4-(7-azaoxindol-3-yl)-7-(2-(2-methoxyethoxy)ethoxy)quiiazoline; and
4-(7-azaoxindol-3-yl)-7-(3-morpholinopropoxy)quinazoline;
and salts thereof.

18. A compound as claimed in any one of claims 1, 6, 14, 15, 16 and 17 in the form of a pharmaceutically acceptable salt.

19. A process for the preparation of a compound of formula I or salt thereof, as defined in claim 1, which comprises:

(a) the reaction of a compound of the formula III:

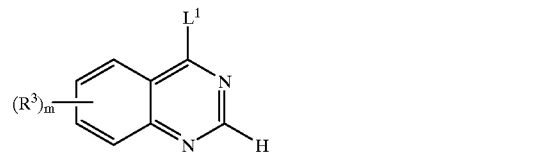

(III)

wherein R$^3$ and m are as defined in claim 1 and L$^1$ is a displaceable moiety, with a compound of the formula IV:

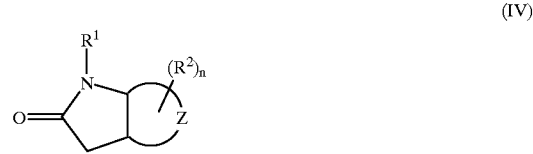

(IV)

wherein R$^1$, R$^2$ ring Z and n are as defined in claim 1, whereby to obtain compounds of the formula I and salts thereof;

(b) the deprotection of a compound of formula V:

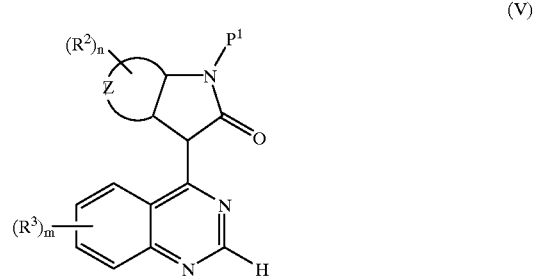

(V)

wherein R$^2$, R$^3$, n, ring Z and m are as defined in claim 1 and P$^1$ represents a protecting group;

(c) the reduction and cyclisation of a compound of formula VI:

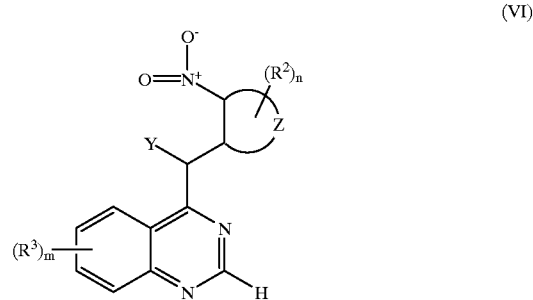

(VI)

wherein R$^2$, R$^3$, m, ring Z and n are as defined in claim 1 and Y represents cyano, carboxy or C$_{1-4}$alkoxycarbonyl;

(d) for the preparation of those compounds of formula I and salts thereof wherein at least one of the $R^2$ groups is hydroxy, the deprotection of a compound of formula VII:

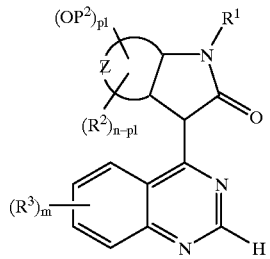

(VII)

wherein $R^1$, $R^2$, $R^3$, n, ring Z and m are as defined in claim 1, $P^2$ represents a phenolic hydroxy protecting group and p1 is an integer from 1 to 3 equal to the number of protected hydroxy groups and such that n-p1 is equal to the number of $R^2$ substituents which are not protected hydroxy;

(e) for the preparation of those compounds of formula I and salts thereof wherein at least one $R^3$ is $R^{15}X^7$ wherein $R^{15}$ is as defined in claim 1 and $X^7$ is —O—, —S—, —SO$_2$—, —CONR$^{17}$, —SO$_2$NR$^{18}$— or —NR$^{20}$— (wherein $R^{17}$, $R^{18}$ and $R^{20}$ each independently represents hydrogen, $C_{1-3}$alkyl or $C_{1-3}$alkoxy$C_{2-3}$alkyl) the reaction of a compound of the formula VIII:

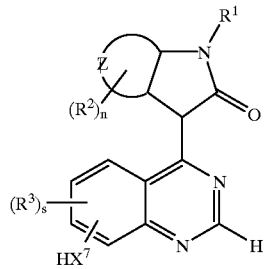

(VIII)

wherein $R^1$, $R^2$, $R^3$, n, ring Z and $X^7$ are as defined in claim 1 and s is an integer from 0 to 3, with a compound of formula IX:

 $R^{15}$—$L^1$ (IX)

wherein $R^{15}$ is as defined in claim 1 and $L^1$ is as defined herein;

(f) for the preparation of those compounds of formula I and salts thereof wherein at least one $R^3$ is $R^{15}X^7$ wherein $R^{15}$ is as defined in claim 1 $X^7$ is —O—, —S—, or —NR$^{20}$— (wherein $R^{20}$ represents hydrogen, $C_{1-3}$alkyl or $C_{1-3}$alkoxy$C_{2-3}$alkyl), the reaction of a compound of the formula X:

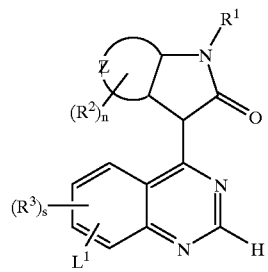

(X)

with a compound of the formula XI:

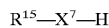 $R^{15}$—$X^7$—H (XI)

wherein $L^1$ and s are as defined herein and $R^1$, $R^2$, $R^3$, $R^{15}$, n, ring Z and $X^7$ are all as defined in claim 1;

(g) for the preparation of compounds of formula I and salts thereof wherein at least one $R^3$ is $R^{15}X^7$ wherein $X^7$ is as defined in claim 1 and $R^{15}$ is $C_{1-5}$alkyl$R^{70}$, wherein $R^{70}$ is selected from one of the following six groups:

1) $X^{16}C_{1-3}$alkyl, wherein $X^{16}$ represents —O—, —S—, —SO$_2$—, —NR$^{71}$CO— or —NR$^{72}$SO$_2$— (wherein $R^{71}$ and $R^{72}$ which may be the same or different are each hydrogen, $C_{1-3}$alkyl or $C_{1-3}$alkoxy$C_{2-3}$alkyl);

2) NR$^{73}$R$^{74}$, wherein $R^{73}$ and $R^{74}$ which may be the same or different are each hydrogen, $C_{1-3}$alkyl or $C_{1-3}$alkoxy$C_{2-3}$alkyl;

3) $X^{17}C_{1-5}$alkyl$X^{11}R^{32}$, wherein $X^{17}$ represents —O—, —S—, —SO$_2$—, —NR$^{75}$CO—, —NR$^{76}$SO$_2$— or —NR$^{77}$— (wherein $R^{75}$, $R^{76}$, and $R^{77}$ which may be the same or different are each hydrogen, $C_{1-3}$alkyl or $C_{1-3}$alkoxy$C_{2-3}$alkyl) and $X^{11}$ and $R^{32}$ are as defined in claim 1, 4) $R^{65}$, wherein $R^{65}$ is a 5 or 6-membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy;

5) $X^{18}R^{39}$, wherein $X^8$ represents —O—, —S—, —SO$_2$—, —NR$^{78}$CO—, —NR$^{79}$SO$_2$—, or —NR$^{80}$— (wherein $R^{78}$, $R^{79}$, and $R^{80}$ which may be the same or different are each hydrogen, $C_{1-3}$alkyl or $C_{1-3}$alkoxy$C_{2-3}$alkyl) and $R^{39}$ is as defined in claim 1; and 6) $X^{19}C_{1-5}$alkyl$R^{39}$, wherein $X^{19}$ represents —O—, —S—, —SO$_2$—, —NR$^{81}$CO—, —NR$^{82}$SO$_2$— or —NR$^{83}$— (wherein $R^{81}$, $R^{82}$ and $R^{83}$ each independently represents hydrogen, $C_{1-3}$alkyl or $C_{1-3}$alkoxy$C_{2-3}$alkyl) and $R^{39}$ is as defined in claim 1;

reacting a compound of the formula XII:

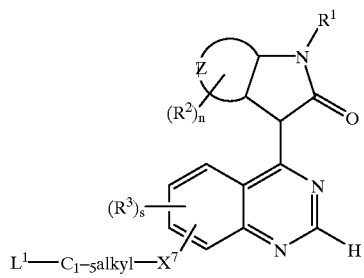

(XII)

wherein $L^1$ and s are as defined herein and $X^7$, $R^1$, $R^2$, $R^3$, n and ring Z are as defined in claim 1, with a compound of the formula XIII:

$R^{70}$—H  (XIII)

wherein $R^{70}$ is as defined herein, to give a compound of the formula I or salt thereof, (h) for the preparation of those compounds of formula I and salts thereof wherein one or more of the substituents $(R^3)_m$ is represented by —$NR^{84}R^{85}$—, where one or both of $R^{84}$ and $R^{85}$ are $C_{1-3}$alkyl, the reaction of compounds of formula I wherein the substituent $(R^3)_m$ is an amino group and an alkylating agent;

for the preparation of those compounds of formula I and salts thereof wherein one or more of the substituents $R^2$ or $R^3$ is an amino group the reduction of a corresponding compound of formula I wherein the substituent(s) at the corresponding position(s) of the quinazoline and/or heteroaromatic oxindole group is/are a nitro group(s);

and when a salt of a compound of formula I is required, reaction of the compound obtained with an acid or base whereby to obtain the desired salt.

20. A pharmaceutical composition which comprises as active ingredient a compound as claimed in any one of claims 1, 6, 14, 15, 16 and 17, or a pharmaceutically acceptable salt thereof, in association with a pharmaceutically acceptable excipient or carrier.

21. A method for producing an antiangiogenic and/or vascular permeability reducing effect in a warm-blooded animal in need of such treatment which comprises administering to said animal an effective amount of a compound of formula I as defined in claim 1 or a pharmaceutically acceptable salt thereof.

22. A method for the treatment, in a warm blooded animal in need thereof, of a primary or recurrent solid tumor that is dependent on VEGF and/or FGF for its growth and spread, said method comprising administering to said animal an effective amount of a compound as claimed in any one of claims 1, 6, 14, 15, 16 and 17, or a pharmaceutically acceptable salt thereof.

23. The method of claim 22, wherein said tumor is a tumor of the colon, breast, prostate, lung, vulva or skin.

* * * * *